(12) United States Patent  
Kang et al.

(10) Patent No.: US 10,335,062 B2  
(45) Date of Patent: Jul. 2, 2019

(54) ELECTRONIC DEVICE INCLUDING FINGERPRINT SENSOR

(71) Applicant: Samsung Electronics Co., Ltd., Gyeonggi-do (KR)

(72) Inventors: Han-Vit Kang, Gyeonggi-do (KR); Ho-Kyung Kang, Daegu (KR); Byeong-Cheol Kim, Gyeonggi-do (KR); Jung-Won Kim, Gyeonggi-do (KR); Jeong-Sik Jeong, Gyeonggi-do (KR); Kwang-Tai Kim, Gyeonggi-do (KR); Hyung-Sup Byeon, Gyeonggi-do (KR); Hyun-Ju Hong, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 134 days.

(21) Appl. No.: 15/668,356

(22) Filed: Aug. 3, 2017

(65) Prior Publication Data  
US 2018/0035923 A1 Feb. 8, 2018

(30) Foreign Application Priority Data  
Aug. 5, 2016 (KR) .................. 10-2016-0100159

(51) Int. Cl.  
*A61B 5/00* (2006.01)  
*G06K 9/00* (2006.01)  
*A61B 5/117* (2016.01)  
*G01B 7/28* (2006.01)  
*G01B 11/24* (2006.01)  
*G06K 19/08* (2006.01)  
(Continued)

(52) U.S. Cl.  
CPC ............... *A61B 5/117* (2013.01); *G01B 7/28* (2013.01); *G01B 11/24* (2013.01); *G06K 9/0002* (2013.01); *G06K 19/08* (2013.01); *H01L 27/146* (2013.01); *A61B 5/00* (2013.01); *A61B 5/6898* (2013.01); *G06K 19/00* (2013.01)

(58) Field of Classification Search  
CPC .................................................. G06K 9/0002  
See application file for complete search history.

(56) References Cited

U.S. PATENT DOCUMENTS

| | | | | |
|---|---|---|---|---|
| 8,745,490 B2* | 6/2014 | Kim | .................. | G06F 3/042 345/173 |
| 9,030,440 B2* | 5/2015 | Pope | ..................... | G06F 3/044 345/174 |

(Continued)

FOREIGN PATENT DOCUMENTS

| | | |
|---|---|---|
| KR | 1020150087811 | 7/2015 |
| KR | 1020160000100 | 1/2016 |

*Primary Examiner* — Utpal D Shah  
(74) *Attorney, Agent, or Firm* — The Farrell Law Firm, P.C.

(57) ABSTRACT

An electronic device is provided which includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a fingerprint sensor disposed between the transparent cover and the display, a touch sensor disposed between the fingerprint sensor and the display, and a pressure sensor disposed between the display and the second face of the housing.

17 Claims, 42 Drawing Sheets

(51) Int. Cl.
*H01L 27/146* (2006.01)
*G06K 19/00* (2006.01)

(56) References Cited

U.S. PATENT DOCUMENTS

| | | | | |
|---|---|---|---|---|
| 9,454,253 | B2* | 9/2016 | Kim | G06F 3/0412 |
| 10,007,343 | B2* | 6/2018 | Kim | G06F 3/016 |
| 10,152,173 | B2* | 12/2018 | Qu | G06F 3/0416 |
| 2015/0235098 | A1* | 8/2015 | Lee | G06F 9/00912 |
| | | | | 715/709 |
| 2015/0370356 | A1 | 12/2015 | Hwang et al. | |
| 2016/0033342 | A1 | 2/2016 | Lyon et al. | |
| 2016/0062500 | A1 | 3/2016 | Kessler et al. | |
| 2017/0103246 | A1* | 4/2017 | Pi | G06K 9/0002 |
| 2017/0372122 | A1* | 12/2017 | Shim | G06F 3/0414 |
| 2018/0107332 | A1* | 4/2018 | Chan | G06F 3/0412 |
| 2018/0326456 | A1* | 11/2018 | Park | G06F 3/0416 |
| 2018/0329558 | A1* | 11/2018 | Park | G06F 3/0414 |

* cited by examiner

ELECTRONIC DEVICE INCLUDING FINGERPRINT SENSOR

PRIORITY

This application claims priority under 35 U.S.C. § 119(a) to Korean Patent Application Serial No. 10-2016-0100159, which was filed in the Korean Intellectual Property Office on Aug. 5, 2016, the entire content of which is incorporated herein by reference.

BACKGROUND

1. Field of the Disclosure

The present disclosure generally relates to an electronic device, and more particularly, to an electronic device including a fingerprint sensor.

2. Description of the Related Art

A display device is a device for outputting an image or image information, and may be installed in electronic devices that are equipped with an information communication function. Due to the development of electric and electronic technologies, the performance of the display device has developed such that the image quality displayed has been remarkably improved, and the display device has been integrated with a touch panel such that the display device is utilized not only as an output device, but also as an input device.

An electronic device including a display device may recognize and confirm a user through a connection with a part of the user's body in addition to calculating a horizontal element (e.g., a position or movement) of an input based on the input to a touch panel. In particular, a fingerprint recognition device is widely used due to low cost, ease of use, and accuracy, among personal authentication systems using biometrics, such as a fingerprint, a voice, a face, a hand, and an iris in order to recognize a user.

Various recognition methods, such as an optical method, a heat sensing method, and a capacitance method are known methods for implementing a fingerprint recognition sensor. Among them, a capacitive-type fingerprint recognition sensor acquires a pattern of a fingerprint by detecting a change in capacitance depending on the shapes of ridges and valleys of the fingerprint when the finger surface of a human touches a conductive detection pattern.

In addition, as the electronic device becomes smaller and thinner, the position and space requirements of the fingerprint sensor have become restricted. Furthermore, a touch sensing technology and a fingerprint recognition technology are individually implemented to enable individual functions for specific situations at the time of use. In the case of an electronic device including both the touch sensing function and the fingerprint recognition function, additional cost for each of the functions may be incurred in order to individually develop and implement each of the functions.

SUMMARY

The present disclosure has been made to address at least the above disadvantages and other disadvantages not described above, and to provide at least the advantages described below.

According to an aspect of the present disclosure, an electronic device is provided which calculates the horizontal position and the vertical position of a touch input based on various types of touch inputs. In addition, the electronic device is mounted with a fingerprint recognition sensor capable of recognizing a user. The fingerprint sensor requires a separate space because it has a hardware structure that is separate from the display.

According to another aspect of the present disclosure, an electronic device is provided which includes a fingerprint sensor that is disposed on a front face of a display to reduce restrictions on a mounting space and to have an integrated structure with a touch sensor or a pressure sensor.

In accordance with an aspect of the present disclosure, an electronic device is provided which includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a fingerprint sensor disposed between the transparent cover and the display, a touch sensor disposed between the fingerprint sensor and the display; and a pressure sensor disposed between the display and the second face of the housing.

In accordance with another aspect of the present disclosure, an electronic device is provided which includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a first electrode disposed between the transparent cover and the display, a second electrode disposed between the first electrode and the display, a third electrode disposed between the second electrode and the display, a fourth electrode disposed between the third electrode and the display, and at least one control circuit electrically connected to the display, the first electrode, the second electrode, the third electrode, and the fourth electrode.

In accordance with another aspect of the present disclosure, an electronic device is provided which includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a first electrode disposed between the transparent cover and the display, a second electrode disposed between the first electrode and the display, a third electrode disposed between the second electrode and the display, a fourth electrode disposed to be coplanar with the third electrode, and at least one control circuit electrically connected to the display, the first electrode, the second electrode, the third electrode, and the fourth electrode.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
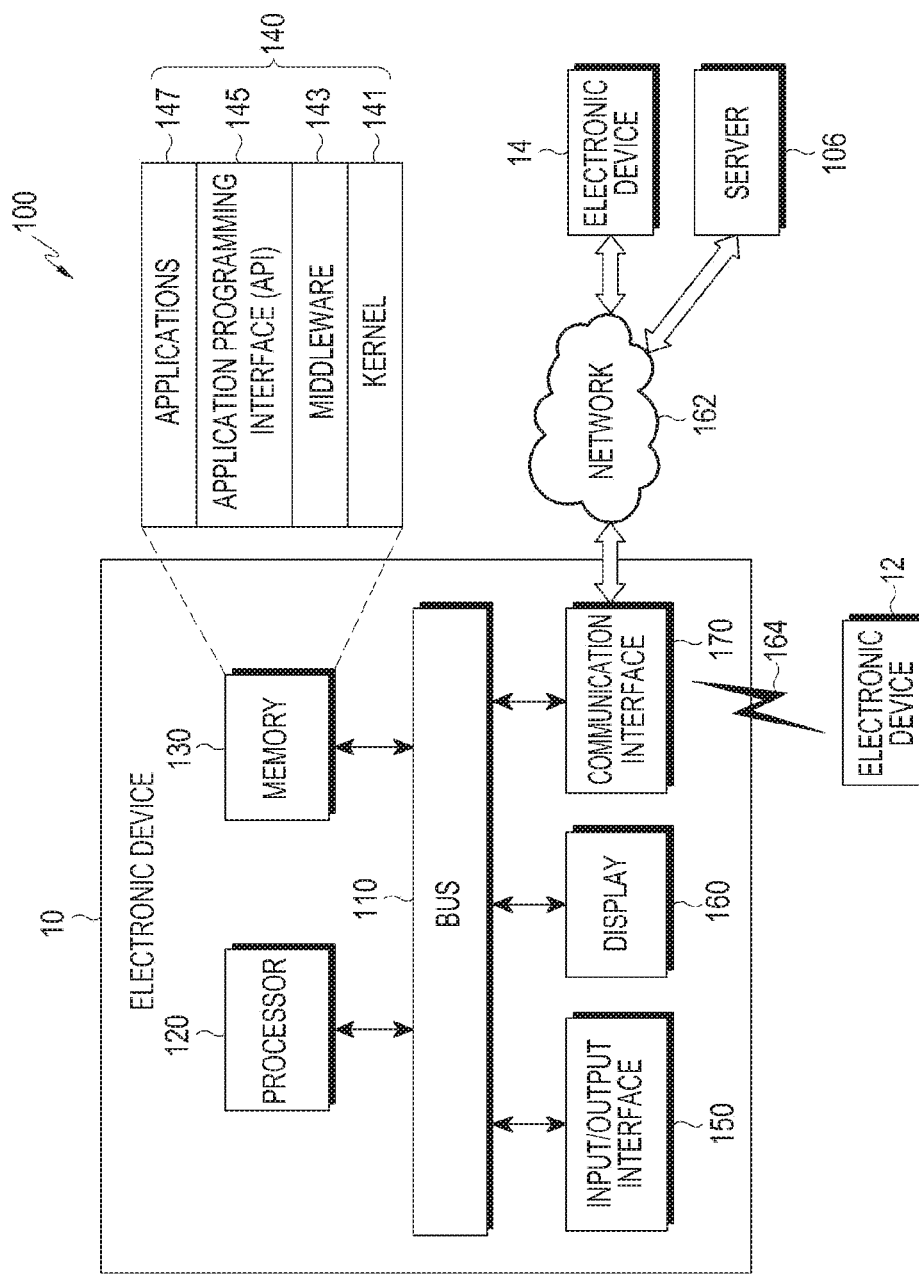
FIG. 1 is a block diagram of an electronic device within a network environment, according to an embodiment of the present disclosure.

Hereinafter, certain embodiments of the present disclosure will be described with reference to the accompanying drawings. The embodiments and terms used herein do not limit the technology disclosed herein to specific forms, and should be understood to include various modifications, equivalents, and/or alternatives to the corresponding embodiments. In the description of the drawings, similar reference numerals may be used to designate similar elements. A singular expression may include a plural expression unless they are different in context. As used herein, singular forms may include plural forms as well unless the context clearly indicates otherwise.

The expressions "a first", "a second", "the first", or "the second" as used in certain embodiments of the present disclosure may modify various components regardless of the order and/or the importance but do not limit the corresponding components. When an element (e.g., first element) is referred to as being "(functionally or communicatively) connected," or "directly coupled" to another element (second element), the element may be connected directly to the other element or connected to the other element through another element (e.g., third element).

The expression "configured to" as used in certain embodiments of the present disclosure may be interchangeably used with, for example, "suitable for", "having the capacity to", "designed to", "adapted to", "made to", or "capable of" in terms of hardware or software, according to circumstances. Alternatively, in some situations, the expression "device configured to" may mean that the device, together with other devices or components, "is able to". The phrase "processor adapted (or configured) to perform A, B, and C" may mean a dedicated processor (e.g., embedded processor) only for performing the corresponding operations or a general-purpose processor (e.g., central processing unit (CPU) or application processor (AP)) that may perform the corresponding operations by executing one or more software programs stored in a memory device.

An electronic device, according to an embodiment of the present disclosure, may include at least one of, for example, a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), an MPEG-1 audio layer-3 (MP3) player, a mobile medical device, a camera, and a wearable device. The wearable device may include at least one of an accessory type (e.g., a watch, a ring, a bracelet, an anklet, a necklace, a glasses, a contact lens, or a head-mounted device (HMD)), a fabric or clothing integrated type (e.g., an electronic clothing), a body-mounted type (e.g., a skin pad, or tattoo), and a bio-implantable type (e.g., an implantable circuit). The electronic device may include at least one of, for example, a television, a digital video disk (DVD) player, an audio player, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

The electronic device may include at least one of various medical devices (e.g., various portable medical measuring devices (a blood glucose monitoring device, a heart rate monitoring device, a blood pressure measuring device, a body temperature measuring device, etc.), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), a vehicle infotainment device, an electronic device for a ship (e.g., a navigation device for a ship, and a gyro-compass), avionics, security devices, an automotive head unit, a robot for home or industry, an automatic teller machine (ATM), point of sales (POS) terminal, or Internet of things (IoT) device (e.g., a light bulb, various sensors, electric or gas meter, a sprinkler device, a fire alarm, a thermostat, a streetlamp, a toaster, a sporting good, a hot water tank, a heater, a boiler, etc.).

An electronic device may include at least one of a part of furniture or a building/structure, an electronic board, an electronic signature receiving device, a projector, and various types of measuring instruments (e.g., a water meter, an electric meter, a gas meter, a radio wave meter, and the like). The electronic device may be flexible, or may be a combination of one or more of the aforementioned various devices. The electronic device is not limited to the above described devices. In the present disclosure, the term "user" may indicate a person using an electronic device or a device (e.g., an artificial intelligence electronic device) using an electronic device.

FIG. 1 is a block diagram of an electronic device within a network environment, according to an embodiment of the present disclosure. An electronic device 10 within the network environment 100, will be described with reference to FIG. 1. The electronic device 10 includes a bus 110, a processor 120, a memory 130, an input/output interface 150, a display 160, and a communication interface 170. At least one of the above-mentioned components may be omitted from the electronic device 10, or the electronic device 10 may additionally include other components. The bus 110 may include a circuit that interconnects the above-mentioned components 110 to 170 and transmits communication (e.g., a control message or data) among the components 110 to 170. The processor 120 may include one or more of a central processing unit (CPU), an application processor (AP), and a communication processor (CP). The processor 120 may execute, for example, an arithmetic operation or data processing that is related to a control and/or communication of one or more other components of the electronic device 10.

The memory 130 may include a volatile memory and/or a non-volatile memory. The memory 130 may store, for example, commands or data that are related to one or more other components of the electronic device 10. According to an embodiment of the present disclosure, the memory 130 may store software and/or a program 140. The program 140 includes, for example, a kernel 141, a middleware 143, an application programming interface (API) 145, and/or an applications 147. At least one of the kernel 141, the middleware 143, and the API 145 may be referred to as an operating system (OS). The kernel 141 may control or manage, for example, system resources (e.g., the bus 110, the processor 120, or the memory 130) that are used for executing operations or functions implemented in the other programs (e.g., the middleware 143, the API 145, or the applications 147). In addition, the kernel 141 may provide an interface that allows the middleware 143, the API 145, or the applications 147 to access individual components of the electronic device 10 to control or manage the system resources.

The middleware 143 may play an intermediary role such that, The API 145 or the applications 147 may communicate with the kernel 141 to exchange data. In addition, the middleware 143 may process one or more task requests which are received from the applications 147, according to priority. The middleware 143 may assign the priority to be capable of using a system resource of the electronic device 10 (e.g., the bus 110, the processor 120, or the memory 130) to at least one of the applications 147, and may process the one or more task requests. The API 145 is, for example, an interface that allows the applications 147 to control functions provided from the kernel 141 or the middleware 143, and may include, for example, one or more interfaces or functions (e.g., commands) for a file control, a window control, an image processing, or a character control. The input/output interface 150 may transmit commands or data, which are entered by, for example, a user or any other external device, to the other component(s) of the electronic device 10, or may output commands or data, which are received from the other component(s) of the electronic device 10, to the user or the other external device.

The display device 160 may include, for example, a liquid crystal display (LCD), a light emitting diode (LED) display, an organic light emitting diode (OLED) display, a microelectromechanical system (MEMS) display, or an electronic paper display. The display 160 may display various content (e.g., text, image, video, icon, or symbol) to, for example, the user. The display 160 may include a touch screen, and may receive a touch input, a gesture input, a proximity input, or a hover input that is made using, for example, an electronic pen or a part of the user's body. The communication interface 170 may set, for example, communication between the electronic device 10 and a first external electronic device 12, a second external device 14, or a server 106. The communication interface 170 may be connected with a network 162 through wired or wireless communication so as to communicate with the second external electronic device 14 or the server 106.

The wireless communication may include cellular communication that uses at least one of, for example, long-term evolution (LTE), LTE advance (LTE-A), code division multiple access (CDMA), wideband CDMA (WCDMA), universal mobile telecommunication system (UMTS), wireless broadband (WiBro), and global system for mobile communication (GSM). The wireless communication may include at least one of, Wireless fidelity (WiFi), Bluetooth™, Bluetooth™ low energy (BLE), ZigBee™, near field communication (NFC), magnetic secure transmission, radio frequency (RF), and body area network (BAN). The wireless communication may include GNSS. The GNSS may include, for example, at least one of global positioning system (GPS), global navigation satellite system (Glonass), Beidou navigation satellite system (Beidou), Galileo, and the European global satellite-based navigation system, according to, for example, a use area or band width. Herein, the term "GPS" may be interchangeably used with the term "GNSS" below. The wired communication may use at least one of, for example, universal serial bus (USB), high definition multimedia interface (HDMI), recommended standard 232 (RS-232), and plain old telephone service (POTS). The network 162 may include a telecommunication network (e.g., at least one of a computer network (e.g., LAN or WAN), the Internet, and a telephone network).

Each of the first and second external electronic devices 12 and 14 may be of a type that is the same as or different from that of the electronic device 10. According to an embodiment of the present disclosure, all or some of the operations to be executed by the electronic device 10 may be executed in another electronic device or a plurality of other electronic devices (e.g., the electronic devices 12 and 14 or the server 106). In the case where the electronic device 10 performs a certain function or service automatically or upon request, the electronic device 10 may request some functions or services that are associated therewith from the electronic devices 12 and 14 or the server 106, instead of, or in addition to, executing the functions or service by itself The electronic devices 12 and 14 or the server 106 may execute the requested functions or additional functions, and may deliver the results to the electronic device 10. The electronic device 10 may provide the requested functions or services by processing the received results as they are or additionally. For this purpose, for example, a cloud computing technique, a distributed computing technique, or a client-server computing technique may be used.

Figure 2A:
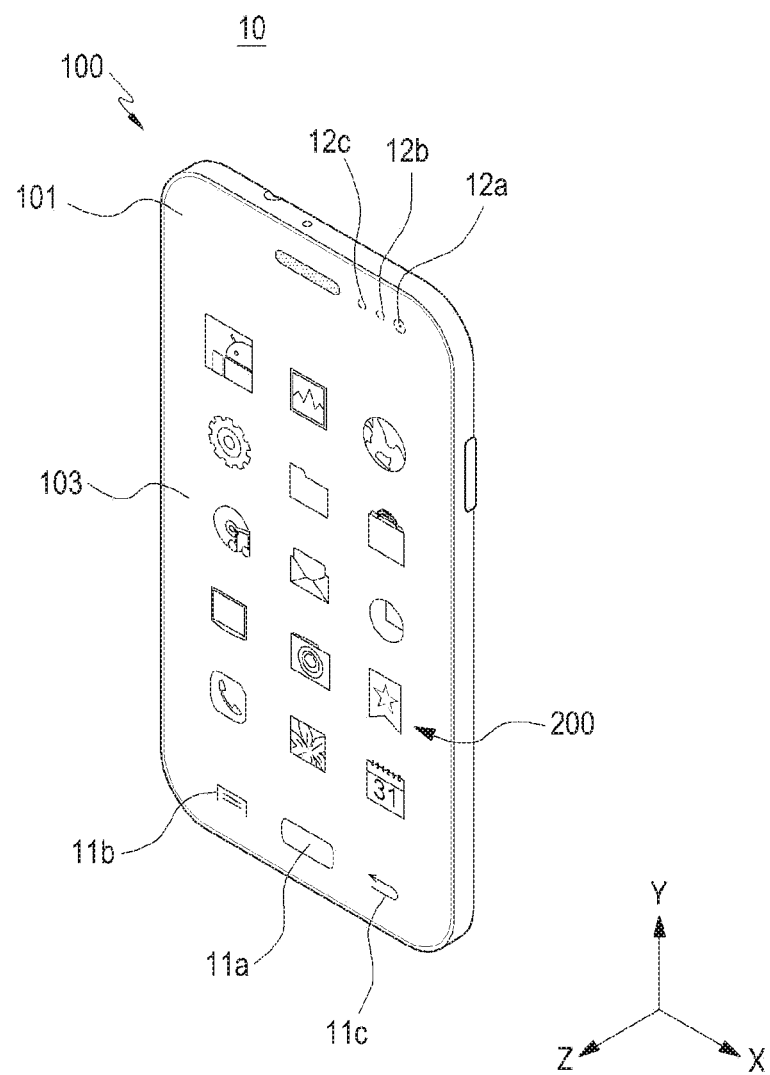
FIGS. 2A and 2B are perspective views each illustrating an electronic device including a display device, according to an embodiment of the present disclosure.
Figure 2B:
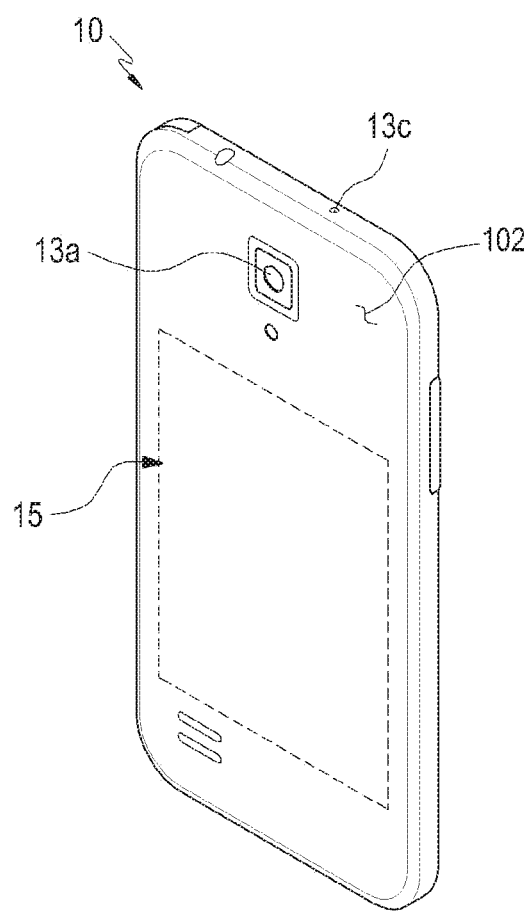

FIGS. 2A and 2B are perspective views each illustrating an electronic device including a display device, according to an embodiment of the present disclosure.

FIG. 2A is a perspective view illustrating an electronic device 10 that includes a display device 200 according to an embodiment of the present disclosure. In FIG. 2A, an "X-axis" in an orthogonal coordinate system of three axes may correspond to the width direction of the electronic device 10, a "Y-axis" may correspond to the length direction of the electronic device 10, and a "Z-axis" may correspond to the thickness direction of the electronic device 100.

As illustrated in FIGS. 2A and 2B, the electronic device 10 includes a housing 100 and a display device 200. The housing 100 includes a first face 101 facing a first (+Z) direction and a second face 102 facing a second (−Z) direction that is opposite to the first (+Z) direction. The front face of the housing 100 may be opened and a transparent cover 103 may be mounted to form at least a portion of the first face 101 so as to close the opened front face of the housing 100. Substantially the entire area of the transparent cover 103 (e.g., the entire area excluding an inactive area extending from 0.1 mm to 5 mm from at least one boundary of the transparent cover 103) may overlap with the display device 200. When viewed from a position above the transparent cover 103, the display device 200 may be positioned over the entire front face of the electronic device 10. According to an embodiment of the present disclosure, a keypad including mechanically operated buttons or touch keys 11a, 11b, are 11c may be provided on the electronic device 10 (e.g., one side region of the transparent cover 103 on the front face of the housing 100). The touch key may generate an input signal by a user's body contact. The keypad may be implemented with only mechanical buttons, or with only touch keys or both. Various types of circuit devices, such as the processor 120, the memory 130, the input/output interface 150, and the communication interface 170, which are described above, may be accommodated in the housing 100, and a battery 15 may be accommodated in the housing 100 for a power source.

According to an embodiment of the present disclosure, a first camera 12a, an illuminance sensor 12b, or a proximity sensor 12c may be arranged in the upper region of the front face of the electronic device 10. A second camera 13a, a flash 13b, or a speaker 13c may be arranged on the rear face of the electronic device 10. When the display device 200 is disposed over the entire front face of the electronic device 10, the first camera 12a, the illuminance sensor 12b, or the proximity sensor 12c may be integrated within the display device 200, or may be disposed on the rear face of the display device 200.

Figure 2C:
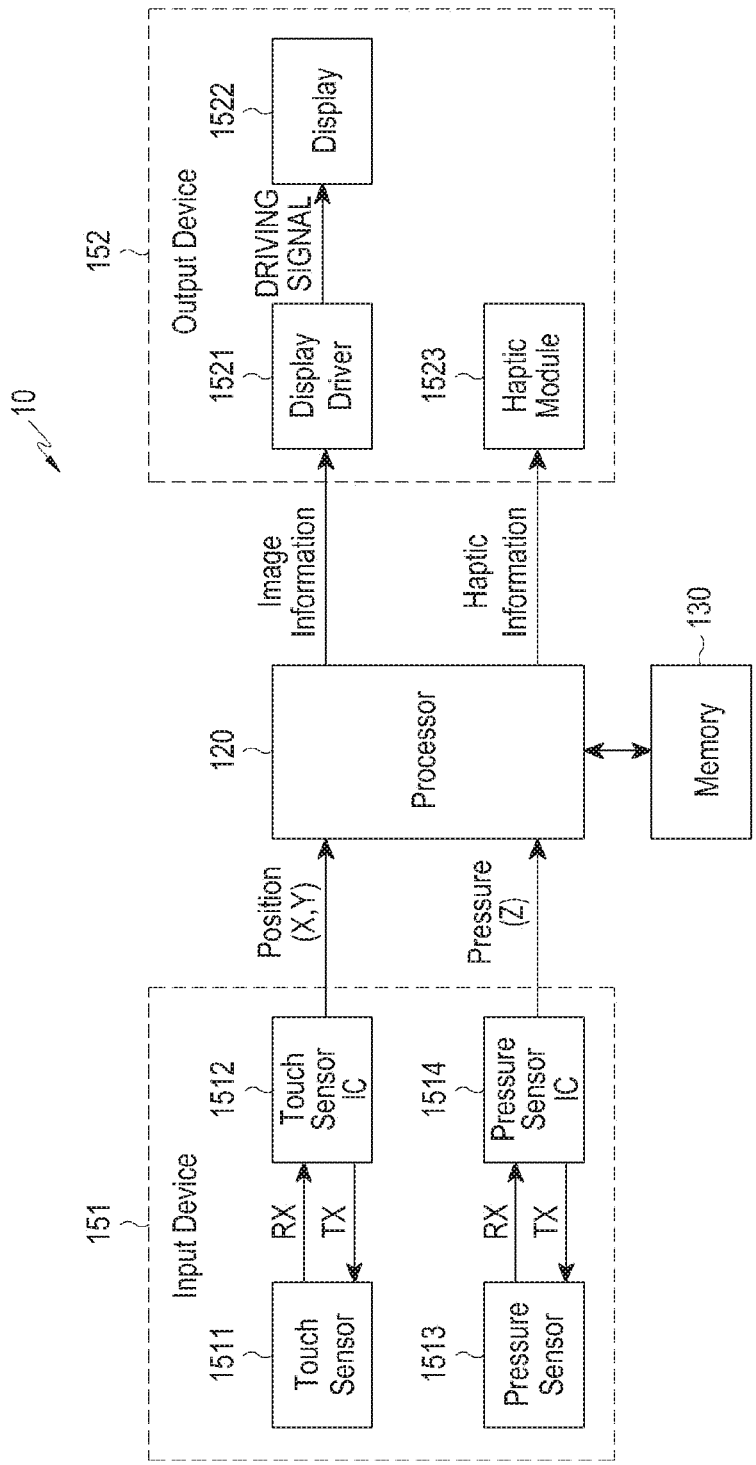
FIG. 2C is a block diagram of an electronic device, according to an embodiment of the present disclosure.

FIG. 2C is a block diagram of an electronic device according to an embodiment of the present disclosure.

Referring to FIG. 2C, according to an embodiment of the present disclosure, the electronic device 10 includes a processor 120, an input device 151, a memory 130, and an output device 152. In addition, the electronic device 10 may further include a communication module.

According to an embodiment of the present disclosure, the output device 152 of the electronic device 10 includes a display panel 1522, a display driver 1521, and a haptic module 1523, and the input device 151 may include a touch sensor 1511, a touch sensor IC 1512, a pressure sensor 1513, and a pressure sensor IC 1514. Redundant descriptions of components, which have been described with reference to FIG. 1, may be omitted.

According to an embodiment of the present disclosure, the display 1522 may receive an image driving signal supplied from the display driver 1521. The display 1522 may display various content and/or items (e.g., a text, an image (object), a video, an icon, a functional object, or a symbol) based on the image driving signal. The display 1522 may be coupled to the touch sensor 1511 and/or the pressure sensor 1513 to overlap therewith, or may be simply referred to as a "display panel." The display 1522 may be driven in a low power mode.

According to an embodiment of the present disclosure, the display driver 1521 may supply the display driving signal corresponding to the image information received from the processor 120 to the display 1522 at a predetermined frame rate. The display driver 1521 may drive the display 1522 in a low power mode. The display driver 1521 may include a graphic RAM, an interface module, an image processing unit, a multiplexer, a display timing controller (T-con), a source driver, a gate driver, and/or an oscillator.

According to an embodiment of the present disclosure, a physical quantity (e.g., voltage, light quantity, resistance, charge quantity, or capacitance) designated by a touch from the user may be measured by the touch sensor 1511. The touch sensor 1511 may be disposed to overlap with the display 1522.

According to an embodiment of the present disclosure, the touch sensor IC 1512 may sense a change in the physical quantity (e.g., voltage, resistance, or capacitance) in the touch sensor 1511, and may calculate the touched position (X, Y) based on the change in the physical quantity. The calculated position (coordinates) may be provided (or reported) to the processor 120. When a user's body part (e.g., a finger), an electronic pen and the like touches the cover glass (e.g., the transparent cover 103 in FIG. 2A) of the display, the coupling voltage between a transmission terminal Tx and a reception terminal Rx included in the touch sensor 1511 may be changed. The change in the coupling voltage may be sensed by the touch sensor IC 1512, and the touch sensor IC 1512 may deliver the coordinates (X, Y) of the touched position to the processor 120. The processor 120 may acquire data regarding the coordinates (X, Y) as an event related to the user input.

According to an embodiment of the present disclosure, the touch sensor IC 1512 may be referred to as a touch IC, a touch screen IC, a touch controller, a touch screen controller IC, and the like. In an electronic device that does not include the touch sensor IC 1512, the processor 120 may perform the function of the touch sensor IC 1512. The touch sensor IC 1512 and the processor 120 may be implemented in a single configuration (e.g., one-chip).

According to an embodiment of the present disclosure, in the pressure sensor 1513, pressure (or force) applied by an external object (e.g., a finger, an electronic pen) may be sensed. In the pressure sensor 1513, the physical quantity (e.g., electrostatic capacity) between the transmission terminal Tx and the reception terminal Rx may be changed by a touch.

According to an embodiment of the present disclosure, the pressure sensor IC 1514 may sense a change in a physical quantity (e.g., capacitance) in the pressure sensor 1513, and may calculate the pressure (Z) applied by the user's touch based on the change in the physical quantity. The pressure sensor IC 1514 may calculate the change of intensity of pressure which is changed in a unit time by the pressure sensor 1513, the direction in which the pressure is applied, and the like. The pressure sensor IC 1514 may provide the processor 120 with a pressure (Z), intensity of pressure, a velocity, a direction, and a touched position (X, Y).

According to an embodiment of the present disclosure, the pressure sensor IC 1514 may be referred to as a force touch controller, a force sensor IC, a pressure panel IC, and the like. The pressure sensor IC 1514 may be implemented in a single configuration (e.g., one-chip) with the touch sensor IC 1512.

According to an embodiment of the present disclosure a haptic module (e.g., a haptic actuator) 1523 may provide tactile feedback (e.g., vibration) to a user in accordance with a control command of the processor 120. The haptic module 1523 may provide tactile feedback to the user when a touch input (including, e.g., a touch, a hover, or a force touch) is received from the user. The haptic module 1523 may provide different kinds of tactile feedback, for example, depending on the intensity of the pressure received from the user.

According to an embodiment of the present disclosure, the memory 130 may store instructions or data associated with an operation of a component included in the electronic device 10. The memory 130 may store at least one application program including a user interface set to display a plurality of items on a display. The memory 130 may store instructions that, when executed, cause the processor 120 to perform various operations described herein.

According to an embodiment of the present disclosure, the processor 120 may be electrically connected to, for example, components 411-414 and 421-423 included in the electronic device 10 and may perform operations or data processing related to the control and/or communication of the components 411-414 and 421-423.

According to an embodiment of the present disclosure, the processor 120 may launch (or execute) an application program (application) that displays a user interface on the display 1522. The processor 120 may display an array of a plurality of items in a user interface displayed on the display 1522 in response to the launching of the application.

According to an embodiment of the present disclosure, the processor 120 may receive the first data (data including the position coordinates (X, Y) of a touch) generated from the touch sensor 1511, and may receive second data (data including the pressure Z of the touch) from the pressure sensor 1513.

According to an embodiment of the present disclosure, the processor 120 may activate at least a portion of the pressure sensor 1513 while the display 1522 is turned off. Alternatively, the processor 120 may at least partially activate the pressure sensor 1513 while the display 1522 is turned off. The processor 120 may activate the entire or a part of the pressure sensor 1513 not only in a case where the electronic device 10 is in an awake state, but also in a case where the electronic device 10 is in a standby state in which the components, such as the display 1522, are turned off. The processor 120 may at least partially deactivate the touch sensor 1511 while the display 1522 is turned off or while the electronic device 10 is in the standby state. Alternatively, the processor 120 may at least partially deactivate the touch sensor 1511 to reduce power consumption in the standby state and to prevent malfunction by a touch.

According to an embodiment of the present disclosure, the processor 120 may activate at least a portion of the pressure sensor 1513 when a designated condition is met while the display 1522 is turned off. The processor 120 may activate the pressure sensor 1513 from a designated time after the display 1522 is turned off or until a designated time. The processor 120 may activate the pressure sensor 1513 when the user's movement of the electronic device 10 is sensed by a gyro sensor or a proximity sensor. The processor 120 may activate the pressure sensor 1513 for a designated time when the temperature is below a designated value, when the electronic device 10 is close to another external device, or when a stylus pen mounted in the electronic device 10 is taken out of the electronic device 10. The processor 120 may activate the pressure sensor 1513 while an application (e.g., a music player) performing an operation in the standby state is executed.

According to an embodiment of the present disclosure, the processor 120 may deactivate at least a portion of the pressure sensor 1513 when a designated condition is met while the display 1522 is turned off. The processor 120 may deactivate the pressure sensor 1513 by using a proximity sensor, an ambient light sensor, an acceleration sensor, and/or a gyro sensor when the electronic device 10 is placed in a pocket, introduced into a bag, or inverted. The processor 120 may deactivate the pressure sensor 1513 when the electronic device 10 is connected to an external device (e.g., when connected to a desktop).

According to an embodiment of the present disclosure, the processor 120 may activate only a designated region of the pressure sensors 1513 while the display 1522 is turned off. The processor 120 may activate a designated portion of the pressure sensor 1513 (e.g., the central lower end region of the pressure sensor 1513) to reduce power consumption in the standby state. Alternatively, when the pressure sensor 1513 is implemented by a group of two or more sensors, the processor 120 may activate some of the two or more sensors.

According to an embodiment of the present disclosure, the processor 120 may activate or enable the pressure sensor 1513 so as to sense pressure using the pressure sensor 1513 while the electronic device 10 is in the standby state. The processor 120 may receive data relating to pressure applied by an external object to the display 1522 from the pressure sensor 1513 while the display 1522 is turned off.

According to an embodiment of the present disclosure, the processor 120 may determine whether the pressure is greater than or equal to a selected level based on the data associated with the pressure, and when it is determined that the pressure is greater than or equal to the selected level, the processor 120 may perform a function without fully turning on the display 1522. The processor 120 may perform a function when pressure greater than a designated level is sensed. In this case, the processor 120 may turn on a portion of the display 1522. The processor 120 may determine a function to perform based on at least one of a pressure-sensed position, the intensity, the number of points, the velocity, the direction, and the duration of the pressure. When the pressure is sensed at a position corresponding to the center of the lower end of the display 1522, the processor 120 may wake up the electronic device 10. When the pressure is sensed at a position corresponding to the upper left end of the display 1522, the processor 120 may control the volume of the speaker of the electronic device 10. When the pressure is sensed at a position adjacent to hardware, such as an ear jack or USB port, the processor 120 may perform a function associated with the adjacent hardware. When the pressure of the designated intensity or higher is sensed, the processor 120 may control the electronic device 10 to enter an emergency mode. The processor 120 may perform different functions depending on the number of points at which the pressure is simultaneously detected.

FIG. 2C illustrates a case where the pressure sensor 1513 provides data for pressure (Z) to the processor 120. However, without being limited thereto, when the pressure sensor 1513 is implemented as a group of two or more sensors, the processor 120 may sense the position where pressure is applied based on the position of a sensor whose capacitance is changed, among the two or more sensors. When the pressure sensor 1513 is implemented as a group of six sensors arranged in a 3×2 array, the processor 120 may determine a position where the pressure is applied based on the changed amount of the capacitance of each of the six sensors and the positions where the six sensors are disposed, respectively. That is, the processor 120 may determine the position where the pressure is applied without using the touch sensor 1511. When the pressure is sensed by the pressure sensor 1513, the processor 120 may activate the touch sensor 1511 so as to sense a position where the pressure is applied using the touch sensor 1511.

According to an embodiment of the present disclosure, when pressure of a first level, which is applied by the touch, is sensed by the pressure sensor 1513, the processor 120 may perform a first function. The processor 120 may determine the first function based on at least one of a position where the pressure of the first level is sensed, intensity, a number of points, a velocity, an orientation, or a duration of the pressure of the first level, and may perform the determined first function. The first function may be to provide tactile feedback of first intensity through the haptic module 1523. The first function may be to display a pop-up type menu associated with an icon displayed in an area of the display 1522 where the pressure is applied. The pressure of the first level may be a mean pressure having intensity within a designated range.

According to an embodiment of the present disclosure, when pressure of a second level, which is applied by the touch, is sensed by the pressure sensor 1513 during the execution of the first function, the processor 120 may perform a second function associated with the first function. The processor 120 may determine the second function based on at least one of a position where the pressure of the second level is sensed, intensity, a number of points, a velocity, an orientation, or a duration of the pressure of the first level. The pressure of the second level may mean pressure having intensity within a designated range. The intensity of the pressure of the second level may be greater or less than the intensity of the pressure of the first level. In addition, the intensity of the second level of pressure may be the same as the intensity of the pressure of the first level. The second function may be to provide tactile feedback of the second intensity greater than the first intensity through the haptic module 1523. The second function may be to display the entire screen associated with an icon displayed in the region to which the pressure is applied in the display 1522. When pressure is sensed during execution of the first function, the processor 120 may execute various functions according to the pressure that is a one-dimensional input by performing the second function associated with the first function that is being performed. In addition, input convenience may be increased by executing, after a single touch on the electronic device 10, other functions associated with the function that is being performed depending on the magnitude of the pressure with which the electronic device 10 is pressed.

According to an embodiment of the present disclosure, in distinguishing a long press input and a pressure input from each other, the electronic device 10 may use values measured by one or more sensors (e.g., an acceleration sensor, and a gyro sensor). Further, the electronic device 10 may use a fingerprint, a camera image, or an iris scan in distinguishing the long press input and the pressure input from each other.

The operations of the processor 120 are described above by way of an example, and are not limited to the above description. The operation of the processor described in other sections of this document may also be understood as the operation of the processor 120. Also, in this disclosure, at least some of the operations described as the operations of an electronic device may also be understood as the operations of the processor 120.

An electronic device, according to an embodiment of the present disclosure, includes a housing including a first face that faces a first direction and a second face that faces a second direction opposite to the first direction, a display disposed between the first face and the second face and exposed through the first face, a pressure sensor disposed between the first face and the second face and configured to detect at least one level and/or position of pressure applied by an external object, at least one processor electrically connected to the display and the pressure sensor, and a memory electrically connected to the processor and configured to store at least one application program. The processor is configured to display a user interface including at least one item on the display, sense an input for selecting the at least one item through the display, determine whether pressure intensity of the sensed input is greater than a first threshold value, and recognize the sensed input as a pressure input when the pressure intensity per frame changes.

According to an embodiment of the present disclosure, the processor is configured to recognize the sensed input as a pressure input and execute the function when the pressure intensity per frame is not changed and the sensed pressure intensity is greater than a second threshold value.

According to an embodiment of the present disclosure, the processor is configured to recognize the sensed input as a pressure input and execute a corresponding function when the sensed touch is not maintained for a predetermined length of time.

According to an embodiment of the present disclosure, the processor is configured to recognize the sensed input as a long press input and execute a corresponding function when the sensed touch is maintained for a predetermined length of time.

According to an embodiment of the present disclosure, the processor is configured to recognize the sensed input as a touch input and execute a corresponding function when the sensed pressure intensity is not greater than the first threshold value.

According to an embodiment of the present disclosure, the processor is configured to measure the pressure intensity of the input during a predetermined frame from a time at which the pressure intensity is greater than the first threshold value.

According to an embodiment of the present disclosure, the processor is configured to sense the pressure input when the pressure intensity per frame increases or decreases at a predetermined rate from a time at which the pressure intensity is greater than the first threshold value.

According to an embodiment of the present disclosure, the processor is configured to sense the pressure input as a long press when the pressure intensity per frame does not increase or decrease at a predetermined rate from a time at which the pressure intensity is greater than the first threshold value.

According to an embodiment of the present disclosure, the processor is configured to recognize the sensed input as a pressure input when the intensity of the sensed pressure is greater than the second threshold.

According to an embodiment of the present disclosure, the processor is configured to determine a time when the pressure intensity becomes greater than the second threshold value as a pressure input start time when the pressure intensity of the sensed input is greater than the first threshold value and becomes greater than the second threshold value within a predetermined length of time.

Figure 3:
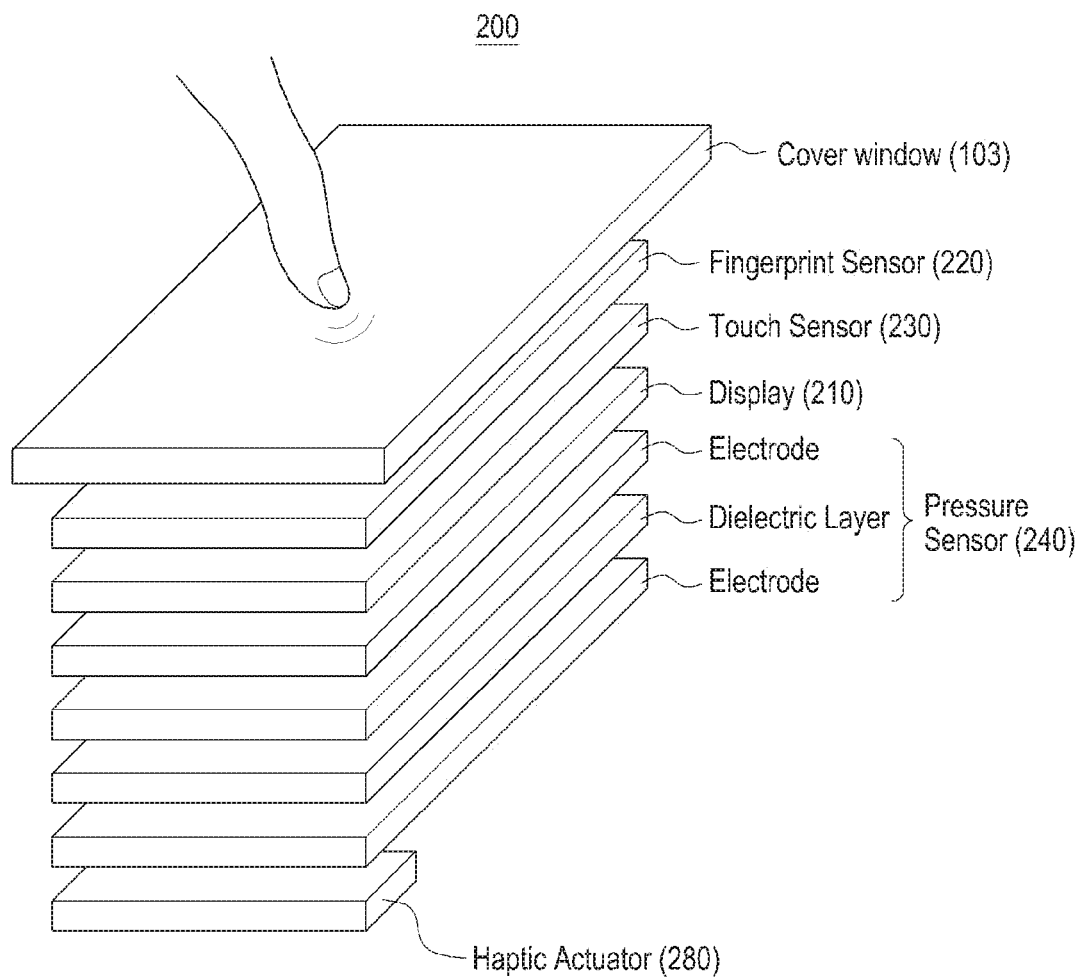
FIG. 3 illustrates a configuration of an end face of a display device, according to an embodiment of the present disclosure.

FIG. 3 illustrates a configuration of an end face of a display device 200 according to an embodiment of the present disclosure.

FIG. 3 is an illustration of the embodiment of FIGS. 4 to 10 to be described below. A display device 200 includes a display 210 that outputs a screen and at least one sensor stacked above or below the display 210. The at least one sensor may be any one of a fingerprint sensor 220, a touch sensor 230, and a pressure sensor 240.

As illustrated in FIGS. 2 and 3, the display 210 may be disposed between the first face 101 and the second face 102 of the housing 100, and may be exposed through the transparent cover 103. The fingerprint sensor 220 may be disposed between the transparent cover 103 and the display 210, and the touch sensor 230 may be disposed between the fingerprint sensor 220 and the display 210. The pressure sensor 240 may be disposed between the display 210 and the second face 102 of the housing 100. The display device 200 may implement various user input (e.g., three-dimensional input) through a combination of the one or more sensors 220, 230 and 240.

According to an embodiment of the present disclosure, in the electronic device 10, the transparent cover 103 may be positioned on the front face of the housing 100 to protect the display 210 from the external environment. The display 210 includes the fingerprint sensor 220, the touch sensor 230, or the pressure sensor 240 in the form of a panel incorporated in the display 210 so that the display 210 may be used not only as an output device, but also as an input device.

According to an embodiment of the present disclosure, a haptic actuator 280 may be disposed below the fingerprint sensor 220, the touch sensor 230, and/or the pressure sensor 240. The haptic actuator 280 may provide haptic feedback (e.g., vibration) to the user when a touch (including a hover and/or a "force touch") by an external object (e.g., a user's finger or an electronic pen) is received. For this purpose, the haptic actuator 280 may include a piezoelectric member and/or a diaphragm.

Figure 4:
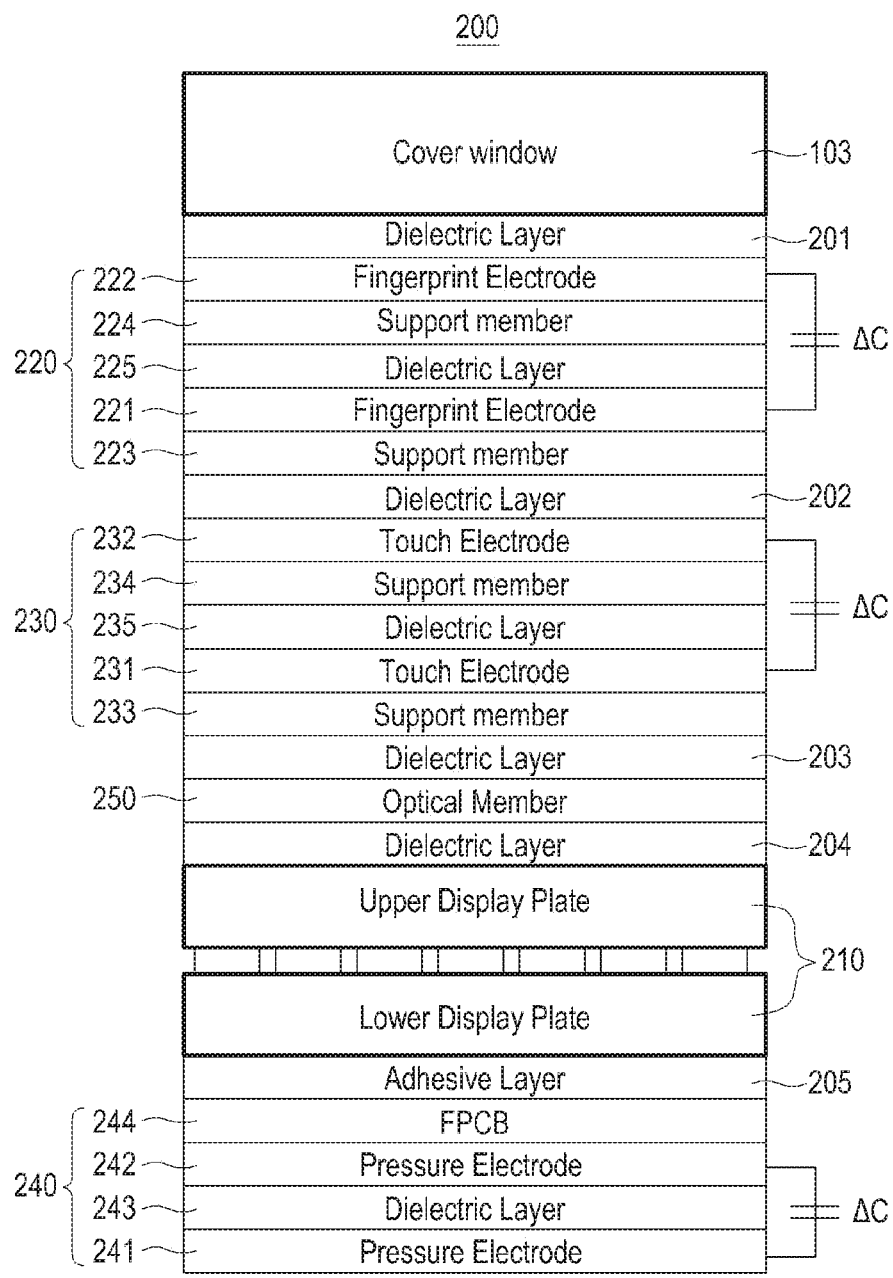
FIGS. 4 to 9 are cross-sectional views each illustrating stacked faces of a display device based on the embodiment of FIG. 3, according to an embodiment of the present disclosure.

FIG. 4 is a cross-sectional view illustrating stacked faces of the display device 200, based on the embodiment of FIG. 3, according to an embodiment of the present disclosure.

As illustrated in FIG. 4, the fingerprint sensor 220 may be stacked to include two fingerprint electrodes 221 and 222, support members 223 and 224, and a dielectric layer 225. Almost the entire area of the fingerprint sensor 220 may overlap with the display 210 when viewed from above the transparent cover 103. Almost the entire area of the fingerprint sensor 220 may overlap with the touch sensor 230 and/or the pressure sensor 240. The support members 223 and 224 are disposed between the transparent cover 103 and the display 210 and may form at least one electrode on the face that faces the first (+Z) direction. The support members 223 and 224 may be a polymer film such as polyethylene terephthalate (PET) or a glass substrate.

According to an embodiment of the present disclosure, the support members may include a first support member 223 and a second support member 224. A first fingerprint electrode 221 may be disposed on the face of the first support member 223, which faces the first (+Z) direction, and a second fingerprint electrode 222 may be disposed on the face of the second support member 224, which faces the first (+Z) direction. The first support member 223 on which the first fingerprint electrode 221 is disposed and the second support member 224 on which the second fingerprint electrode 222 is disposed may be stacked on each other, and a dielectric layer 225 may be disposed therebetween. The dielectric layer 225 may be formed of, for example, silicon, air, foam, membrane, OCA (optically clear adhesive), sponge, rubber, ink, or polymer (e.g., polycarbonate (PC) or PET).

According to an embodiment of the present disclosure, in the cross-section of the fingerprint sensor 220, the stacked layers may be sequentially set forth as the second fingerprint electrode 222, the second support member 224, the dielectric layer 225, the first fingerprint electrode 221, and the first support member 223 from the top side. The first fingerprint electrode 221 and the second fingerprint electrode 222 may be electrically connected to each other to function as the fingerprint sensor 220. Another dielectric layer 202 may be disposed on or below the fingerprint sensor 220 such that the fingerprint sensor 220 faces another sensor. When the fingerprint sensor 220 is disposed below the transparent cover 103, a dielectric layer 201 may be included between the transparent cover 103 and the fingerprint sensor 220.

According to an embodiment of the present disclosure, at least one of the first fingerprint electrode 221 and the second fingerprint electrode 222 may include a transparent conductive material. At least one of the first fingerprint electrode 221 and the second fingerprint electrode 222 may include at least one of indium-tin-oxide (ITO), indium-zinc-oxide (IZO), poly (3,4-ethylenedioxythiophene) (PEDOT) polystyrene sulfonate, a silver (Ag) nanowire, a transparent polymer conductor, and graphene.

According to an embodiment of the present disclosure, at least one of the first fingerprint electrode 221 and the second fingerprint electrode 222 may be arranged in a mesh shape. At least one of the first electrode 221 and the second electrode 222 may be arranged in a mesh shape by sub-electrodes that cross each other.

According to an embodiment of the present disclosure, at least one of the first fingerprint electrode 221 and the second fingerprint electrode 222 may be connected to a wiring electrode disposed on a non-effective region. The wiring electrode may be connected to at least one control circuit. The control circuit is electrically connected to the first fingerprint electrode 221 and/or the second fingerprint electrode 222, and may sense the fingerprint of the user's finger that is in contact with the first face of the housing using the first fingerprint electrode 221 and/or the second fingerprint electrode 222. The at least one control circuit may apply a transmission signal to the first fingerprint electrode 221 and/or the second fingerprint electrode 222, and may receive a reception signal corresponding to the transmission signal through at least another one of the first fingerprint electrode 221 and the second fingerprint electrode 222.

According to an embodiment of the present disclosure, the touch sensor 230 may be stacked to include two touch electrodes 231 and 232, support members 233 and 234, and a dielectric layer 235. Almost the entire area of the touch sensor 230 may overlap with the display 210 when viewed from a position above the transparent cover 103. Almost the entire area of the touch sensor 230 may have an area corresponding to the fingerprint sensor 220. At least one of the support members 233 and 234 may be disposed between the transparent cover 103 and the display 210. At least one electrode may be formed on a face that faces the first (+Z) direction. The support members 233 and 234 may be a polymer film such as PET or a glass substrate. The support members 233 and 234 may include a third support member 233 and a fourth support member 224 each having at least one electrode disposed on the top face thereof.

According to an embodiment of the present disclosure, a first fingerprint electrode 231 may be disposed on the face of the third support member 233, which faces the first (+Z) direction, and a second fingerprint electrode 232 may be disposed on the face of the fourth support member 234, which faces the first (+Z) direction. The third support member 233 on which the first touch electrode 231 is disposed and the fourth support member 234 on which the second touch electrode 232 is disposed may be stacked on each other, and a dielectric layer 235 may be disposed therebetween. The dielectric layer 235 may be formed of, for example, silicon, air, foam, membrane, OCA, sponge, rubber, ink, or polymer (e.g., PC or PET).

According to an embodiment of the present disclosure, in the cross-section of the touch sensor 230, the stacked layers may be sequentially set forth as the second touch electrode 232, the fourth support member 234, the dielectric layer 235, the first fingerprint electrode 231, and the third support member 233 from the top side. The first touch electrode 231 and the second touch electrode 232 may be electrically connected to each other to function as a touch sensor.

According to an embodiment of the present disclosure, at least one of the first touch electrode 231 and the second touch electrode 232 may include a transparent conductive material. At least one of the first touch electrode 231 and the second touch electrode 232 may include at least one of ITO, IZO, PEDOT, an Ag nanowire, a transparent polymer conductor, and graphene.

According to an embodiment of the present disclosure, at least one of the first touch electrode 231 and the second touch electrode 232 may be arranged in a mesh shape. At least one of the first touch electrode 231 and the second touch electrode 232 may be arranged in a mesh shape by sub-electrodes that cross each other.

According to an embodiment of the present disclosure, the touch sensor 230 may be disposed below the fingerprint sensor 220 to face the fingerprint sensor 220, and a dielectric layer 202 may be disposed between the touch sensor 230 and the fingerprint sensor 220. In another example, an optical member 250 may be disposed below the touch sensor 230.

According to an embodiment of the present disclosure, the optical member 250 transmits therethrough a screen output from the display 210, and at least one optical member 250 may be stacked on the display 210. Thus, the optical member 250 may be directly attached to the display 210, or may be adhered to another optical member on the display 210. The optical member 250 may include an optical compensation film and the like for correcting a phase difference and the like of a screen output from the display 210.

According to an embodiment of the present disclosure, the optical member 250 may include an optical compensation film (e.g., a polarizing film). In the optical compensation film, tri-acetyl cellulose (TAC) films are respectively attached to the opposite surfaces of a polyvinyl alcohol (PVA) film, which provides a polarizing function, and the surface side TAC film may be protected by a surface coating layer.

According to an embodiment of the present disclosure, at least one of the first touch electrode 231 and the second touch electrode 232 may be connected to a wiring electrode disposed on a non-effective region. The wiring electrode may be connected to at least one control circuit. The control circuit is electrically connected to the first touch electrode 231 and/or the second touch electrode 232, and may sense a touch position of the user's finger that is in contact with the first face 101 using the first touch electrode 231 and/or the second touch electrode 232. The at least one control circuit may apply a transmission signal to the first touch electrode 231 and/or the second touch electrode 232, and may receive a reception signal corresponding to the transmission signal through at least another one of the first touch electrode 231 and the second touch electrode 232.

According to an embodiment of the present disclosure, the touch sensor 230 may be attached to the front face of the display 210 (the face on which an image output from the display is displayed) or attached to or formed on the inner face of the transparent cover 103. The touch sensor 230 may be implemented as a capacitive-type touch panel made of an ITO film. The touch sensor 230 may be implemented as a resistive touch panel. The touch sensor 230 described above may detect a change in capacitance when the user's body touches or approaches the touch sensor 230 so as to detect plane (x,y) coordinates of a point that the user touches (or approaches). Here, the plane coordinates may refer to coordinates indicating a position on the front face of the display 210.

Such touch inputs may include various gestures as well as simply touching or approaching a specific location. Various types of touch inputs may be performed that include, Touch, which is an input action of placing a finger on the screen, tap, which is an input action of touching the screen shortly and lightly (e.g., double tap, triple tap, and quadruple tap), flick, which is an input action of placing a finger on the screen, moving the finger quickly, and then separating the finger, drag, which is an input action of moving or scrolling a screen element, drag and drop, which is an input action of moving a screen element in a touch state and then separating the finger from the screen in a stopped state, swipe, which is an input action of moving a finger over a predetermined distance in one direction in a state where two, three or more fingers touch a screen, multi swipe, which is an input action of two, three, or more fingers by a predetermined distance in a state where the fingers touch the screen, pinch that is an input action of moving two fingers in different directions in a state where the fingers touch the screen, touch and hold, which is an input action of maintaining a touch state until a screen element appears, and shake, which is an input action of shaking the device so as to operate an action.

According to an embodiment of the present disclosure, the pressure sensor 240 may be stacked to include two electrodes 241 and 242 and a dielectric layer 243. Almost the entire area of the pressure sensor 240 may overlap with the display 210 when viewed from a position above the transparent cover 103. Almost the entire area of the pressure sensor 240 may have an area corresponding to the fingerprint sensor 220 and/or the touch sensor 230.

According to an embodiment of the present disclosure, the pressure sensor 240 may be disposed below the display 210 to face the display 210, and may be bonded to the display 210 through an adhesive layer 205. A second pressure electrode 242 and a first pressure electrode 241 may be disposed above and below the pressure sensor 240, and a dielectric layer 243 may be disposed therebetween. The dielectric layer 243 may be formed of, for example, silicon, air, foam, membrane, OCA, sponge, rubber, ink, or polymer (e.g., PC or PET).

According to an embodiment of the present disclosure, in the cross-section of the pressure sensor 240, the stacked layers may be sequentially set forth as the printed circuit board 244, the second electrode 242, the dielectric layer 243, and the first pressure electrode 241 from the top side. The first pressure electrode 241 and the second pressure electrode 242 may be electrically connected to each other to function as the pressure sensor 240.

According to an embodiment of the present disclosure, at least one of the first pressure electrode 241 and the second pressure electrode 242 may include a transparent conductive material. At least one of the first pressure electrode 241 and the second pressure electrode 242 may include at least one of ITO, IZO, PEDOT, an Ag nanowire, a transparent polymer conductor, and graphene.

According to an embodiment of the present disclosure, at least one of the first pressure electrode 241 and the second pressure electrode 242 may be arranged in a mesh shape. At least one of the first pressure electrode 241 and the second pressure electrode 242 may be arranged in a mesh shape by sub-electrodes that cross each other.

According to an embodiment of the present disclosure, the pressure sensor 240 may be disposed to face the bottom face of the printed circuit board, and the printed circuit board may include a flexible printed circuit board. However, without being limited thereto, the second pressure electrode 242 may be formed directly below the printed circuit board.

According to an embodiment of the present disclosure, at least one of the first pressure electrode 241 and the second pressure electrode 242 may be connected to a wiring electrode disposed on a non-effective region. The wiring electrode may be connected to at least one control circuit. The control circuit is electrically connected to the first pressure electrode 241 and/or the second pressure electrode 242, and may sense the pressure of the user's finger that is in contact with the transparent cover using the first pressure electrode 241 and/or the second pressure electrode 242. The at least one control circuit may apply a transmission signal to the first pressure electrode 241 and/or the second pressure electrode 242, and may receive a reception signal corresponding to the transmission signal through at least another one of the first pressure electrode 241 and the second pressure electrode 242.

According to an embodiment of the present disclosure, the pressure sensor 240 may be attached to or formed on the rear face of the display 210. The pressure sensor 240 may be implemented as a capacitive touch panel made of an ITO film. According to an embodiment of the present disclosure, the pressure sensor 240 may be implemented as a resistive touch panel.

According to an embodiment of the present disclosure, when the user's body and the like approaches or touches the display 210, the pressure sensor 240 changes the capacitance between the pressure electrodes 241 and 242, and the pressure sensor 240 may detect such a change in capacitance. The change in capacitance depends on an approaching distance to the display 210 or a touch pressure on the display 210. The approaching distance to the display 210 or the touch pressure on the display 210 may be calculated from the change in capacitance so as to acquire a vertical coordinate for one face of the display 210.

According to an embodiment of the present disclosure, the display device 200 has a pressure sensor 240 configured with one panel disposed on the entire back face of the display 210 or a pressure sensor 240 configured with an arrangement of a plurality of panels.

According to an embodiment of the present disclosure, the display device 200 may calculate the approaching distance of the user's body to the display device 200 or the touch pressure on the display device 200 from a change in capacitance or a change in resistance value detected from the pressure sensor 240, and may also calculate a digital value (e.g., a vertical coordinate) for the display 210 from this pressure. Three-dimensional coordinates may be acquired by combining the digital value calculated as described above and the plane coordinate (x,y) detected through the touch sensor, and may provide a new user experience by implementing the three-dimensional touch input through the display device 210 using the three-dimensional coordinates.

According to an embodiment of the present disclosure, the pressure sensor 240 may be implemented as a capacitive type. When the touch sensor 230 is implemented as a capacitive-type touch panel, it is possible to control the pressure sensor 240 or to process data and the like detected from the pressure sensor 240 using a control circuit chip of the touch panel or a touch key.

According to an embodiment of the present disclosure, the display device 200 may include, in a region overlapping with the display 210, a fingerprint sensor 220, a touch sensor 230, and/or a pressure sensor 240 which are arranged to be stacked, so that programs for which the user's recognition is required may be variously applied and used, and a three-dimensional touch input may be implemented. In addition, since it is possible to control the fingerprint sensor 220, the touch sensor 230, and/or the pressure sensor 240 by using a single control circuit chip and to process recognition, coordinates, and the like detected from each of the sensors, a time delay or a time difference may be improved. Further, since there is no need to set an additional algorithm for synchronization, it is possible to better control the electronic device while diversifying the user experience provided through the electronic device.

Figure 5:
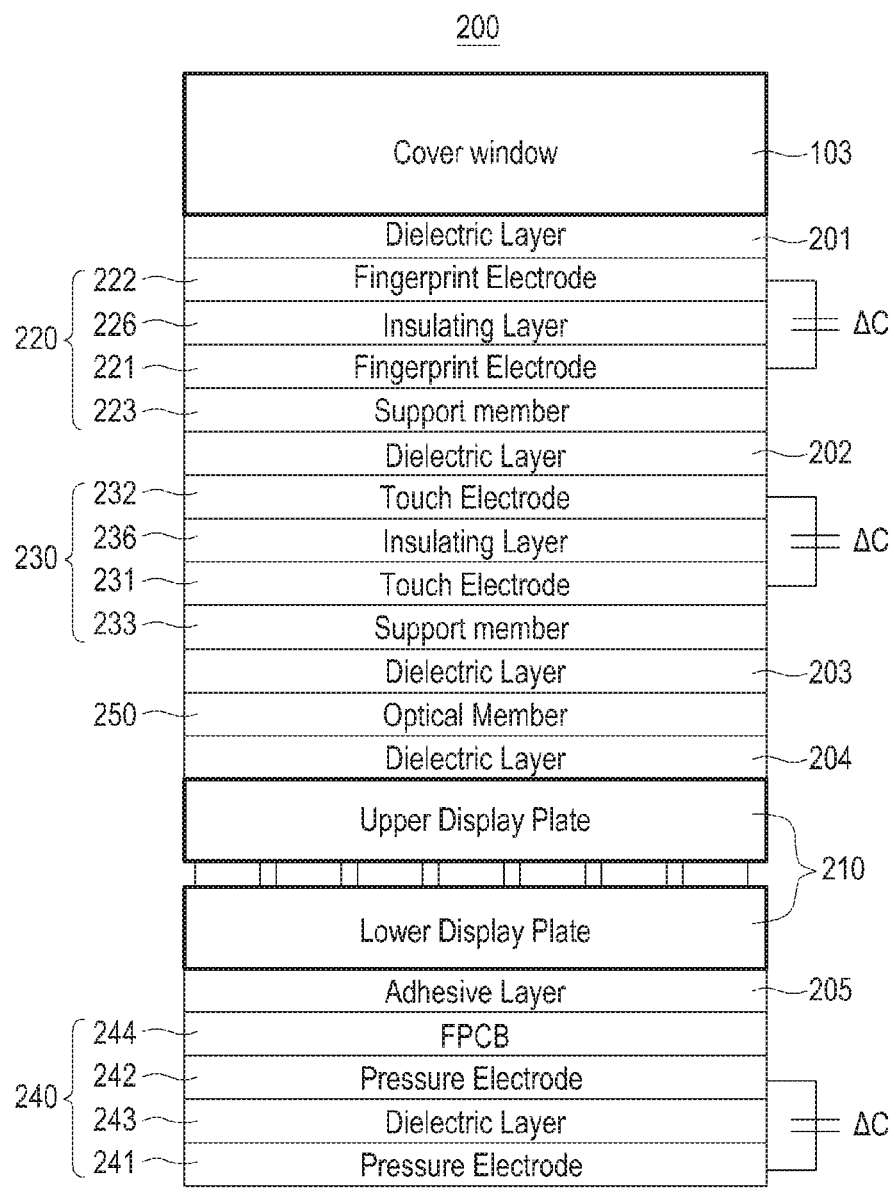

FIG. 5 is a cross-sectional view illustrating stacked faces of the display device 200, according to an embodiment of the present disclosure, based on the embodiment of FIG. 3. The descriptions of components in the display device 200 of FIG. 5, which are similar to those of the embodiment of FIG. 4 will be omitted, and the differences will be mainly described.

As illustrated in FIG. 5, the fingerprint sensor 220 may be stacked to include two electrodes 221 and 222, a support member 223, and an insulating layer 226. Almost the entire area of the fingerprint sensor 220 may overlap with the display 210 when viewed from a point above the transparent cover 103. Almost the entire area of the fingerprint sensor 220 may overlap with the touch sensor 230 and/or the pressure sensor 240.

According to an embodiment of the present disclosure, a first fingerprint electrode 221 and a second fingerprint electrode 222 may be disposed on the face of the first support member 223, which faces the first (+Z) direction, and an insulating layer 226 may be disposed between the first fingerprint electrode 221 and the second fingerprint electrode 222. The first fingerprint electrode 221 may be an X-axis electrode portion formed in one direction (the X-axis direction), and the second fingerprint electrode 222 may be a Y-axis electrode portion formed in a direction crossing the X-axis electrode portion (the Y-axis direction). The first fingerprint electrode 221 and the second fingerprint electrode 222 are folded together and a fingerprint may be sensed through a changed value at the position where the first fingerprint electrode 221 and the second fingerprint electrode 222 intersect.

According to an embodiment of the present disclosure, the first fingerprint electrode 221 formed in the X axis direction and the second fingerprint electrode 222 formed in the Y axis direction, which crosses the first fingerprint electrode 221 in the other direction, may be disposed with the insulating layer 226 being interposed therebetween such that the first fingerprint electrode 221 and the second fingerprint electrode 222 are disposed on the opposite faces of the insulating layer 226. When the first fingerprint electrode 221 is formed, a pattern capable of electrically connecting an intersection point of connection ports may also be formed on the first fingerprint electrode 221, and an insulating member may also be formed on the insulating layer to insulate the intersection point of the connection ports.

According to an embodiment of the present disclosure, in the cross-section of the fingerprint sensor 220, the stacked layers may be sequentially set forth as the second fingerprint electrode 222, the insulating layer 226, the first fingerprint electrode 221, and the first support member 223 from the top side. The first fingerprint electrode 221 and the second fingerprint electrode 222 may be electrically connected to each other to function as the fingerprint sensor 220. Dielectric layers 201 and 202 may be disposed on or below the fingerprint sensor 220 such that the fingerprint sensor 220 is disposed to face other sensors. When the fingerprint sensor 220 is disposed below the transparent cover 103, a dielectric layer 201 may be included between the transparent cover 103 and the fingerprint sensor 220.

According to an embodiment of the present disclosure, at least one of the first fingerprint electrode 221 and the second fingerprint electrode 222 may include a transparent conductive material.

According to an embodiment of the present disclosure, the first fingerprint electrode 221 and the second fingerprint electrode 222 may be formed in the same layer, and may be connected to each other by a bridge type electrode in the case where the first fingerprint electrode 221 and the second fingerprint electrode 222 are formed in the same layer.

According to an embodiment of the present disclosure, the touch sensor 230 may be stacked to include two electrodes 231 and 232, support members 233 and 234, and an insulating layer 236. Almost the entire area of the touch sensor 230 may overlap with the display 210 when viewed from a position above the transparent cover 103. Almost the entire area of the touch sensor 230 may have an area corresponding to the fingerprint sensor 220.

According to an embodiment of the present disclosure, a first touch electrode 231 and a second touch electrode 232 may be disposed on the face of the third support member 233, which faces the first (+Z) direction, and the insulating layer 236 may be disposed between the first touch electrode 231 and the second touch electrode 232. The first touch electrode 231 may be an X-axis electrode portion formed in one direction (the X-axis direction), and the second touch electrode 232 may be a Y-axis electrode portion formed in a direction crossing the X-axis electrode portion (the Y-axis direction). The first touch electrode 231 and the second touch electrode 232 are folded together and a finger touch position may be sensed through a changed value at the position where the first touch electrode 231 and the second touch electrode 232 intersect.

According to an embodiment of the present disclosure, the first touch electrode 231 formed in the X axis direction and the second touch electrode 232 formed in the Y axis direction, which crosses the first touch electrode 231 in the other direction, may be disposed with the insulating layer 236 being interposed therebetween such that the first touch electrode 231 and the second touch electrode 232 are disposed on the opposite faces of the insulating layer 236. When the first touch electrode 231 is formed, a pattern capable of electrically connecting an intersection point of connection ports may also be formed on the first touch electrode 231, and an insulating member may also be formed on the insulating layer to insulate the intersection point of the connection ports.

According to an embodiment of the present disclosure, in the cross-section of the touch sensor 230, the stacked layers may be sequentially set forth as the second touch electrode 232, the insulating layer 236, the first touch electrode 231, and the third support member 233 from the top side. The first touch electrode 231 and the second touch electrode 232 may be electrically connected to each other to function as a touch sensor 230. Dielectric layers 202 and 203 may be disposed on or below the touch sensor 230 such that the touch sensor 230 is disposed to face other sensors. When the touch sensor 230 is disposed above the optical member 250, a dielectric layer 203 may be included between the touch sensor 230 and the optical member 250.

According to an embodiment of the present disclosure, the first touch electrode 231 and the second touch electrode 232 may be formed in the same layer, and may be connected to each other by a bridge electrode in the case where the first touch electrode 231 and the second touch electrode 232 are formed in the same layer.

Figure 6:
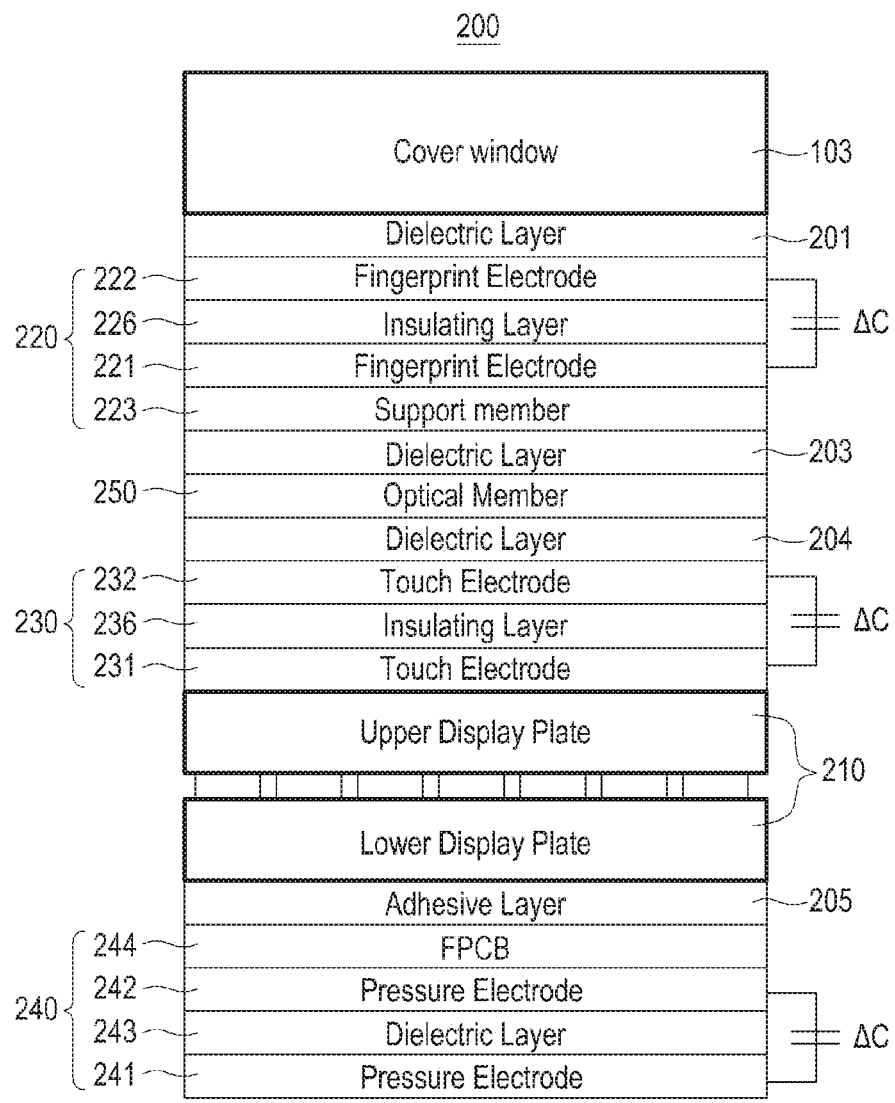

FIG. 6 is a cross-sectional view illustrating stacked faces of the display device 200 based on the embodiment of FIG. 3, according to an embodiment of the present disclosure. The descriptions of components in the display device 200 of FIG. 6, which are similar to those of the embodiment of FIG. 4 will be omitted, and the differences will be mainly described.

As illustrated in FIG. 6, the fingerprint sensor 220 may be stacked to include two electrodes 221 and 222, a support member 223, and an insulating layer 226. Almost the entire area of the fingerprint sensor 220 may overlap with the display 210 when viewed from a point above the transparent cover 103. Almost the entire area of the fingerprint sensor 220 may overlap with the touch sensor 230 and/or the pressure sensor 240.

According to an embodiment of the present disclosure, in the cross-section of the fingerprint sensor 220, the stacked layers may be sequentially set forth as the second fingerprint electrode 222, the insulating layer 226, the first fingerprint electrode 221, and the support member 223 from the top side. The first fingerprint electrode 221 and the second fingerprint electrode 222 may be electrically connected to each other to function as the fingerprint sensor 220. Dielectric layers 201 and 203 may be disposed on or below the fingerprint sensor 220 such that the fingerprint sensor 220 is disposed to face other sensors. When an optical member 250 is disposed below the fingerprint sensor 220, a dielectric layer 203 may be included between the fingerprint sensor 220 and the optical member 250.

According to an embodiment of the present disclosure, the touch sensor 230 may be stacked to include two electrodes 231 and 232 and an insulating layer 236. Almost the entire area of the touch sensor 230 may overlap with the display 210 when viewed from a position above the transparent cover 103. Almost the entire area of the touch sensor 230 may have an area corresponding to the fingerprint sensor 220.

According to an embodiment of the present disclosure, in the cross-section of the touch sensor 230, the stacked layers may be sequentially set forth as the second touch electrode 231, the insulating layer 236, and the first touch electrode 232 from the top side. The first touch electrode 231 and the second touch electrode 232 may be electrically connected to each other to function as a touch sensor 230. A dielectric layer 204 may be disposed on the touch sensor 230 such that the touch sensor 230 may be disposed to face the optical member 250.

According to an embodiment of the present disclosure, the touch sensor 230 may be directly and integrally formed on the upper face of the display 210, so that the support member under the touch sensor 230 may be removed, which enables manufacturing costs to be considerably reduced and an assembly process to be simplified. In another example, since the touch sensor 230 is formed integrally with the display 210, the optical member 250 may be disposed above the touch sensor 230. Since the fingerprint sensor 220 is disposed above the optical member 250 and the touch sensor 230 is disposed below the optical member 250, dielectric layers 203 and 204 may be included above and below the optical member 250, respectively.

Figure 7:
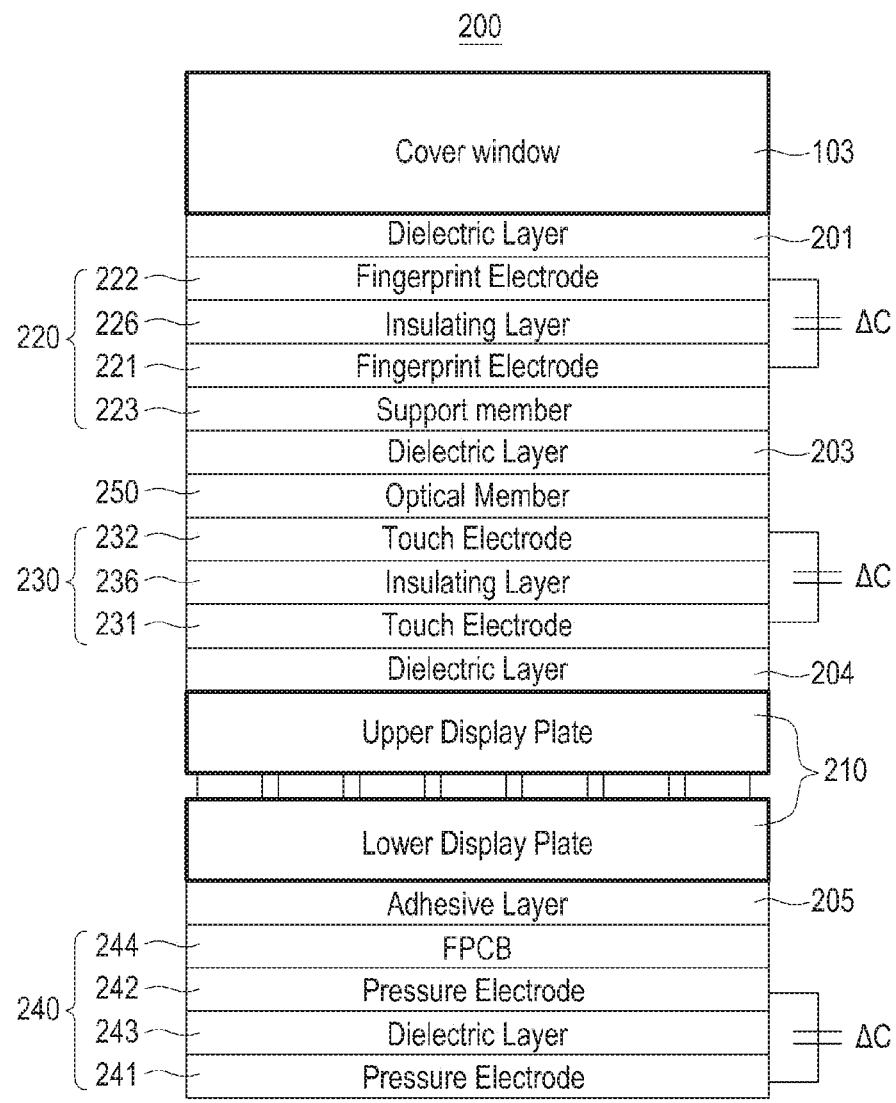

FIG. 7 is a cross-sectional view illustrating stacked faces of the display device 200, according to an embodiment of the present disclosure, based on the embodiment of FIG. 3. The descriptions of components in the display device 200 of FIG. 7, which are similar to those of the embodiment of FIG. 5 will be omitted, and the differences will be mainly described.

As illustrated in FIG. 7, the touch sensor 230 may be stacked to include two electrodes 231 and 232 and an insulating layer 236. In addition, the touch sensor 230 may be formed integrally with the optical member 250.

According to an embodiment of the present disclosure, in the cross-section of the touch sensor 230, the stacked layers may be sequentially set forth as the optical member 250, the second touch electrode 232, the insulating layer 236, and the first touch electrode 231 from the top side. The first touch electrode 231 and the second touch electrode 232 may be electrically connected to each other to function as a touch sensor 230. A dielectric layer 204 may be disposed below the touch sensor 230 such that the touch sensor 230 may be disposed to face the display 210.

According to an embodiment of the present disclosure, the touch sensor 230 is capable of being directly and integrally formed on one face of the optical member 250, so that the dielectric layer above the touch sensor 230 may be removed, which enables manufacturing costs to be reduced and a thin display device 200 to be implemented.

Figure 8:
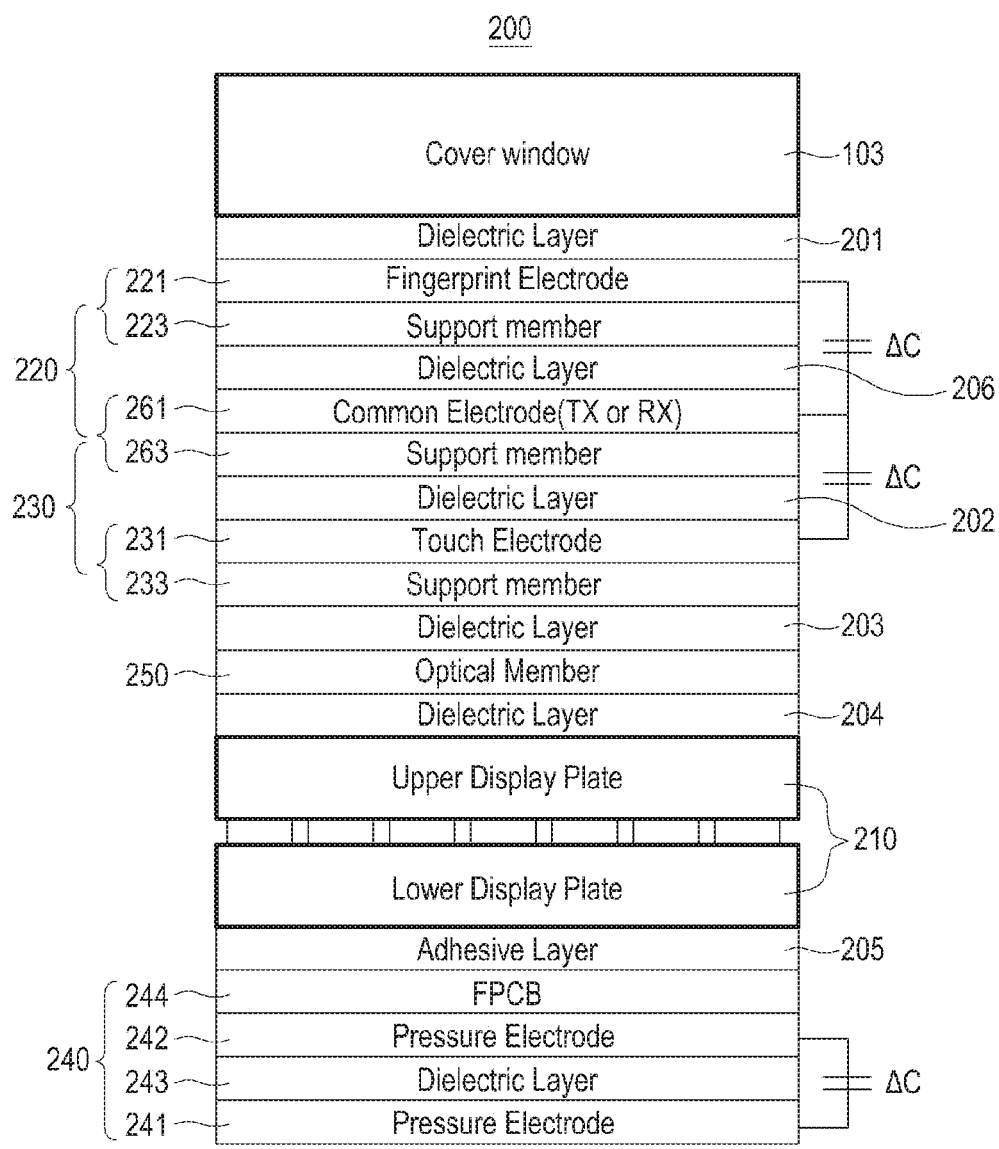

FIG. 8 is a cross-sectional view illustrating stacked faces of the display device 200 based on the embodiment of FIG. 3, according to an embodiment of the present disclosure. The descriptions of components in the display device 200 of FIG. 8, which are similar to those of the embodiment of FIG. 4 will be omitted, and the differences will be mainly described.

As illustrated in FIG. 8, the display device 200 includes a display 210 that outputs a screen and at least one sensor that is stacked on the display 210. The at least one sensor may be any one of a fingerprint sensor 220, a touch sensor 230, and a pressure sensor 240. According to one embodiment, the fingerprint sensor 220 and the touch sensor 230 may include two electrodes, one of which is mutually sharable.

According to an embodiment of the present disclosure, the touch sensor 220 may be stacked to include two electrodes (e.g., a fingerprint electrode 221 and a common electrode 261), support members 233 and 263, and a dielectric layer 206. Almost the entire area of the fingerprint sensor 220 may overlap with the display 210 when viewed from a point above the transparent cover 103. Almost the entire area of the fingerprint sensor 220 may overlap with the touch sensor 230 and/or the pressure sensor 240. The support members 233 and 263 may be a polymer film such as PET or a glass substrate.

According to an embodiment of the present disclosure, the fingerprint electrode 221 may be disposed on the face of the first support member 223, which faces the first (+Z) direction, and the common electrode 261 may be disposed on the face of the second support member 263, which faces the first (+Z) direction. The first support member 223 on which the first fingerprint electrode 221 is disposed and the second support member 263 on which the common electrode 261 is disposed may be stacked on each other, and a dielectric layer 206 may be disposed therebetween.

According to an embodiment of the present disclosure, the touch sensor 230 may be stacked to include two electrodes (e.g., a touch electrode 231 and a common electrode 261), support members 233 and 263, and a dielectric layer 202. Almost the entire area of the touch sensor 230 may overlap with the display 210 when viewed from a position above the transparent cover 103. Almost the entire area of the touch sensor 230 may have an area corresponding to the fingerprint sensor 220.

According to an embodiment of the present disclosure, the touch electrode 231 may be disposed on the face of the third support member 233, which faces the first (+Z) direction, and the common electrode 261 may be disposed on the face of the second support member 263, which faces the first (+Z) direction. The second support member 263 on which the common electrode 261 is disposed and the third support member 233 on which the touch electrode 231 is disposed may be stacked on each other, and a dielectric layer 202 may be disposed therebetween.

According to an embodiment of the present disclosure, the common electrode 261 may sense the user's touch position through an electric connection with the touch electrode 231 to be described later, in addition to sensing the fingerprint of the user's finger through the electrical connection with the finger electrode 221. A transmission signal is applied to the common electrode 261, and a reception signal corresponding to the transmission signal is applied to each of the fingerprint electrode 221 and the touch electrode 231, so that the user's fingerprint and touch position may be sensed. Alternatively, a transmission signal is applied to each of the fingerprint electrode 221 and the touch electrode 231, and a reception signal corresponding to the transmission signal is applied to the common electrode 261, so that the user's fingerprint and touch position may be sensed. In another example, during a first time period, a transmission signal is applied to the fingerprint electrode 221 and a reception signal is applied to the common electrode 261, and during a second time period, a transmission signal is applied to the common electrode 261 and a reception signal is applied to the touch electrode 231, so that the user's fingerprint and touch position may be detected. Alternatively, during the first time period, a transmission signal is applied to the common electrode 261 and a reception signal is applied to the fingerprint electrode 221, and during the second time period, a transmission signal is applied to the touch electrode 231 and a reception signal is applied to the common electrode 261, so that the user's fingerprint and touch position may be detected.

According to an embodiment of the present disclosure, the common electrode 261 is disposed between the fingerprint sensor 220 and the touch sensor 230, and forms a part of the electrodes of the fingerprint sensor 220 and the touch sensor 230, and as a result, the number of support members and electrodes is reduced so that manufacturing costs may be reduced, the assembly process may be simplified, and a thinner display device 200 may be implemented.

According to an embodiment of the present disclosure, the common electrode 261 may form an electrode in different directions from the fingerprint electrode 221 and/or the touch electrode 231. The common electrode 261 may be arranged to intersect the fingerprint electrode 221 and the touch electrode 231. The common electrode 261 may include at least one electrode pattern that extends in one direction, and the fingerprint electrode 221 and the touch electrode 231 may include at least one electrode pattern that extends in a direction different from the direction of the common electrode 261. The common electrode 261 may be an X-axis electrode portion, and the fingerprint electrode 221 and the touch electrode 231 may be Y-axis electrode portions formed in a direction crossing the X-axis electrode portion (i.e., in the Y-axis direction).

Figure 9:
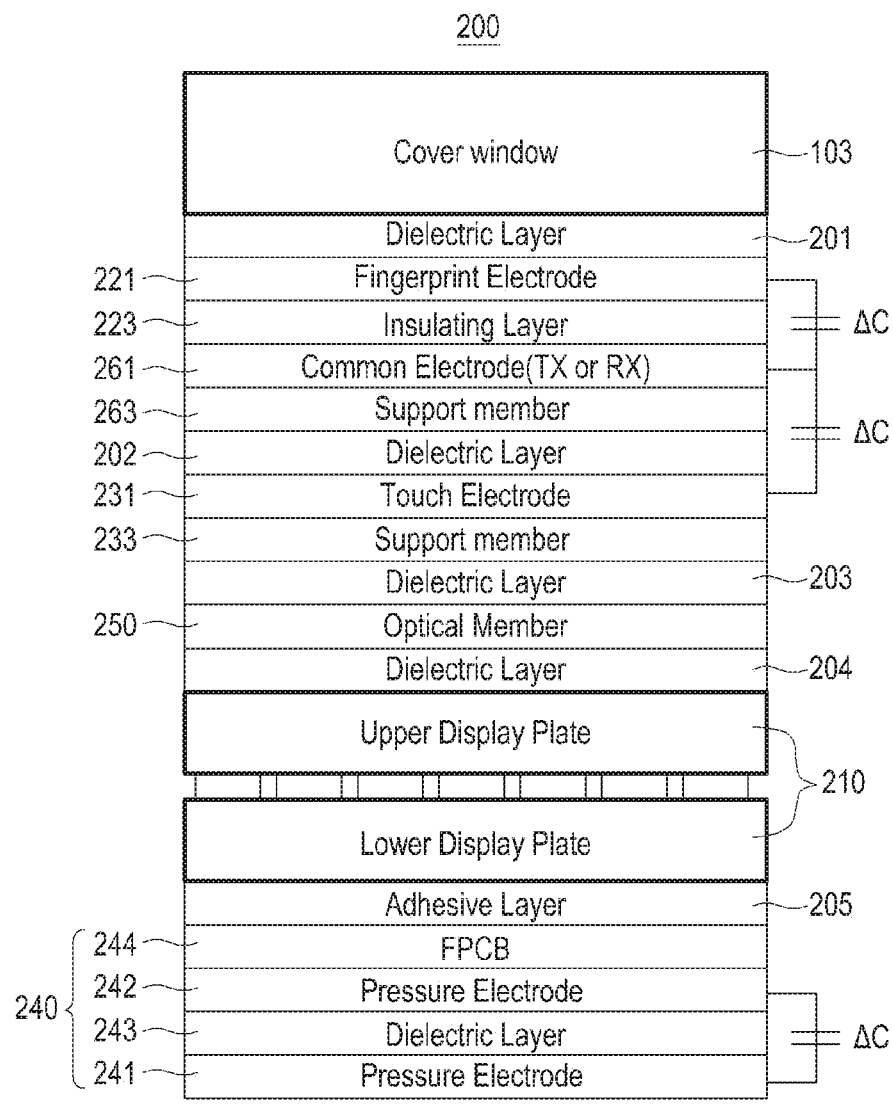

FIG. 9 is a cross-sectional view illustrating stacked faces of the display device 200 based on the embodiment of FIG. 3, according to an embodiment of the present disclosure. The descriptions of components in the display device 200 of FIG. 9, which are similar to those of the embodiment of FIG. 8 will be omitted, and the differences will be mainly described.

The configuration illustrated in FIG. 9 may be implemented such that the fingerprint electrode 221 and the common electrode 261 are disposed on one support member 263 in the stacked structure of FIG. 8 and an insulating layer 223 is included therebetween. According to an embodiment of the present disclosure, the fingerprint electrode 221 and the common electrode 261 may be arranged to face different directions, and the fingerprint electrode 221 and the common electrode 261 may be formed in a pattern in which a plurality of bars are arranged. However, without being limited thereto, the fingerprint electrode 221 and the common electrode 261 may be formed in patterns of various shapes (e.g., a polygonal shape such as a square, a diamond, a pentagon, and a hexagon, or a circle).

According to an embodiment of the present disclosure, The fingerprint electrode 221 may be an X-axis electrode portion formed in one direction (the X-axis direction), and the common electrode 261 may be a Y-axis electrode portion formed in a direction crossing the X-axis electrode portion (the Y-axis direction). The fingerprint electrode 221 and the common electrode 261 are folded together and a fingerprint may be sensed through a changed value at the position where the finger electrode 221 and the common electrode 222 intersect each other.

Figure 10:
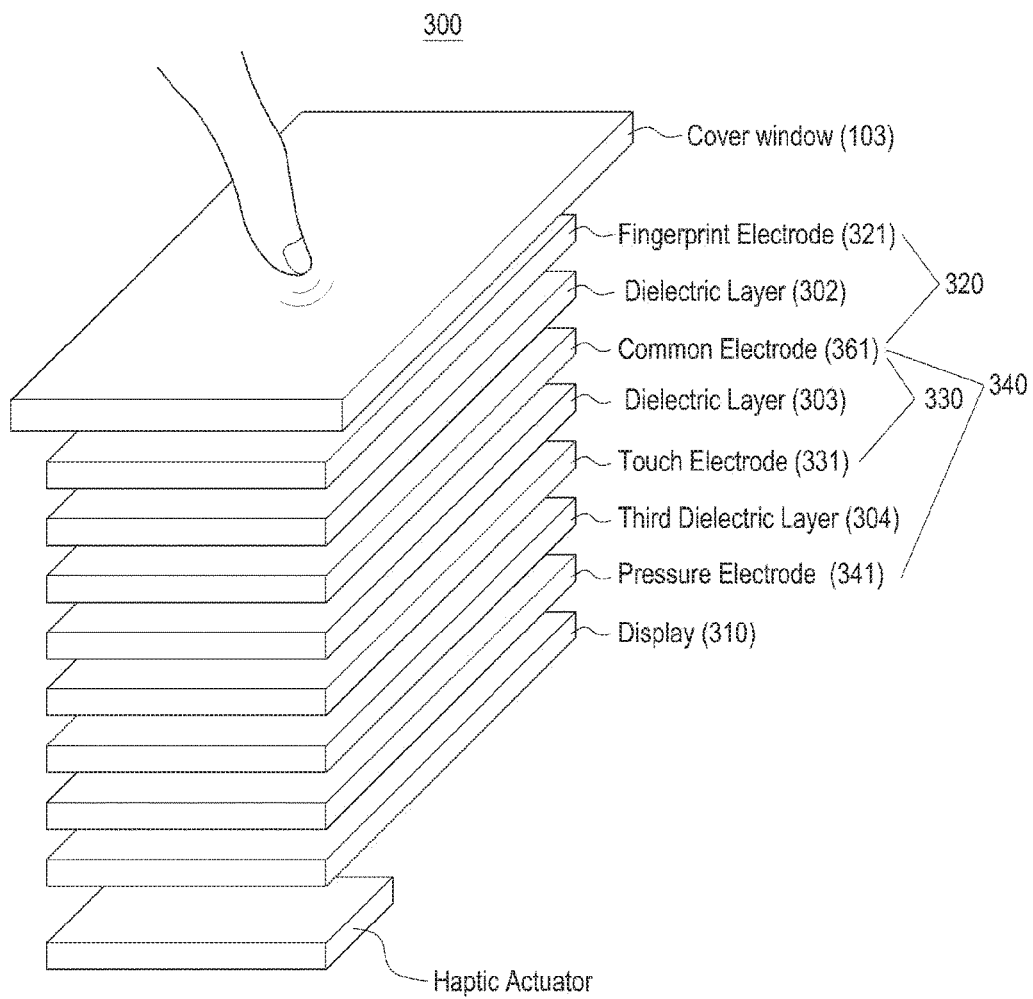
FIG. 10 illustrates a configuration of an end face of a display device, according to another embodiment of the present disclosure.

FIG. 10 illustrates a configuration of an end face of a display device 300 according to an embodiment of the present disclosure.

FIG. 10 is a perspective view of the embodiments of FIGS. 11 to 16. An embodiment of the present disclosure may include at least one sensor above the display unlike the embodiment of FIG. 3. The at least one sensor may be any one of a fingerprint sensor 320, a touch sensor 330, and a pressure sensor 340.

As illustrated in FIGS. 2 and 10, the display 310 may be disposed between the first face 101 and the second face 102 of the housing 100, and may be exposed through the transparent cover 103. The fingerprint sensor 320 may be disposed between the transparent cover 103 and the display 310, and the touch sensor 330 may be disposed between the fingerprint sensor 320 and the display 310. The pressure sensor 340 may be disposed between the touch sensor 330 and the display 310. The display device 300 may implement various user experiences (e.g., three-dimensional input) through a combination of the one or more sensors.

According to an embodiment of the present disclosure, in the electronic device 10, the transparent cover 103 may be positioned on the front face of the housing 100 to protect the display 310 from the external environment. The display 310 includes the fingerprint sensor 320, the touch sensor 330, or the pressure sensor 340 in the form of a panel incorporated in the display 310 so that the display 310 may be used not only as an output device, but also as an input device.

According to an embodiment of the present disclosure, the electronic device 10 is disposed between the transparent cover 103 and the display 310 and includes a common electrode 361 that includes electrodes of the fingerprint sensor 320, the touch sensor 330, and/or the pressure sensor 340.

According to an embodiment of the present disclosure, the electronic device 10 may include at least one control circuit electrically connected to the display 310, the fingerprint electrode 321, the common electrode 361, the touch electrode 331, and the pressure electrode 341. The at least one control circuit may sense the fingerprint of a user's finger that touches the transparent cover 103 using the fingerprint electrode 321 and the common electrode 361. In addition, the at least one control circuit may sense the touch position of the finger using the common electrode 361 and the touch electrode 331. The at least one control circuit may sense the pressure of the finger on the first face 101 using the common electrode 361 and the pressure electrode 341.

Figure 11:
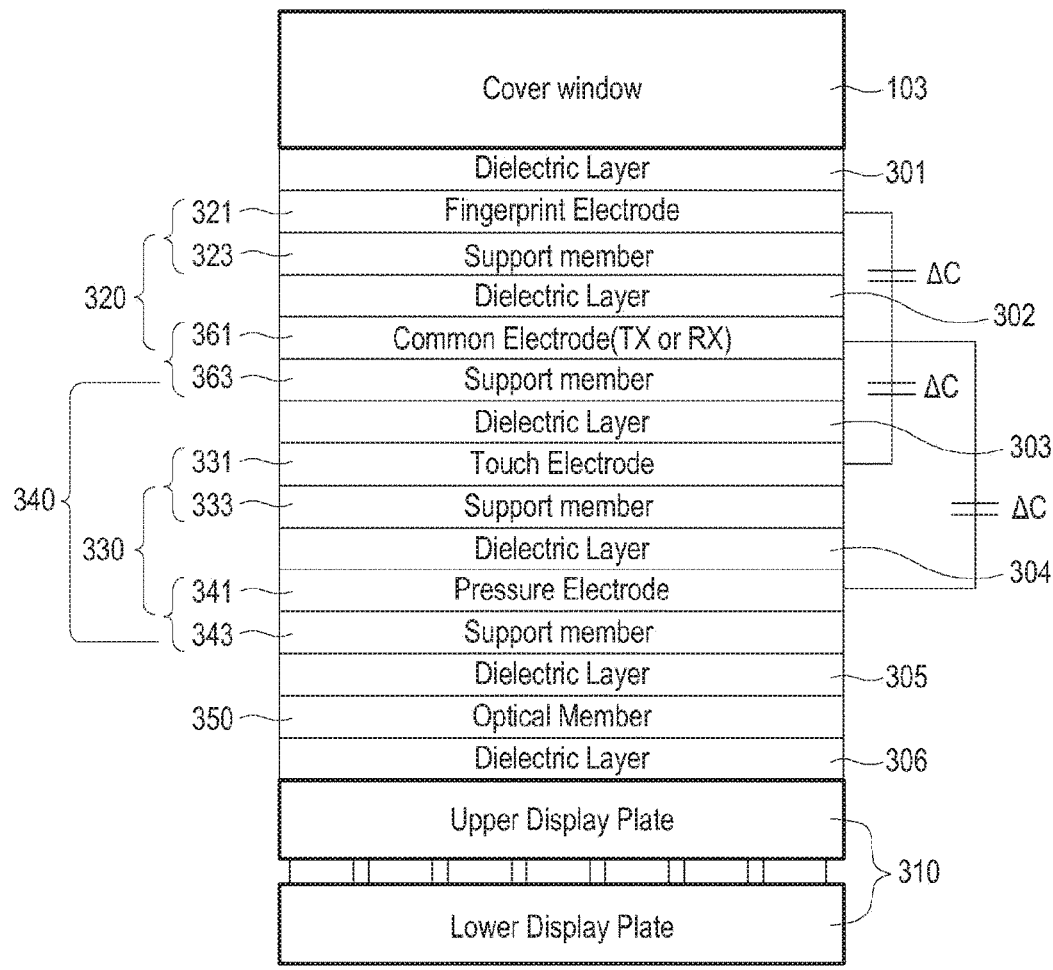
FIGS. 11 to 16 are cross-sectional views each illustrating stacked faces of a display device based on the embodiment of FIG. 10, according to an embodiment of the present disclosure.

FIG. 11 is a cross-sectional view illustrating stacked faces of the display device 300 based on the embodiment of FIG. 10, according to an embodiment of the present disclosure.

As illustrated in FIG. 11, the display device 300 includes a fingerprint sensor 320, a touch sensor 330, and/or a pressure sensor 340, which are formed between the transparent cover 103 and the display 310.

According to an embodiment of the present disclosure, the fingerprint sensor 320 may be stacked to include two electrodes 321 and 361, support members 323 and 363, and a dielectric layer 302. Almost the entire area of the fingerprint sensor 320 may overlap with the display 310 when viewed from a point above the transparent cover 103. Almost the entire area of the fingerprint sensor 320 may overlap with the touch sensor 330 and/or the pressure sensor 340. The support members 323 and 363 are disposed between the transparent cover 103 and the display 310 and may form at least one electrode on the face that faces the first (+Z) direction. The support members 323 and 363 may be a polymer film such as PET or a glass substrate.

According to an embodiment of the present disclosure, the fingerprint sensor 320 may be implemented through an electrical connection between the fingerprint electrode 321 on the first support member 323 and the common electrode 361 on the second support member 363. The fingerprint electrode 321 may be disposed on the face of the first support member 323, which faces the first (+Z) direction, and the common electrode 361 may be disposed on the face of the second support member 363, which faces the first (+Z) direction. The first support member 323 on which the first fingerprint electrode 321 is disposed and the second support member 363 on which the common electrode 361 is disposed may be stacked on each other, and a dielectric layer 302 may be disposed therebetween. The dielectric layer 302 may be formed of, for example, silicon, air, foam, membrane, OCA, sponge, rubber, ink, or polymer (e.g., PC or PET).

According to an embodiment of the present disclosure, the common electrode 361 on the second support member 363 may be electrically connected to the touch electrode 331 and/or the pressure electrode 341 to be described later, in addition to the connection with the fingerprint electrode 321.

According to an embodiment of the present disclosure, the touch sensor 330 may be stacked to include two electrodes 331 and 361, support members 333 and 363, and a dielectric layer 303. Almost the entire area of the touch sensor 330 may overlap with the display 310 when viewed from a position above the transparent cover 103.

According to an embodiment of the present disclosure, the touch sensor 330 may be implemented through an electrical connection between the touch electrode 331 on the third support member 333 and the common electrode 361 on the second support member 363. The fingerprint electrode 331 may be disposed on the face of the third support member 333, which faces the first (+Z) direction, and the common electrode 361 may be disposed on the face of the second support member 363, which faces the first (+Z) direction.

According to an embodiment of the present disclosure, the pressure sensor 340 may be stacked to include two electrodes 331 and 361, support members 343 and 363, and a dielectric layer 304. Almost the entire area of the pressure sensor 340 may overlap with the display 310 when viewed from a position above the transparent cover 103.

According to an embodiment of the present disclosure, the pressure sensor 340 may be implemented through an electrical connection between the pressure electrode 341 on the fourth support member 343 and the common electrode 361 on the second support member 363. The pressure electrode 341 may be disposed on the face of the fourth support member 343, which faces the first (+Z) direction, and the common electrode 361 may be disposed on the face of the second support member 363, which faces the first (+Z) direction.

According to an embodiment of the present disclosure, at least one of the fingerprint electrode 321, the common electrode 361, the touch electrode 331, and the pressure electrode 341 may include a transparent conductive material. At least one of the fingerprint electrode 321, the common electrode 361, the touch electrode 331, and the pressure electrode 341 may include at least one of ITO, IZO, PEDOT, an Ag nanowire, a transparent polymer conductor, and graphene.

According to an embodiment of the present disclosure, a first dielectric layer 302 may be disposed between the fingerprint electrode 321 and the common electrode 361, and a second dielectric layer 303 may be disposed between the common electrode 361 and the touch electrode 331. A third dielectric layer 304 may be disposed between the touch electrode 331 and the pressure electrode 341. The third dielectric layer 304 may at least partially include a material that is different from the first dielectric layer 302 and/or the second dielectric layer 303, and may have a thickness that is greater than those of the first dielectric layer 302 and/or the second dielectric layer 303.

According to an embodiment of the present disclosure, an optical member 350 may be disposed below the touch sensor 330. The optical member 350 transmits therethrough a screen output from the display 310, and at least one optical member 350 may be stacked on the display 310. Thus, the optical member 350 may be directly attached to the display 310, or may be adhered to another optical member on the display 310. The optical member 350 may include an optical compensation film and the like for correcting a phase difference and the like of a screen output from the display 310.

Figure 12:
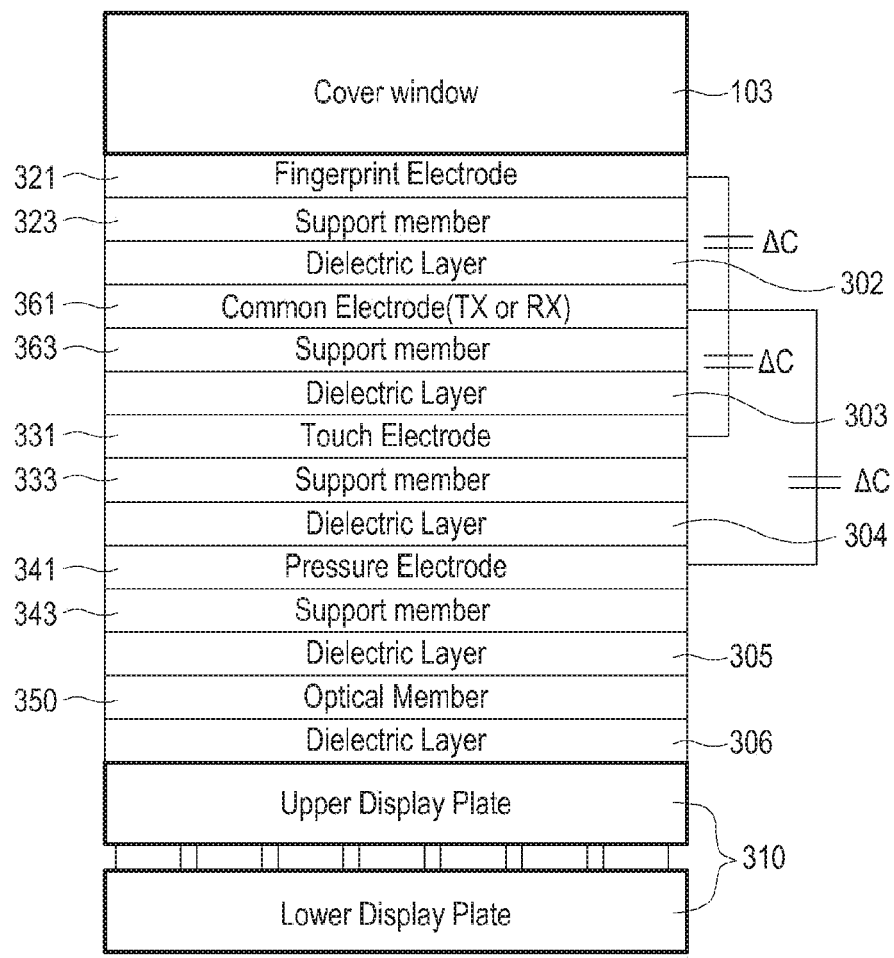

FIG. 12 is a cross-sectional view illustrating stacked faces of the display device 300 based on the embodiment of FIG. 10, according to an embodiment of the present disclosure.

As illustrated in FIG. 12, the display device 300 includes a fingerprint electrode 321, a common electrode 361, a touch electrode 331, and/or a pressure electrode 341, which are formed between the transparent cover 103 and the display 310. The fingerprint electrode 321, the common electrode 361, the touch electrode 331, and the pressure electrode 341 may correspond to the fingerprint electrode 321, the common electrode 361, the touch electrode 331, and the pressure electrode 341 of the above-described embodiment of FIG. 11, respectively.

According to an embodiment of the present disclosure, compared with the above-described embodiment of FIG. 11, the display device 300 may be configured such that the transparent cover 103 and the fingerprint electrode 321 may be integrally formed. The fingerprint electrode 321 may be directly formed on the transparent cover 103 to partially remove the dielectric layer 301 in FIG. 11. Accordingly, the dielectric layer above the fingerprint sensor 320 is removed, which enables manufacturing costs to be reduced and a thinner display device 300 to be implemented.

Figure 13:
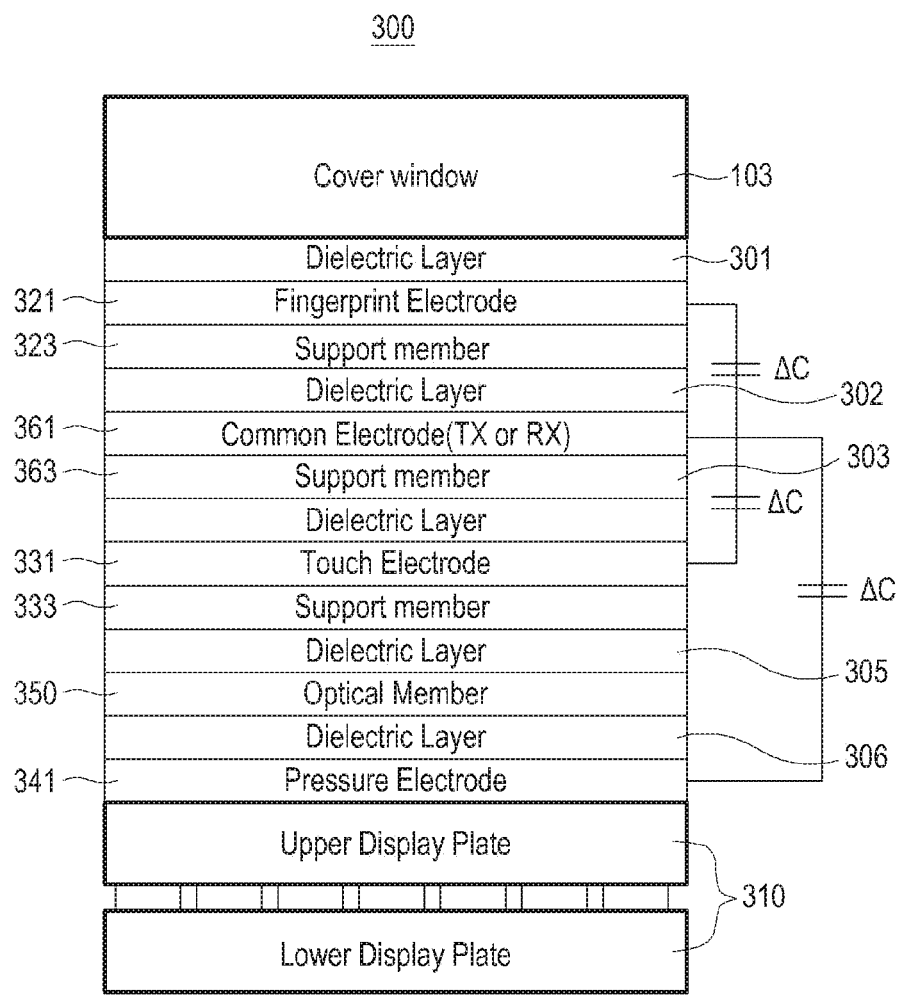

FIG. 13 is a cross-sectional view illustrating stacked faces of the display device 300 based on the embodiment of FIG. 10, according to an embodiment of the present disclosure.

As illustrated in FIG. 13, the display device 300 includes a fingerprint electrode 321, a common electrode 361, a touch electrode 331, and/or a pressure electrode 341, which are formed between the transparent cover 103 and the display 310. The fingerprint electrode 321, the common electrode 361, the touch electrode 331, and the pressure electrode 341 may correspond to the fingerprint electrode 321, the common electrode 361, the touch electrode 331, and the pressure electrode 341 of the above-described embodiment of FIG. 11, respectively.

According to an embodiment of the present disclosure, compared with the above-described embodiment of FIG. 11, the display device 300 may be configured such that the transparent cover 310 and the fingerprint electrode 341 may be integrally formed. The pressure electrode 341 may be formed directly on the display 310 so that a portion of the dielectric layer and the support member disposed in the above-described embodiment of FIG. 11 may be removed. Accordingly, when the display device 300 is implemented, manufacturing costs may be reduced, and the assembly process may be simplified.

Since the touch sensor 340 is formed integrally with the display 310, an optical member 350 may be disposed above the touch sensor 341. Since the touch electrode 331 is disposed above the optical member 350 and the pressure electrode 341 is disposed below the optical member 350, dielectric layers 305 and 306 may be included above and below the optical member 350, respectively.

Figure 14:
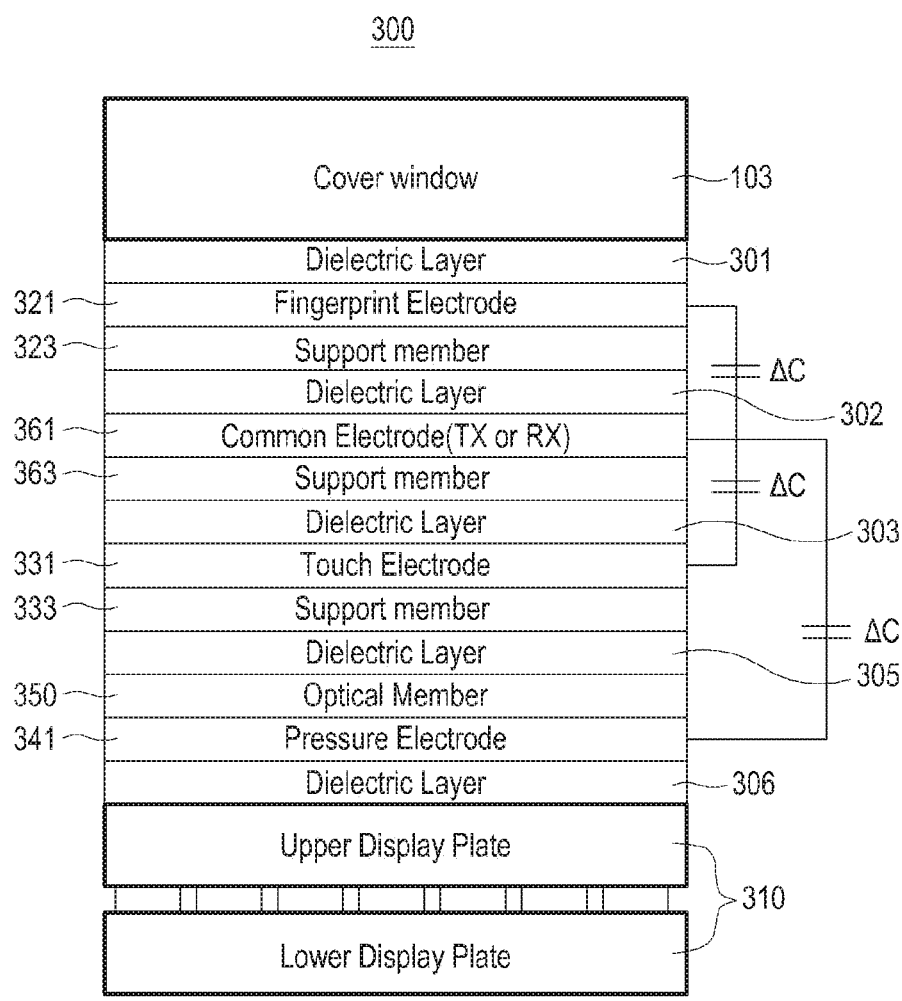

FIG. 14 is a cross-sectional view illustrating stacked faces of the display device 300S based on the embodiment of FIG. 10, according to an embodiment of the present disclosure.

As illustrated in FIG. 14, the display device 300 includes a fingerprint electrode 321, a common electrode 361, a touch electrode 331, and/or a pressure electrode 341, which are formed between the transparent cover 103 and the display 310. The fingerprint electrode 321, the common electrode 361, the touch electrode 331, and the pressure electrode 341 may correspond to the fingerprint electrode 321, the common electrode 361, the touch electrode 331, and the pressure electrode 341 of the above-described embodiment of FIG. 11, respectively.

According to an embodiment of the present disclosure, compared with the above-described embodiment of FIG. 11, the display device 300 may be configured such that the optical member 350 and the pressure electrode 341 are integrally formed. The pressure electrode 341 may be formed directly above or below the optical member 350 so that a portion of the dielectric layer and the support member disposed in the above-described embodiment of FIG. 11 may be removed. Accordingly, when the display device 300 is implemented, manufacturing costs may be reduced, and the assembly process may be simplified.

According to an embodiment of the present disclosure, since the pressure sensor 340 is formed integrally with the optical member 350, the dielectric layers 305 and 306 may be formed above and below the pressure sensor 340 and the optical member 350, respectively.

Figure 15:
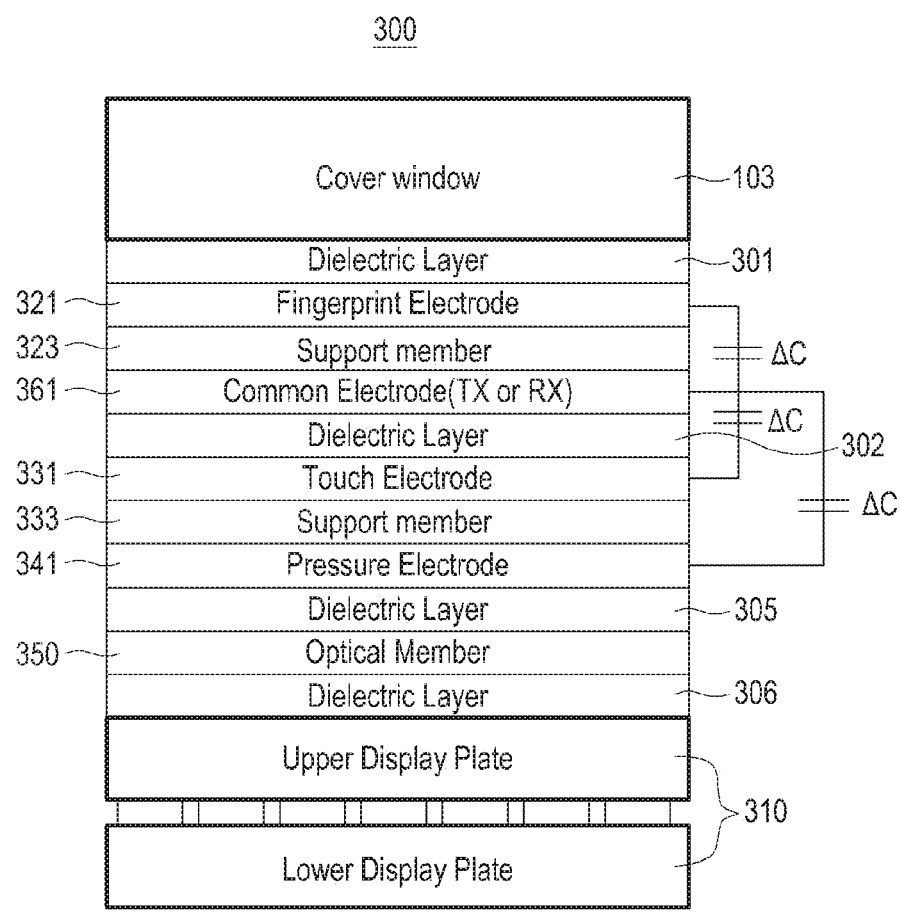

FIG. 15 is a cross-sectional view illustrating stacked faces of the display device 300 based on the embodiment of FIG. 10, according to an embodiment of the present disclosure.

As illustrated in FIG. 15, the display device 300 includes a fingerprint electrode 321, a common electrode 361, a touch electrode 331, and/or a pressure electrode 341, which are formed between the transparent cover 103 and the display 310. The fingerprint electrode 321, the common electrode 361, the touch electrode 331, and the pressure electrode 341 may correspond to the fingerprint electrode 321, the common electrode 361, the touch electrode 331, and the pressure electrode 341 of the above-described embodiment of FIG. 11, respectively.

According to an embodiment of the present disclosure, compared with a case where each electrode according to the above-described embodiment of FIG. 11 is formed on the corresponding separate support member, the display device 300 is configured such that two electrodes may be disposed on one of the support members 323 and 333. For example, separate electrodes may be formed above and below one support member 323 or 333, respectively.

According to an embodiment of the present disclosure, the display device 300 includes a fingerprint electrode 321 formed above the first support member 323 and a common electrode 361 formed below the first support member 323. In addition, the touch electrode 331 may be formed above the third support member 333, and the pressure electrode 341 may be formed below the second support member 333.

According to an embodiment of the present disclosure, in the cross-section of the display device 300, the stacked layers may be sequentially set forth as the fingerprint electrode 321, the first support member 323, the common electrode 361, the dielectric layer 302, the touch electrode 331, the third support member 333, and the pressure electrode 341 from the top side. The common electrode 361 may be electrically connected to the fingerprint electrode 321, the touch electrode 331, and/or the pressure electrode 341 to function as a fingerprint sensor, a touch sensor, and/or a pressure sensor.

According to an embodiment of the present disclosure, two electrodes may be formed on one support member 323 or 333 so that a portion of the dielectric layer and a plurality of support members disposed in the above-described embodiment of FIG. 11 may be removed. Accordingly, when the display device 300 is implemented, manufacturing costs may be reduced, and the assembly process may be simplified.

Figure 16:
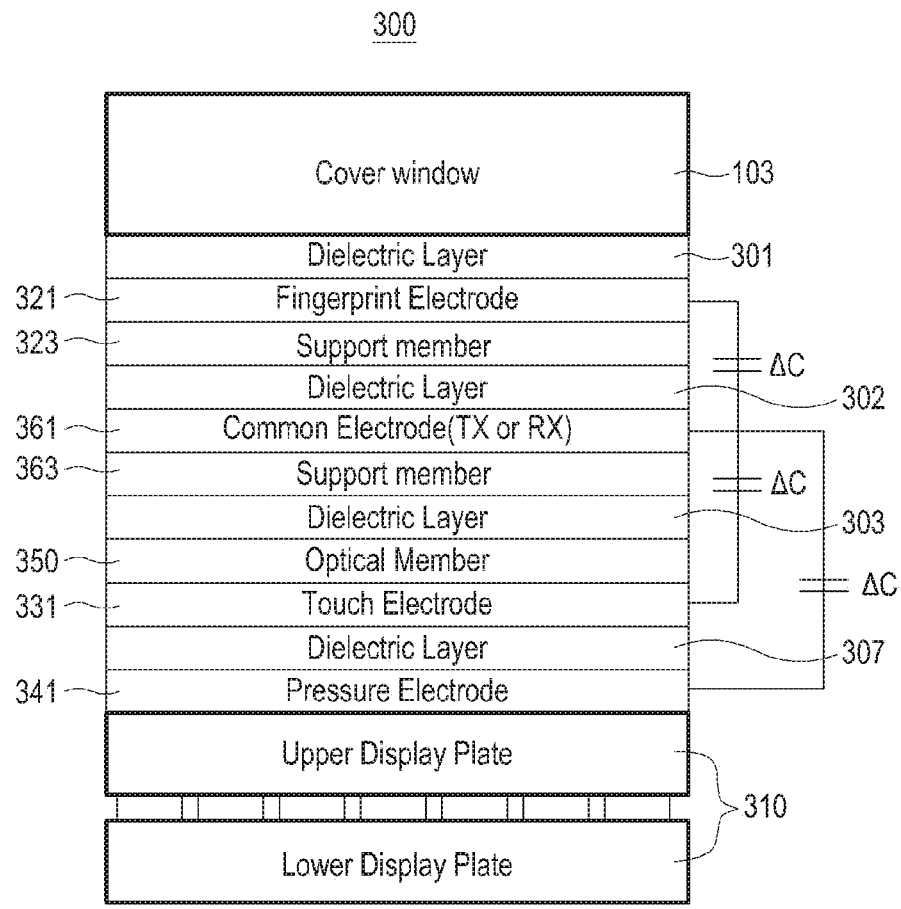

FIG. 16 is a cross-sectional view illustrating stacked faces of the display device 300 based on the embodiment of FIG. 10, according to an embodiment of the present disclosure.

As illustrated in FIG. 16, the display device 300 includes a fingerprint electrode 321, a common electrode 361, a touch electrode 331, and/or a pressure electrode 341, which are formed between the transparent cover 103 and the display 310. The fingerprint electrode 321, the common electrode 361, the touch electrode 331, and the pressure electrode 341 may correspond to the fingerprint electrode 321, the common electrode 361, the touch electrode 331, and the pressure electrode 341 of the above-described embodiment of FIG. 11, respectively.

According to an embodiment of the present disclosure, in the display device 300, the optical member 350 and the touch electrode 331 may be integrally formed, and the display 310 and the pressure electrode 341 may be integrally formed. The touch electrode 331 may be formed directly above the optical member 350 so that a portion of the dielectric layer and the support member disposed in the above-described embodiment of FIG. 11 may be removed. In addition, the pressure electrode 341 may be formed directly on the display 310 so that a portion of the dielectric layer and the support member may be removed. Accordingly, when the display device 300 is implemented, manufacturing costs may be reduced, and the assembly process may be simplified.

According to an embodiment of the present disclosure, in the cross-section of the display device 300, the stacked layers may be sequentially set forth as the fingerprint electrode 321, the first support member 323, the dielectric layer 302, the common electrode 361, the second support member 363, the dielectric layer 350, the touch electrode 331, the dielectric layer 307, the pressure electrode 341, and the display 310 from the top side. The common electrode 361 may be electrically connected to the fingerprint electrode 321, the touch electrode 331, and/or the pressure electrode 341 to function as a fingerprint sensor, a touch sensor, and/or a pressure sensor.

Figure 17:
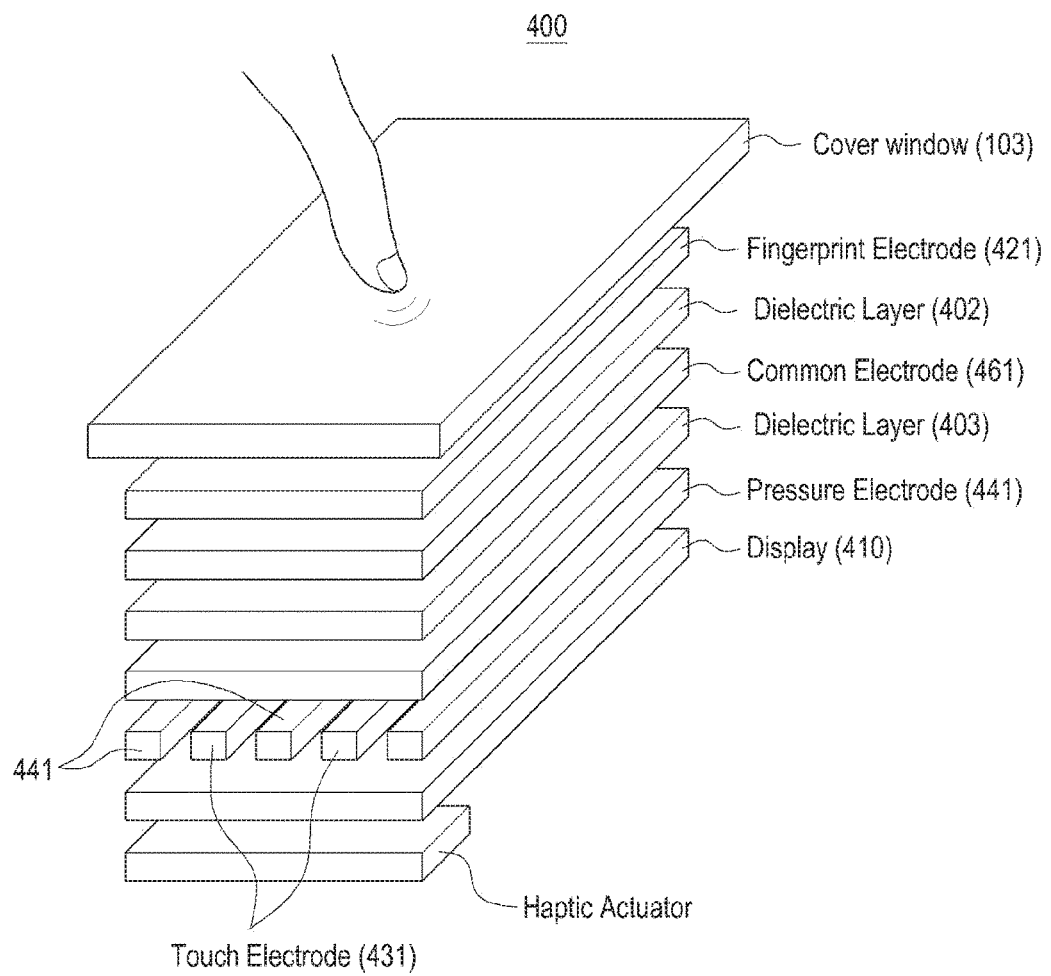
FIG. 17 illustrates a configuration of an end face of a display device, according to another embodiment of the present disclosure.

FIG. 17 illustrates a configuration of an end face of a display device 400 according to an embodiment of the present disclosure.

FIG. 17 is a perspective view of the embodiment of FIGS. 18 to 19 to be described later. An embodiment of the present disclosure may include a touch electrode 431 and a pressure electrode 441, which are alternately arranged in one layer.

As illustrated in FIGS. 2A and 2B, the display 410 may be disposed between the first face 101 and the second face 102 of the housing 100, and may be exposed through the transparent cover 103. The fingerprint sensor 420 may be disposed between the transparent cover 103 and the display 410, and the touch sensor 430 may be disposed between the fingerprint sensor 420 and the display 410. The pressure sensor 440 may be disposed between the touch sensor 430 and the display 410. The display device 400 may implement various user experiences (e.g., three-dimensional input) through a combination of the one or more sensors.

According to an embodiment of the present disclosure, in the electronic device 10, the transparent cover 103 may be positioned on the front face of the housing 100 to protect the display 410 from the external environment. The display 410 includes the fingerprint sensor 420, the touch sensor 430, or the pressure sensor 440 in the form of a panel incorporated in the display 410 so that the display 210 may be used not only as an output device, but also as an input device.

According to an embodiment of the present disclosure, the electronic device 10 may include at least one control circuit electrically connected to the display 410, the fingerprint electrode 421, the common electrode 461, the touch electrode 431, and the pressure electrode 441.

Figure 18:
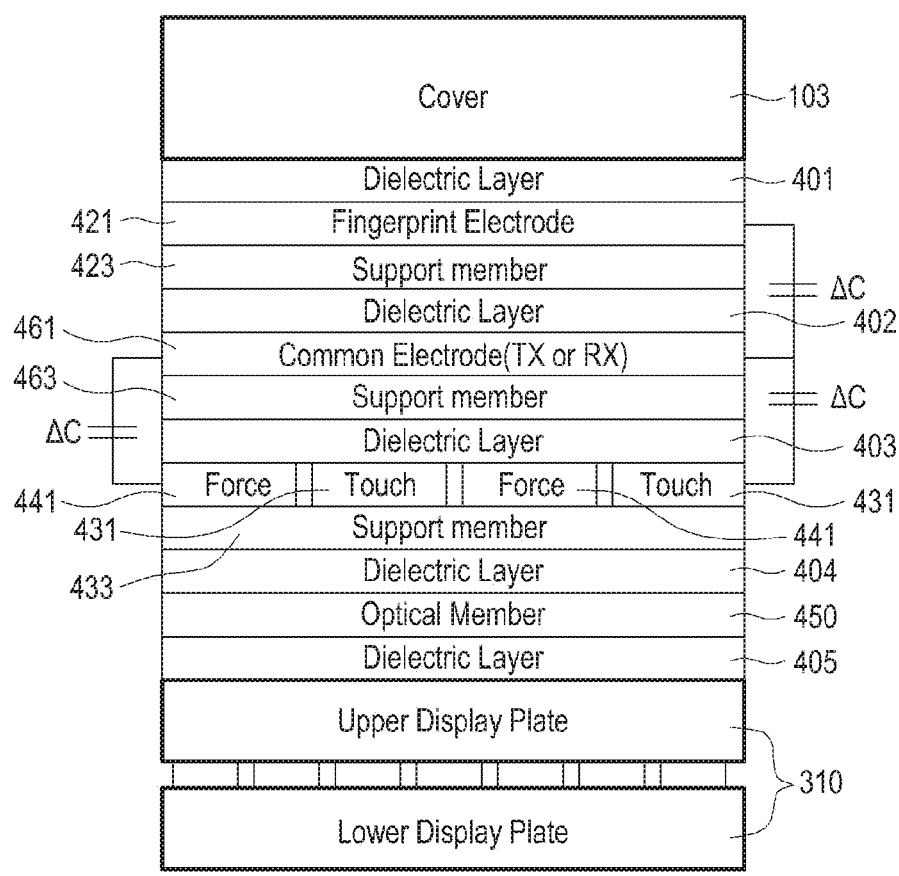
FIGS. 18 to 19 are cross-sectional views each illustrating stacked faces of a display device based on the embodiment of FIG. 17, according to an embodiment of the present disclosure.

FIG. 18 is a cross-sectional view illustrating stacked faces of the display device 400 based on the embodiment of FIG. 17, according to an embodiment of the present disclosure.

As illustrated in FIG. 18, the display device 400 includes a fingerprint electrode 421, a common electrode 461, a touch electrode 431, and/or a pressure electrode 441, which are formed between the transparent cover 103 and the display 310. The fingerprint electrode 421, the common electrode 461, the touch electrode 431, and the pressure electrode 441 may correspond to the fingerprint electrode 421, the common electrode 461, the touch electrode 431, and the pressure electrode 441 of the above-described embodiment of FIG. 17, respectively.

According to an embodiment of the present disclosure, the touch sensor 430 may be stacked to include two electrodes 431 and 461, a support member 433, and a dielectric layer 403. The pressure sensor 440 may be stacked to include two electrodes 431 and 461, a support members 433, and a dielectric layer 403. The touch electrode 431 of the touch sensor 430 and the pressure electrode 441 of the pressure sensor 440 may be formed together on one support member 433. A plurality of bar-shaped touch electrodes 431 may be arranged on the third support member 433, and a plurality of bar-shaped pressure electrodes 441 may be arranged between the touch electrodes 431.

According to an embodiment of the present disclosure, the touch electrode 431 and/or the pressure electrodes 441 formed on the third support members 433 may be reception electrodes or transmission electrodes. A touch sensor transmission electrode Tx and a pressure sensor transmission electrode Tx may be arranged parallel to each other at a predetermined interval. In the touch mode and/or the pressure mode, an operation may be performed in the state where the touch sensor transmission electrode Tx are activated together with a plurality of pressure sensor transmission electrodes Tx. In the touch mode, the operation may be performed in a state where the touch electrode 431 is activated and the plurality of pressure electrodes 441 are inactivated, and in the pressure mode, the operation may be performed in a state where the touch transmission electrode 431 is inactivated and only the plurality of pressure sensor electrodes 441 are activated.

According to an embodiment of the present disclosure, the touch electrode 431 and/or the pressure electrode 441 formed on the third support member 433 are alternately arranged parallel to each other. However, without being limited thereto, the touch electrode 431 and/or the pressure electrode 441 may be disposed in a cross form in relation to each other, and the intersection point of the touch electrode 431 and the pressure electrode 441 may be isolated through an insulating member and the like.

According to an embodiment of the present disclosure, the touch sensor 430 and/or the pressure sensor 440 may be implemented through an electrical connection between the touch electrode 431 and/or the pressure sensor 440 on the third support member 433 and the common electrode 461 on the second support member 436. The third support member 433 on which the touch electrode 431 and/or the pressure electrode 441 are disposed and the second support member 463 on which the common electrode 461 is disposed may be stacked on each other, and a dielectric layer 403 may be disposed therebetween. The dielectric layer 403 may be formed of, for example, silicon, air, foam, membrane, OCA, sponge, rubber, ink, or polymer (e.g., PC or PET).

According to an embodiment of the present disclosure, at least one of the fingerprint electrode 421, the common electrode 461, the touch electrode 431, and the pressure electrode 441 may include a transparent conductive material. At least one of the fingerprint electrode 421, the common electrode 461, the touch electrode 431, and the pressure electrode 441 may include at least one of ITO, IZO, PEDOT, an Ag nanowire, a transparent polymer conductor, and graphene.

Figure 19:
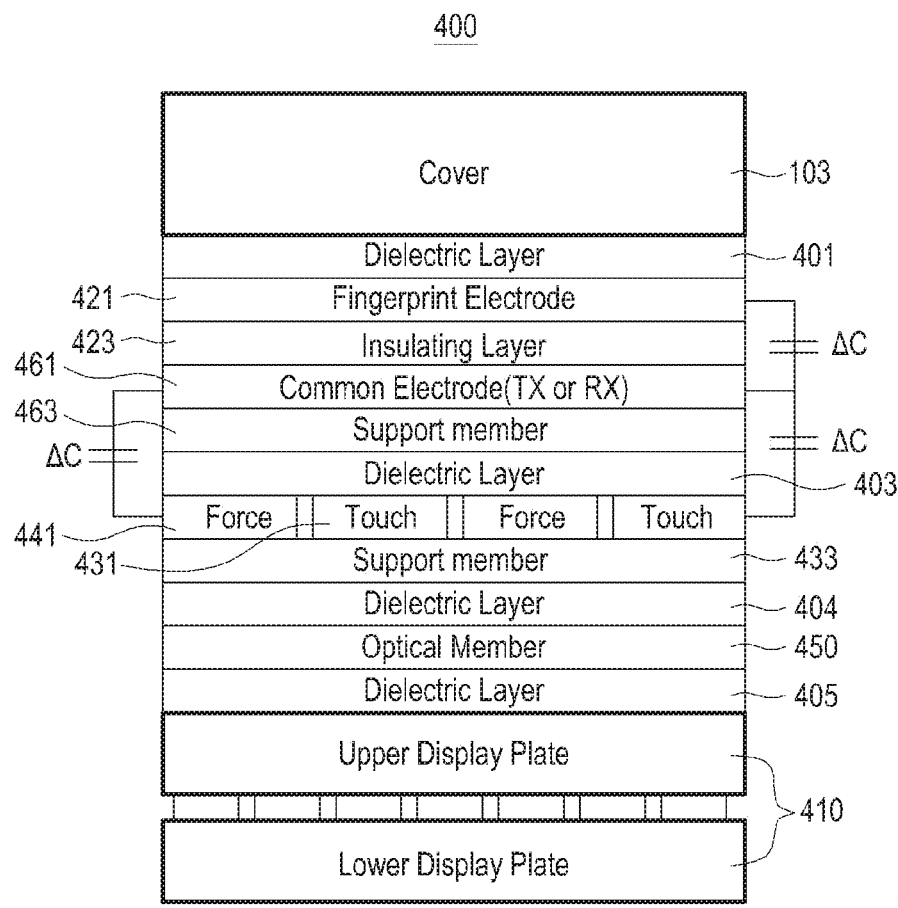

FIG. 19 is a cross-sectional view illustrating stacked faces of the display device 400 based on the embodiment of FIG. 17, according to an embodiment of the present disclosure.

As illustrated in FIG. 19, the display device 400 includes a fingerprint electrode 421, a common electrode 461, a touch electrode 431, and/or a pressure electrode 441, which are formed between the transparent cover 103 and the display 310. The fingerprint electrode 421, the common electrode 461, the touch electrode 431, and the pressure electrode 441 may correspond to the fingerprint electrode 421, the common electrode 461, the touch electrode 431, and the pressure electrode 441 of the above-described embodiment of FIG. 17, respectively.

According to an embodiment of the present disclosure, compared with the above-described embodiment of FIG. 18, the display device 400 may be implemented such that the fingerprint electrode 421 and the common electrode 461 are disposed on one support member 463 in the stacked structure and an insulating layer 423 is included therebetween. The fingerprint electrode 421 and the common electrode 461 may be arranged to face different directions, and the fingerprint electrode 421 and the common electrode 461 may be formed in a bar pattern. The fingerprint electrode 421 may be an X-axis electrode portion formed in one direction (X-axis direction), and the common electrode 461 may be a Y-axis electrode portion formed in a direction crossing the X-axis electrode portion (Y-axis direction). The fingerprint electrode 421 and the common electrode 461 are folded together and a fingerprint of a finger may be sensed through a changed value at the position where the finger electrode 221 and the common electrode 222 intersect.

Figure 20:
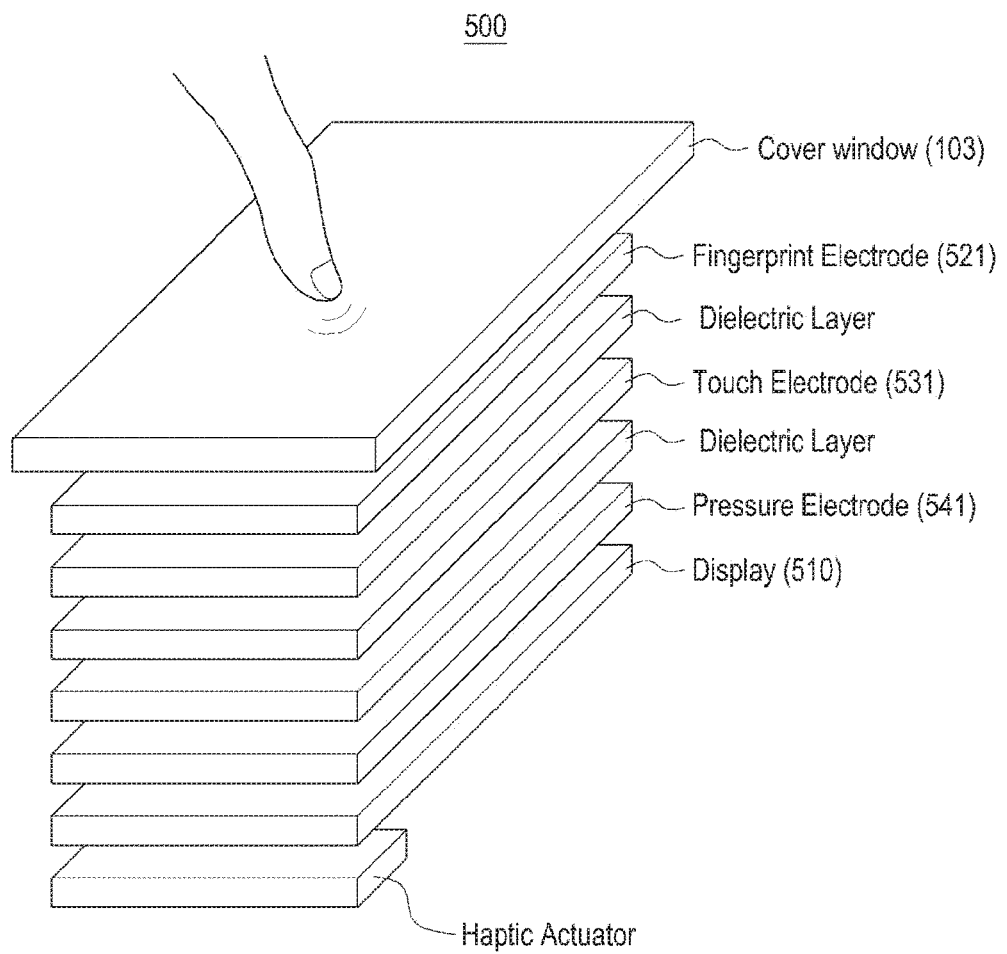
FIG. 20 illustrates a configuration of an end face of a display device, according to an embodiment of the present disclosure.

FIG. 20 illustrates a configuration of an end face of a display device 500 according to an embodiment of the present disclosure.

FIG. 20 is a perspective view of the embodiments of FIGS. 21 to 28, and the present embodiment may include at least one sensor above the display 510 unlike the embodiment of FIG. 3. Also, unlike the embodiments of FIGS. 10 and 17, the display device 500 may be implemented in a state where a common electrode is removed by driving in a self capacitance manner.

As illustrated in FIGS. 2A and 2B, the display 510 may be disposed between the first face 101 and the second face 102 of the housing 100, and may be exposed through the transparent cover 103. A fingerprint sensor 520 may be disposed between the transparent cover 103 and the display 410, and the touch sensor 530 may be disposed between the fingerprint sensor 450 and the display 510. The pressure sensor 540 may be disposed between the touch sensor 530 and the display 510. The display device 500 may implement various user experiences (e.g., three-dimensional input) through a combination of the one or more sensors.

According to an embodiment of the present disclosure, in the electronic device 10, the transparent cover 103 may be positioned on the front face of the housing 100 to protect the display 510 from the external environment. The display 510 includes the fingerprint sensor 520, the touch sensor 530, or the pressure sensor 540 in the form of a panel incorporated in the display 510 so that the display 210 may be used not only as an output device, but also as an input device.

According to an embodiment of the present disclosure, the electronic device 10 may include at least one control circuit electrically connected to the display 510, the fingerprint electrode 521, the touch electrode 531, and the pressure electrode 541.

Figure 21:
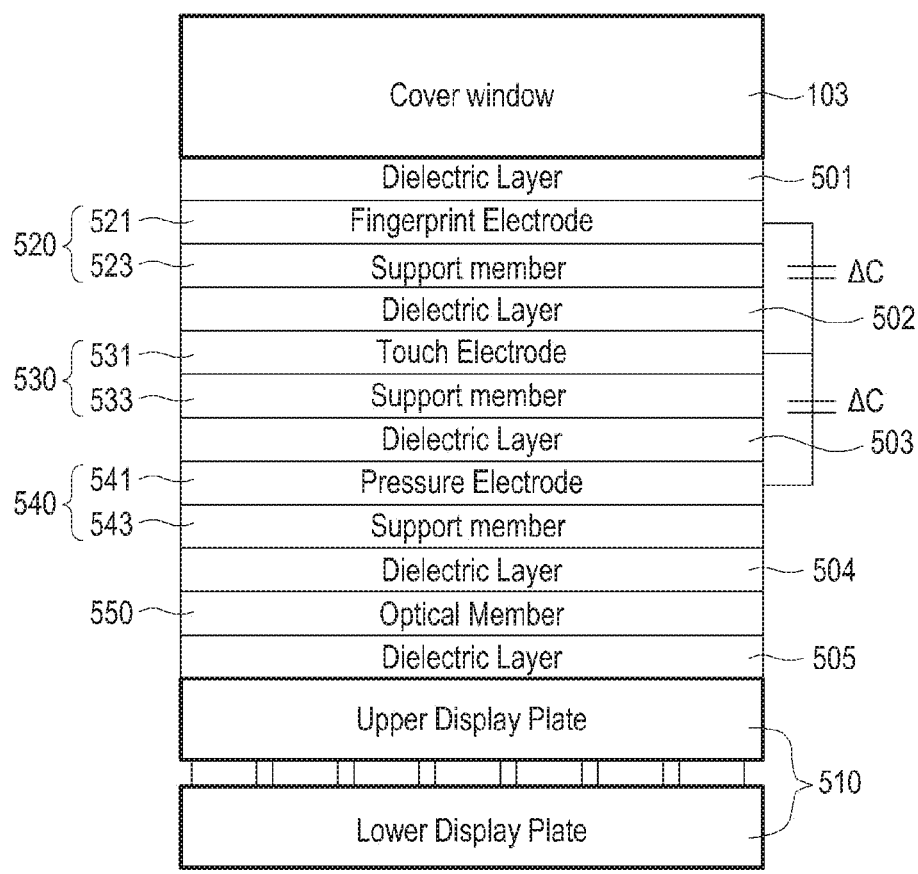
FIGS. 21 to 28 are cross-sectional views each illustrating stacked faces of a display device based on the embodiment of FIG. 20, according to an embodiment of the present disclosure.

FIG. 21 is a cross-sectional view illustrating stacked faces of the display device 500 based on the embodiment of FIG. 20, according to an embodiment of the present disclosure.

As illustrated in FIG. 21, the display device 500 includes a fingerprint sensor 520, a touch sensor 530, and/or a pressure sensor 540, which are formed between the transparent cover 103 and the display 510.

According to an embodiment of the present disclosure, the fingerprint sensor 520 may be stacked to include the fingerprint electrode 521 and the first support member 523. Almost the entire area of the fingerprint sensor 520 may overlap with the display 510 when viewed from a point above the transparent cover 103. Almost the entire area of the fingerprint sensor 520 may overlap with the touch sensor 530 and/or the pressure sensor 540.

According to an embodiment of the present disclosure, the touch sensor 530 may be stacked to include the touch electrode 531 and the second support member 533. Almost the entire area of the touch sensor 530 may overlap with the display 510 when viewed from a position above the transparent cover 103. Almost the entire area of the touch sensor 530 may overlap with the fingerprint sensor 520 and/or the pressure sensor 540.

According to an embodiment of the present disclosure, the pressure sensor 540 may be stacked to include the pressure electrode 541 and the third support member 543. Almost the entire area of the pressure sensor 540 may overlap with the display 510 when viewed from a position above the transparent cover 103.

According to an embodiment of the present disclosure, at least one of the fingerprint electrode 521, the touch electrode 531, and the pressure electrode 541 may include a transparent conductive material. At least one of the fingerprint electrode 521, the touch electrode 531, and the pressure electrode 541 may include at least one of ITO, IZO, PEDOT, an Ag nanowire, a transparent polymer conductor, and graphene.

According to an embodiment of the present disclosure, at least one of the fingerprint electrode 521, the touch electrode 531, and the pressure electrode 541 uses one electrode per basic pixel for touch recognition, and may implement a self-capacitance method, which reads a change in capacitance of the electrode. According to an embodiment of the present disclosure, an optical member 550 may be disposed below the touch sensor 540. The optical member 550 transmits therethrough a screen output from the display 510, and at least one optical member 550 may be stacked on the display 510.

Figure 22:
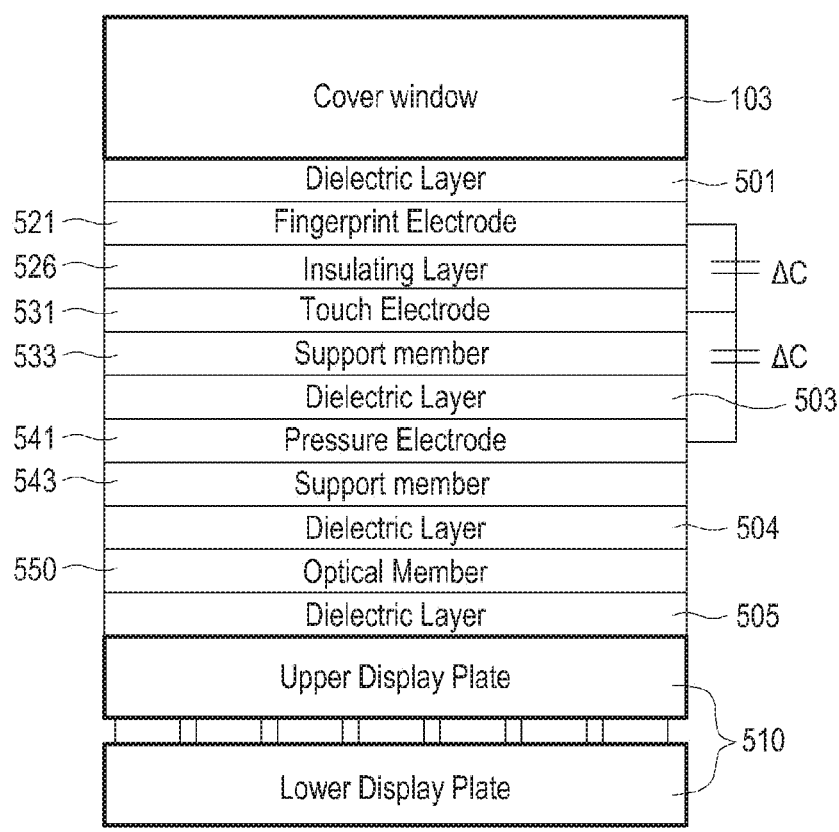

FIG. 22 is a cross-sectional view illustrating stacked faces of the display device 500 based on the embodiment of FIG. 20, according to an embodiment of the present disclosure.

As illustrated in FIG. 22, the display device 500 includes a fingerprint electrode 521, a touch electrode 531, and/or a pressure electrode 541, which are formed between the transparent cover 103 and the display 310. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to an embodiment of the present disclosure, compared with the above-described embodiment of FIG. 21, the display device 500 may be implemented such that the fingerprint electrode 521 and the touch electrode 531 are disposed on one second support member 533 in the stacked structure and an insulating layer 526 is included therebetween. The fingerprint electrode 521 and the touch electrode 531 may be arranged to face different directions, and the fingerprint electrode 521 and the common electrode 531 may be formed in a bar pattern. The fingerprint electrode 521 may be an X-axis electrode portion formed in one direction (X-axis direction), and the common electrode 261 may be a Y-axis electrode portion formed in a direction crossing the X-axis electrode portion (Y-axis direction).

Figure 23:
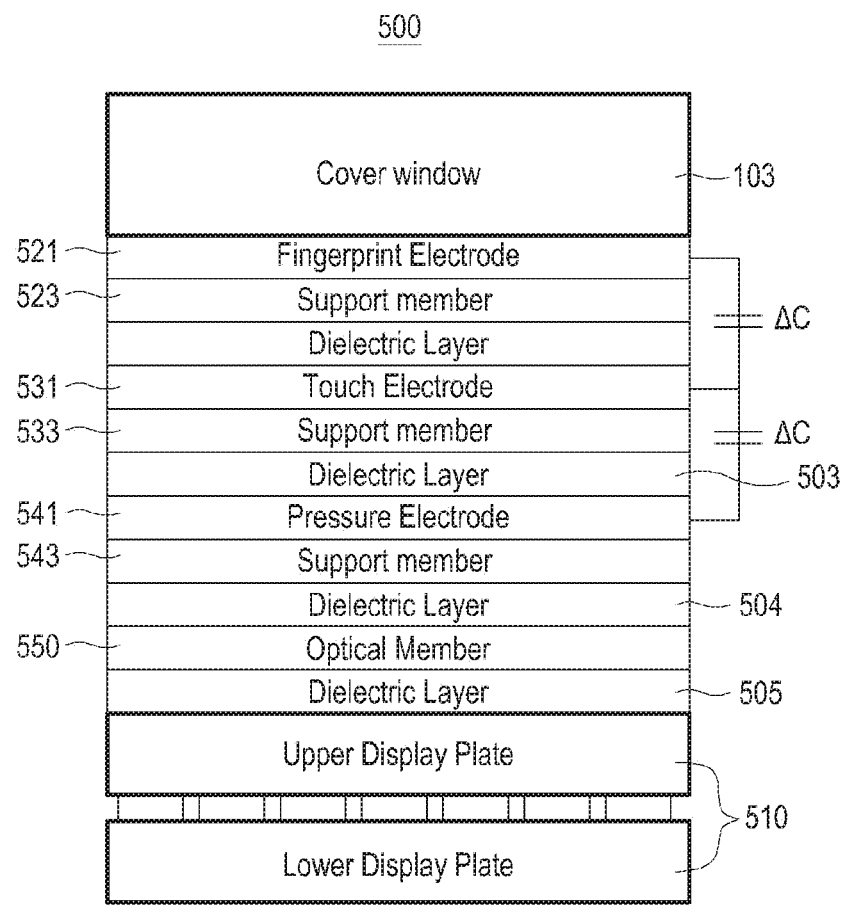

FIG. 23 is a cross-sectional view illustrating stacked faces of the display device 500 based on the embodiment of FIG. 20, according to an embodiment of the present disclosure.

As illustrated in FIG. 23, the display device 500 includes a fingerprint electrode 521, a touch electrode 531, and/or a pressure electrode 541, which are formed between the transparent cover 103 and the display 310. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to an embodiment of the present disclosure, compared with the above-described embodiment of FIG. 21, the display device 500 may be configured such that the transparent cover 103 and the fingerprint electrode 521 may be integrally formed. The fingerprint electrode 521 may be directly formed on the transparent cover 103 to partially remove the dielectric layer. Accordingly, the dielectric layer above the fingerprint sensor 520 is removed, which enables manufacturing costs to be reduced and a thinner display device 500 to be implemented.

Figure 24:
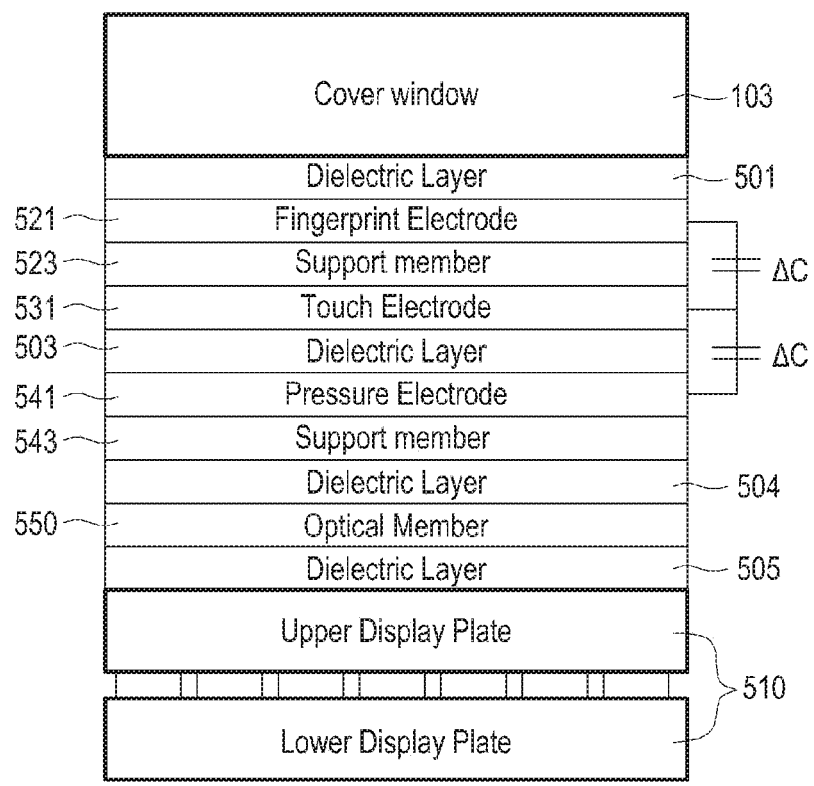

FIG. 24 is a cross-sectional view illustrating stacked faces of the display device 500 based on the embodiment of FIG. 20, according to an embodiment of the present disclosure.

As illustrated in FIG. 24, the display device 500 includes a fingerprint electrode 521, a touch electrode 531, and/or a pressure electrode 541, which are formed between the transparent cover 103 and the display 310. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to the an embodiment of the present disclosure, compared with a case where each electrode according to the above-described embodiment of FIG. 21 is formed on each of the corresponding support members, the display device 500 is configured such that two electrodes may be disposed on one support member 523. For example, separate electrodes may be formed above and below one support member 523, respectively.

According to an embodiment of the present disclosure, the display device 500 includes a fingerprint electrode 521 formed above the first support member 523 and a touch electrode 531 formed below the first support member 523.

According to an embodiment of the present disclosure, in the cross-section of the display device 500, the stacked layers may be sequentially set forth as the fingerprint electrode 521, the first support member 523, the touch electrode 531, the dielectric layer 503, the pressure electrode 541, the third support member 543, the dielectric layer 504, and the optical member 550 from the top side.

According to an embodiment of the present disclosure, two electrodes may be formed on one support member 523 so that a portion of the dielectric layer and a plurality of support members disposed in the above-described embodiment of FIG. 21 may be removed. Accordingly, when the display device 500 is implemented, manufacturing costs may be reduced, and the assembly process may be simplified.

Figure 25:
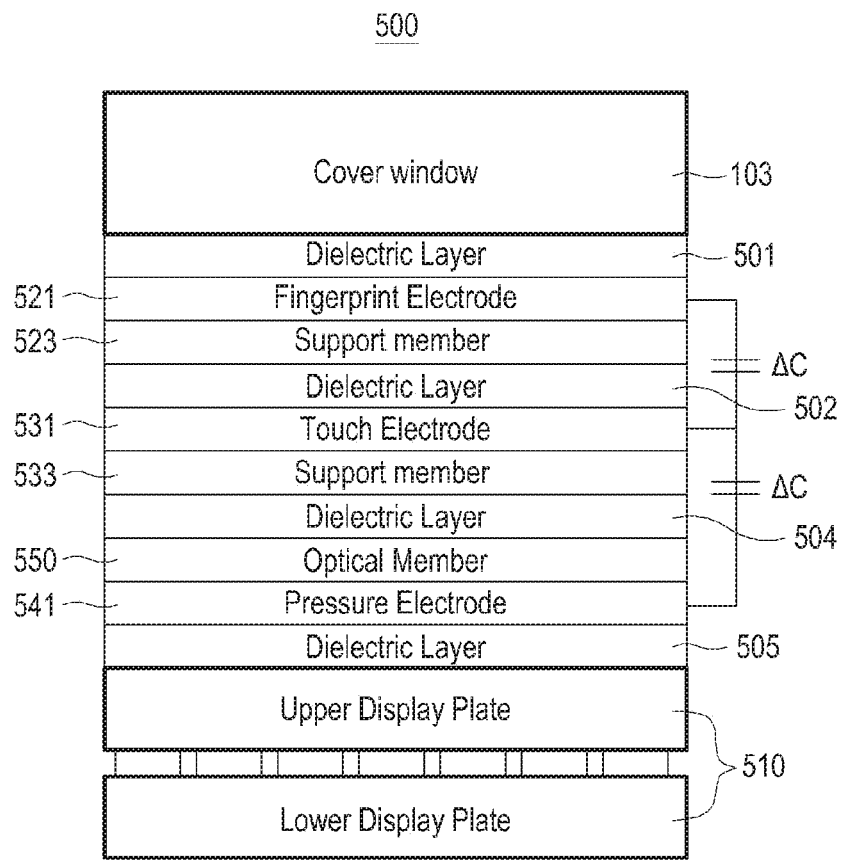

FIG. 25 is a cross-sectional view illustrating stacked faces of the display device 500 based on the embodiment of FIG. 20, according to an embodiment of the present disclosure.

As illustrated in FIG. 25, the display device 500 includes a fingerprint electrode 521, a touch electrode 531, and/or a pressure electrode 541, which are formed between the transparent cover 103 and the display 310. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to an embodiment of the present disclosure, compared with the above-described embodiment of FIG. 21, the display device 500 may be configured such that the optical member 550 and the pressure electrode 541 may be integrally formed. The pressure electrode 541 may be formed directly above or below the display 550 so that a portion of the dielectric layer and the support member disposed in the above-described embodiment of FIG. 21 may be removed. Accordingly, when the display device 500 is implemented, manufacturing costs may be reduced, and the assembly process may be simplified.

According to an embodiment of the present disclosure, since the pressure sensor 540 is formed integrally with the optical member 550, the dielectric layers 504 and 505 may be formed above and below the pressure sensor 540 and the optical member 550, respectively.

Figure 26:
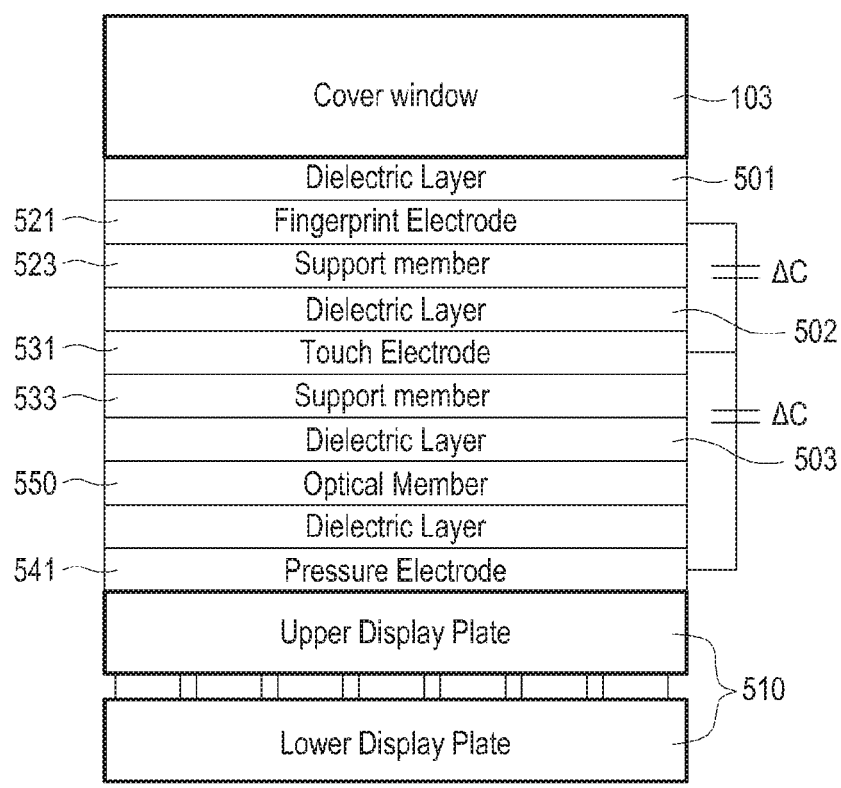

FIG. 26 is a cross-sectional view illustrating stacked faces of the display device 500, based on the embodiment of FIG. 20, according to an embodiment of the present disclosure.

As illustrated in FIG. 26, the display device 500 includes a fingerprint electrode 521, a touch electrode 531, and/or a pressure electrode 541, which are formed between the transparent cover 103 and the display 510. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to an embodiment of the present disclosure, compared with the above-described embodiment of FIG. 21, the display device 500 may be configured such that the display 510 and the fingerprint electrode 541 may be integrally formed. The pressure electrode 541 may be formed directly on the display 510 so that a portion of the dielectric layer and the support member disposed in the above-described embodiment of FIG. 21 may be removed. Accordingly, when the display device 500 is implemented, manufacturing costs may be reduced, and the assembly process may be simplified.

Since the touch sensor 540 is formed integrally with the display 510, an optical member 550 may be disposed above the touch sensor 541. Since the touch electrode 531 is disposed above the optical member 550 and the pressure electrode 541 is disposed below the optical member 250, dielectric layers 503 and 504 may be included above and below the optical member 550, respectively.

Figure 27:
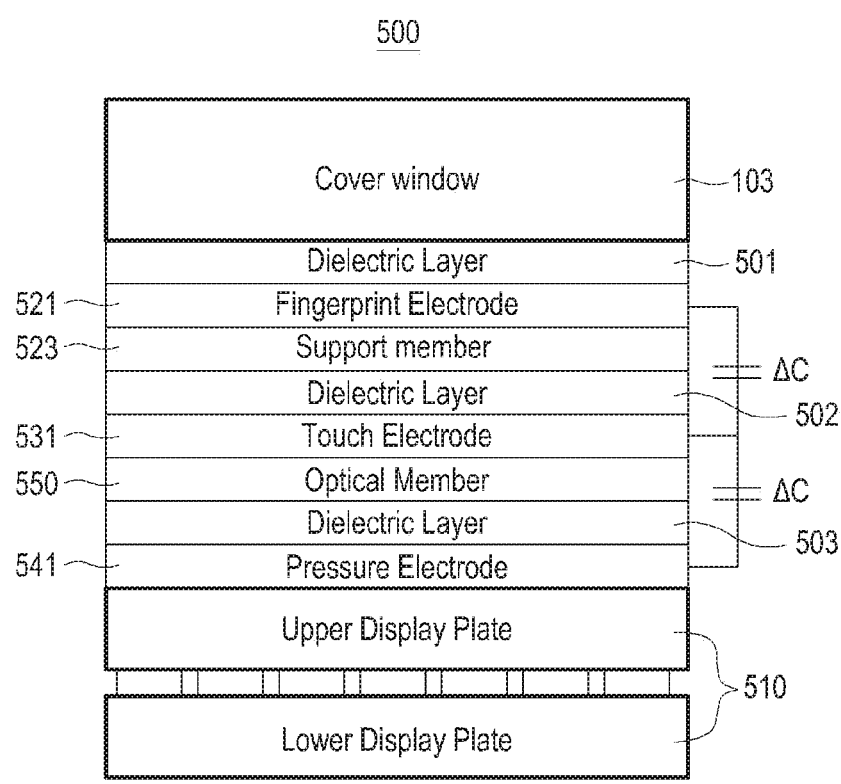

FIG. 27 is a cross-sectional view illustrating stacked faces of the display device 500 based on the embodiment of FIG. 20, according to an embodiment of the present disclosure.

As illustrated in FIG. 27, the display device 500 includes a fingerprint electrode 521, a touch electrode 531, and/or a pressure electrode 541, which are formed between the transparent cover 103 and the display 310. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to an embodiment of the present disclosure, in the display device 500, the optical member 550 and the touch electrode 531 may be integrally formed, and the display 510 and the pressure electrode 541 may be integrally formed. The touch electrode 531 may be formed directly above the optical member 550 so that a portion of the dielectric layer and the support member disposed in the above-described embodiment of FIG. 21 may be removed. In addition, the pressure electrode 541 may be formed directly on the display 510 so that a portion of the dielectric layer and the support member may be removed. Accordingly, when the display device 500 is implemented, manufacturing costs may be reduced, and the assembly process may be simplified.

According to an embodiment of the present disclosure, in the cross-section of the display device 500, the stacked layers may be sequentially set forth as the fingerprint electrode 521, the first support member 523, the dielectric layer 502, the touch electrode 550, the dielectric layer 503, the pressure electrode 541, and the display 510 from the top side.

Figure 28:
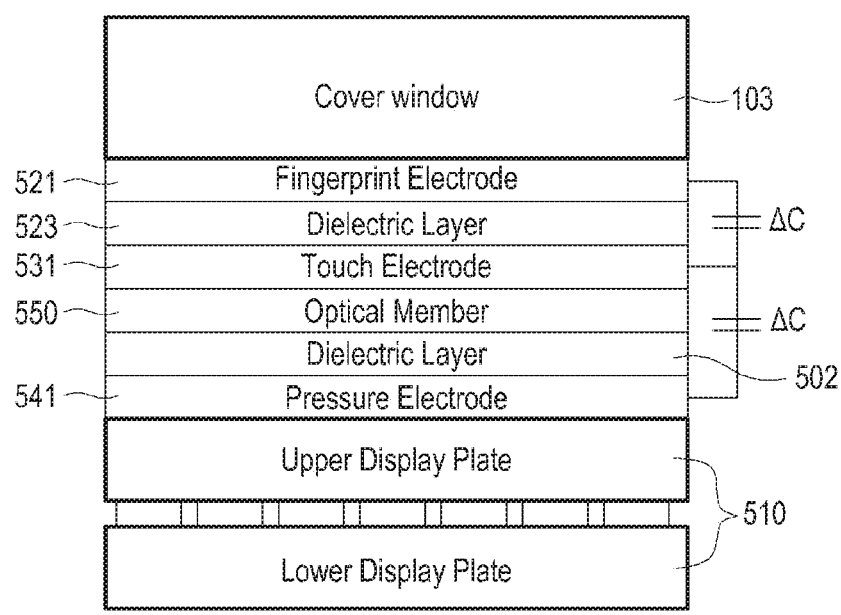

FIG. 28 is a cross-sectional view illustrating stacked faces of the display device 500 based on the embodiment of FIG. 20, according to an embodiment of the present disclosure.

As illustrated in FIG. 28, the display device 500 includes a fingerprint electrode 521, a touch electrode 531, and/or a pressure electrode 541, which are formed between the transparent cover 103 and the display 310. The fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

According to an embodiment of the present disclosure, compared with the above-described embodiment of FIG. 21, the display device 500 may be configured such that the transparent cover 103 and the fingerprint electrode 521 may be integrally formed. The fingerprint electrode 521 may be directly formed on the transparent cover 103 to partially remove the dielectric layer.

According to an embodiment of the present disclosure, in the display device 500, the optical member 550 and the touch electrode 531 may be integrally formed, and the display 510 and the pressure electrode 541 may be integrally formed. The touch electrode 531 may be formed directly above the optical member 550 so that the dielectric layer and the support member disposed in the above-described embodiment of FIG. 21 may be removed. In addition, the pressure electrode 541 may be formed directly on the display 510 so that the dielectric layer and the support member may be removed. Accordingly, when the display device 500 is implemented, since the support member is removed and a portion of the dielectric layer is removed, manufacturing costs may be reduced, and the assembly process may be simplified.

According to an embodiment of the present disclosure, in the cross-section of the display device 500, the stacked layers may be sequentially set forth as the transparent cover 103, the fingerprint electrode 521, the dielectric layer 502, the touch electrode 531, the optical member 550, the dielectric layer 502, the pressure electrode 541, and the display 510 from the top side.

FIGS. 29 to 32 are schematics each illustrating the time-division switching of a display device 500 based on the embodiment of FIG. 20, according to an embodiment of the present disclosure.

As illustrated in FIGS. 29 to 32, the fingerprint electrode 521, the touch electrode 531, and the pressure electrode 541 may correspond to the fingerprint electrode 521, the touch electrode 531, and the pressure electrode 541 of the above-described embodiment of FIG. 21, respectively.

Figure 29:
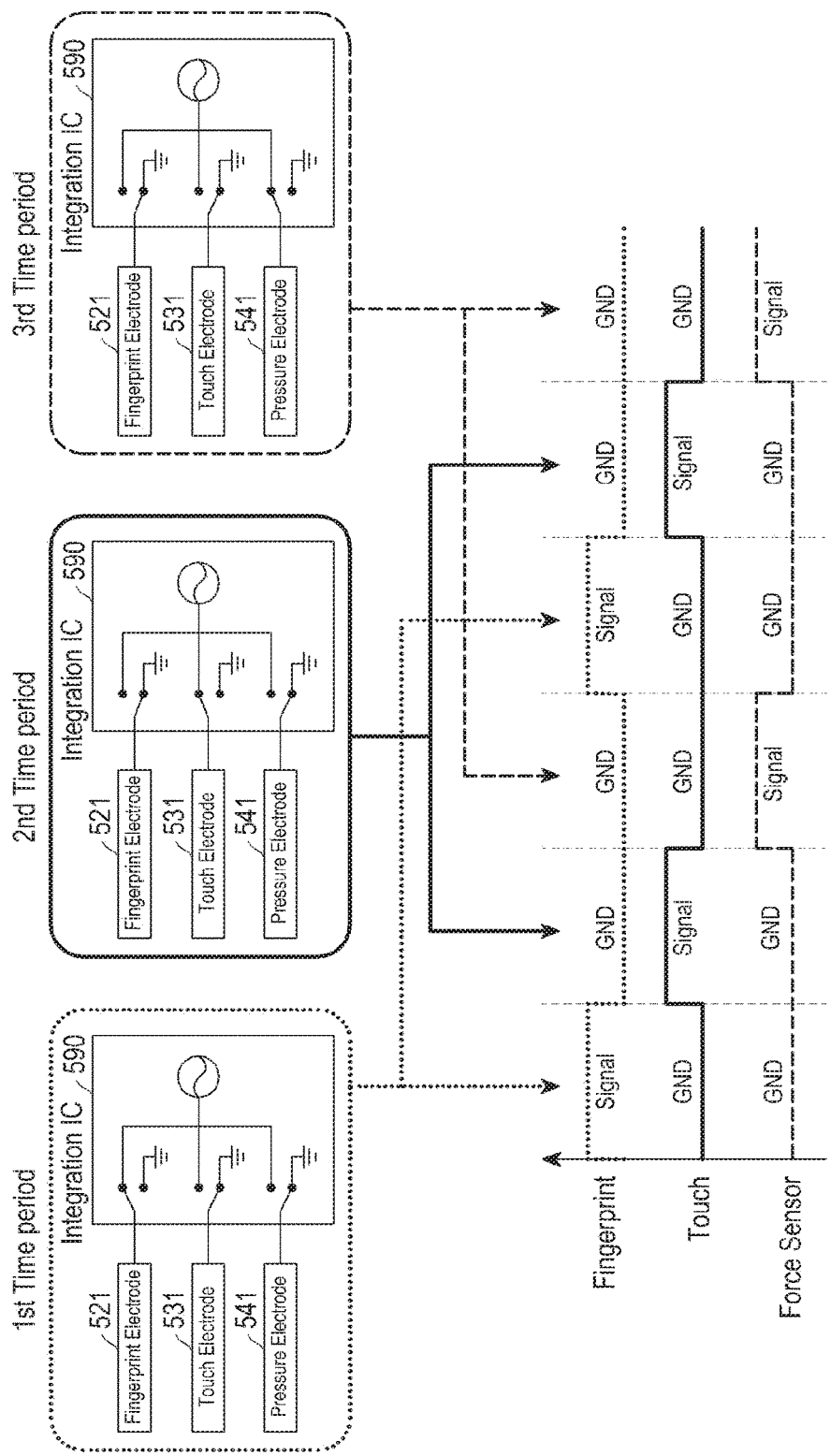
FIGS. 29 to 32 are schematics each illustrating time-division switching of a display device based on the embodiment of FIG. 20, according to an embodiment of the present disclosure.

As illustrated in FIG. 29, the three-dimensional input method through the display device 500 may divide the time into three periods, and may transmit/receive a signal of one of the fingerprint electrode 521, the touch electrode 531, and the pressure electrode 541 per divided time period.

According to an embodiment of the present disclosure, the electronic device 10 includes a control circuit 590 electrically connected to at least one of the fingerprint electrode 521, the touch electrode 531, and the pressure electrode 541, and the control circuit 590 may sense the fingerprint of a user's finger using the fingerprint electrode 521. In addition, the control circuit 590 may sense the touch position of the user's finger using the touch electrode 531, and may sense the pressure of the user's finger using the pressure electrode 541.

According to an embodiment of the present disclosure, the display device 500 of the electronic device 10 may repeatedly perform time-division switching of three periods. For example, during the first time period, the received signal may be received via the fingerprint electrode 521. In the first time period, a driving voltage may be applied through the fingerprint electrode 521, and a reference voltage (e.g., a ground voltage) may be applied to the touch electrode 531 and the pressure electrode 541.

According to an embodiment of the present disclosure, during the first time period, the plurality of fingerprint electrodes 521 may detect a fingerprint sensing signal by sensing a signal at a fingerprint reception electrode that responds to the driving signal of the fingerprint transmission electrodes in a capacitance change manner. The fingerprint electrodes 521 use one electrode per basic pixel for touch recognition, and may implement a self-capacitance method that reads a change in capacitance of the electrode.

According to an embodiment of the present disclosure, during the second time period, the received signal may be received via the touch electrode 531. In the second time period, a driving voltage may be applied through the touch electrode 531, and a reference voltage (e.g., a ground voltage) may be applied to the fingerprint electrode 521 and the pressure electrode 541. During the second time period, the plurality of fingerprint electrodes 531 may detect a touch sensing signal by sensing a signal at a touch reception electrode that responds to the driving signal of the fingerprint transmission electrodes in a capacitance change manner. The touch electrodes 531 use one electrode per basic pixel for touch recognition, and may implement a self-capacitance method that reads a change in capacitance of the electrode.

According to an embodiment of the present disclosure, during the third time period, the received signal may be received via the pressure electrode 541. In the third time period, a driving voltage may be applied through the pressure electrode 541, and a reference voltage (e.g., a ground voltage) may be applied to the fingerprint electrode 521 and the touch electrode 531. During the third time period, the plurality of pressure electrodes 541 may detect a pressure sensing signal by sensing a signal at a pressure reception electrode that responds to the driving signal of the pressure transmission electrodes in a capacitance change manner. The touch electrodes 541 use one electrode per basic pixel for touch recognition, and may implement a self-capacitance method that reads a change in capacitance of the electrode.

Figure 30:
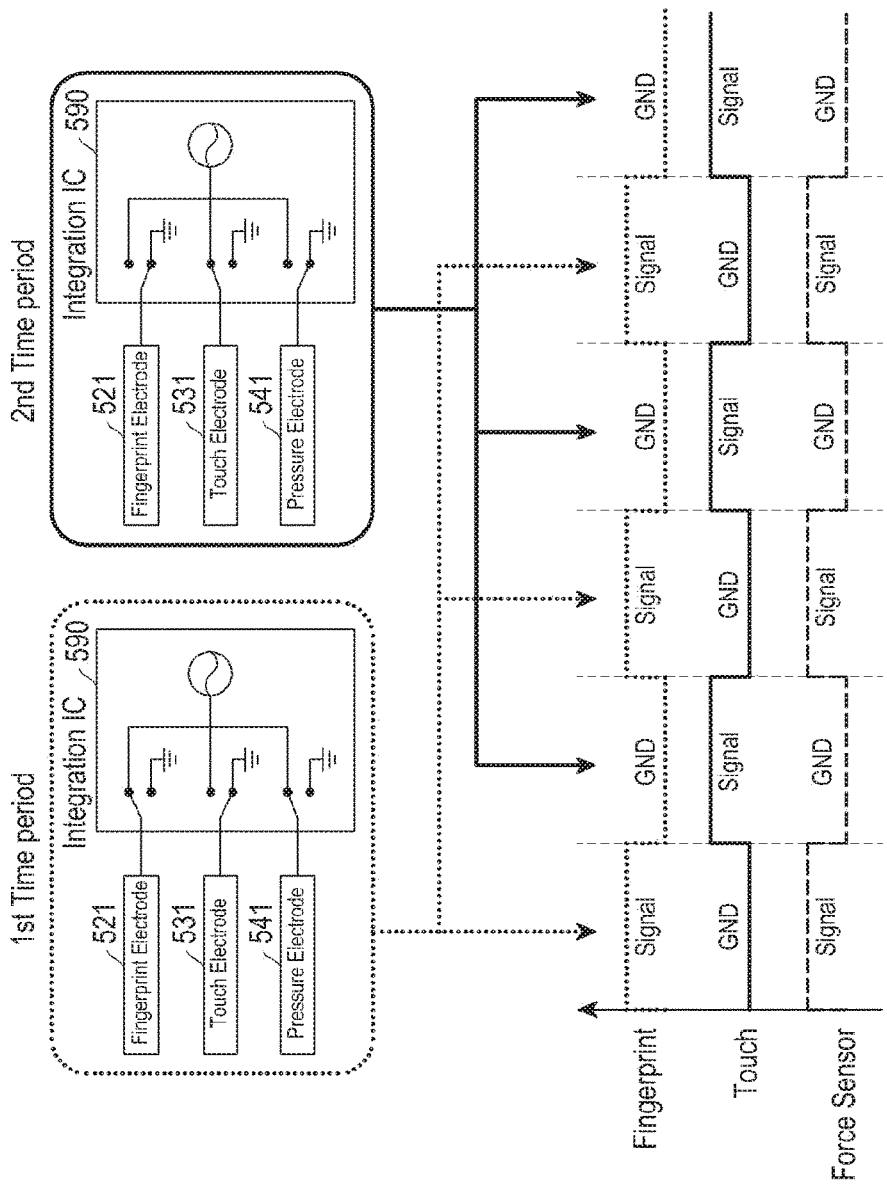

As illustrated in FIG. 30, the three-dimensional input method through the display device 200 may divide the time into two periods, and may transmit/receive a signal of at least one of the fingerprint electrode 521, the touch electrode 531, and the pressure electrode 541 per divided time period.

According to an embodiment of the present disclosure, the electronic device 10 includes a control circuit 590 electrically connected to at least one of the fingerprint electrode 521, the touch electrode 531, and the pressure electrode 541, and the control circuit 590 may sense the fingerprint of a user's finger, a touch position, and a pressure using each of the electrodes.

According to an embodiment of the present disclosure, the display device 200 of the electronic device 10 may repeatedly perform time-division switching of two periods unlike the previous embodiment of FIG. 29. For example, during the first time period, the received signal may be received via the fingerprint electrode 521 and the pressure electrode 541. In the first time period, a driving voltage may be applied through the fingerprint electrode 521 and the pressure electrode 541, and a reference voltage (e.g., a ground voltage) may be applied to the touch electrode 531.

According to an embodiment of the present disclosure, during the second time period, the received signal may be received via the touch electrode 531. In the second time period, a driving voltage may be applied through the touch electrode 531, and a reference voltage (e.g., a ground voltage) may be applied to the fingerprint electrode 521 and the pressure electrode 541.

Figure 31:
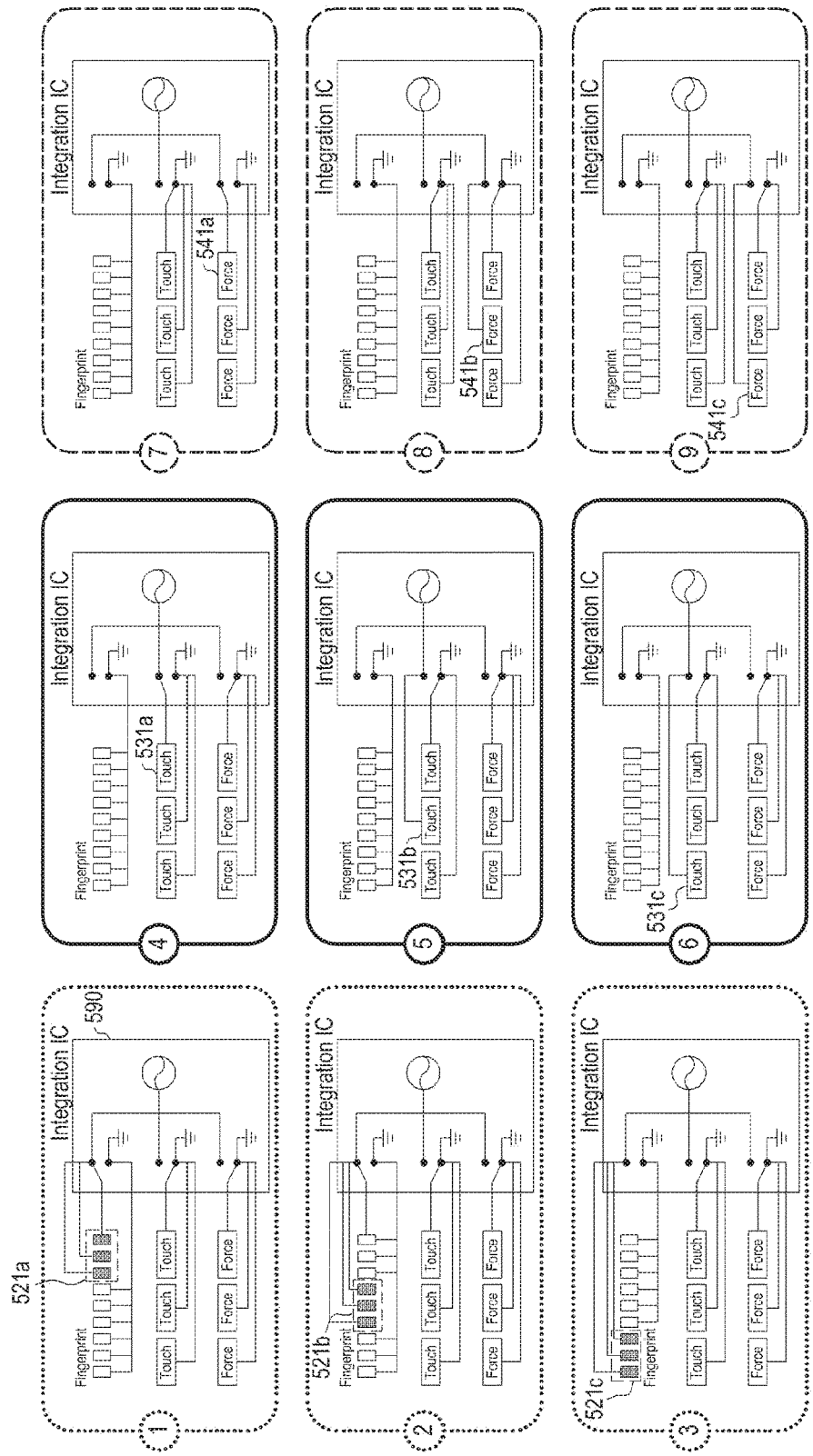

As illustrated in FIG. 31, the three-dimensional input method through the display device 200 may divide time into three periods, and may transmit/receive a signal of at least one of a plurality of fingerprint electrodes 521, a plurality of touch electrodes 531, and a plurality of pressure electrodes 541 per divided time period.

According to an embodiment of the present disclosure, the display device 500 of the electronic device 10 may repeatedly perform time-division switching of multiple periods at each electrode unlike the previous embodiment of FIG. 29. For example, during the first time period, the received signal may be received via fingerprint electrodes 521a in a region among the plurality of fingerprint electrodes 521. In the first time period, a driving voltage may be applied to fingerprint electrodes 521a in a region among the plurality of fingerprint electrodes 521, and a reference voltage (e.g., a ground voltage) may be applied to the remaining fingerprint electrodes 521b and 521c, the touch electrode 531, and the pressure electrode 541. Thereafter, during the second time period and the third time period, the received signal may be received via fingerprint electrodes 521b and 521c in the other region among the plurality of fingerprint electrodes 521. The user's fingerprint may be recognized in a time-division switching method by dividing the plurality of fingerprint electrodes 521 into three regions. All of the remaining electrodes except for the electrodes that are currently being driven may be connected to a ground electrode.

According to an embodiment of the present disclosure, the touch electrodes 531 and the pressure electrodes 541 may be driven in a state of being divided into three regions. The details are the same as those of the above-described embodiments of the fingerprint electrodes, and descriptions thereof will be omitted.

Figure 32:
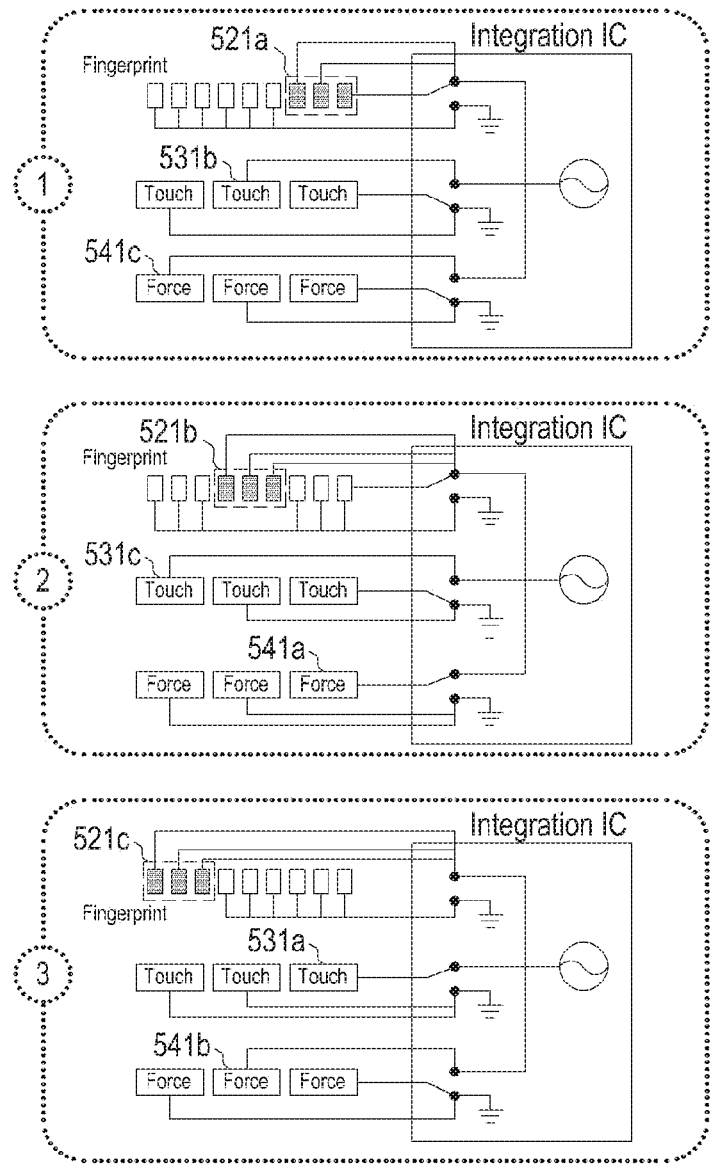

As illustrated in FIG. 32, the three-dimensional input method through the display device 200 may divide the time into three periods, and may transmit/receive a signal of at least one of the fingerprint electrode 521, the touch electrode 531, and the pressure electrode 541 per divided time period.

According to an embodiment of the present disclosure, the display device 500 of the electronic device 10 may repeatedly perform time-division switching of multiple periods while driving at least three different electrodes in one period, unlike the previous embodiment of FIG. 31. During the first time period, the received signal may be received via fingerprint electrodes 521a in a region among the plurality of fingerprint electrodes 521. Also, the reception signal may be received through the touch electrodes 531b in a region among the plurality of touch electrodes 531, and the received signal may be received through the pressure electrodes 541c in a region among the plurality of pressure electrodes 541. A driving voltage may be simultaneously applied to the fingerprint electrodes 521a, the touch electrodes 531b and the pressure electrodes 541c in respective regions, and a reference voltage (e.g., a ground voltage) may be applied to all the remaining electrodes, except for the electrodes that are currently being driven.

According to an embodiment of the present disclosure, during the second time period and the third time period, the received signal may be received via the fingerprint electrodes in another region among the plurality of fingerprint electrodes 521.

Figure 33:
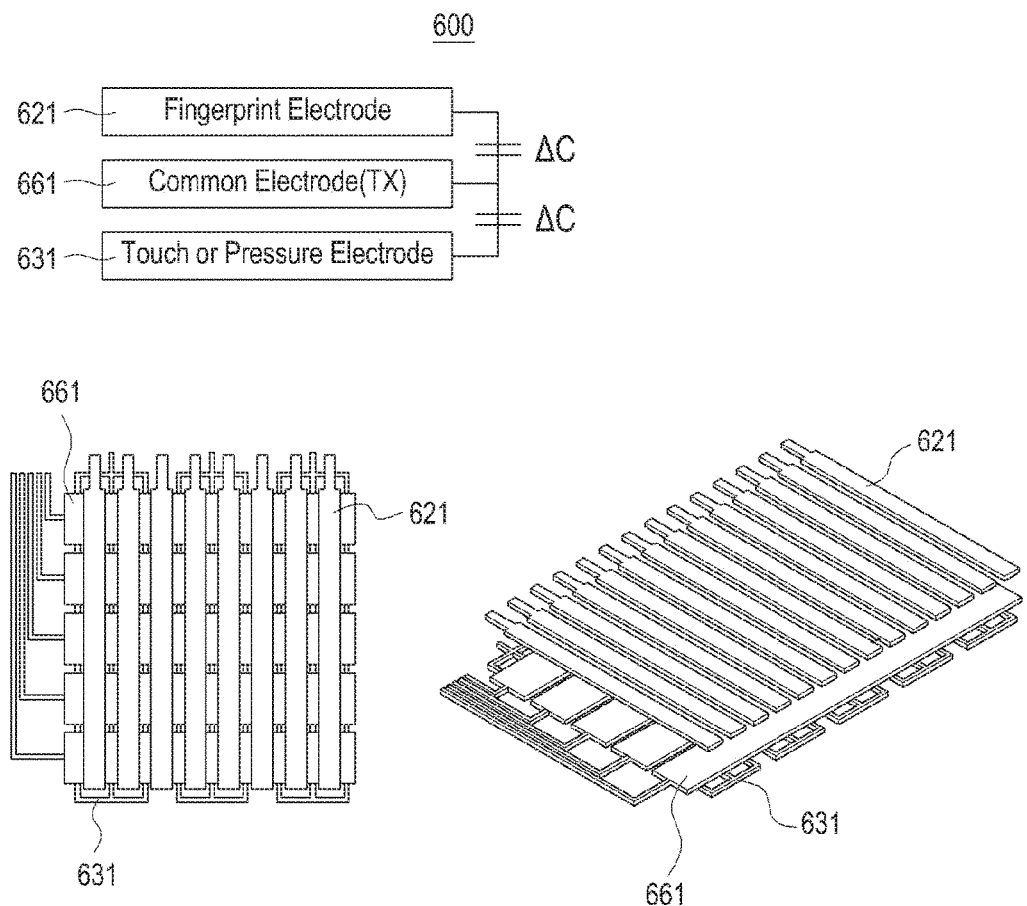
FIGS. 33 to 35 are schematics illustrating electrode patterns, according to an embodiment of the present disclosure.
Figure 34:
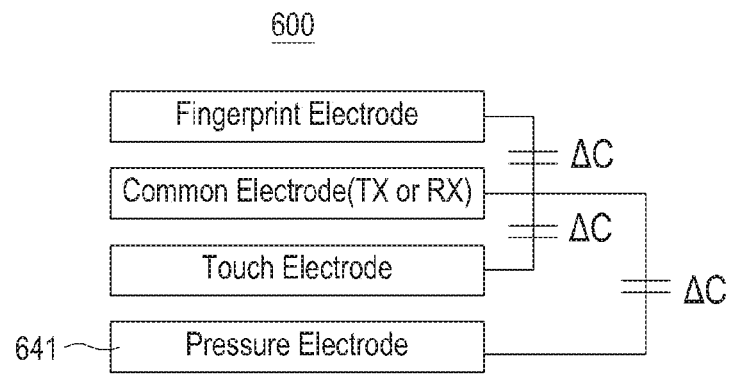
Figure 34:
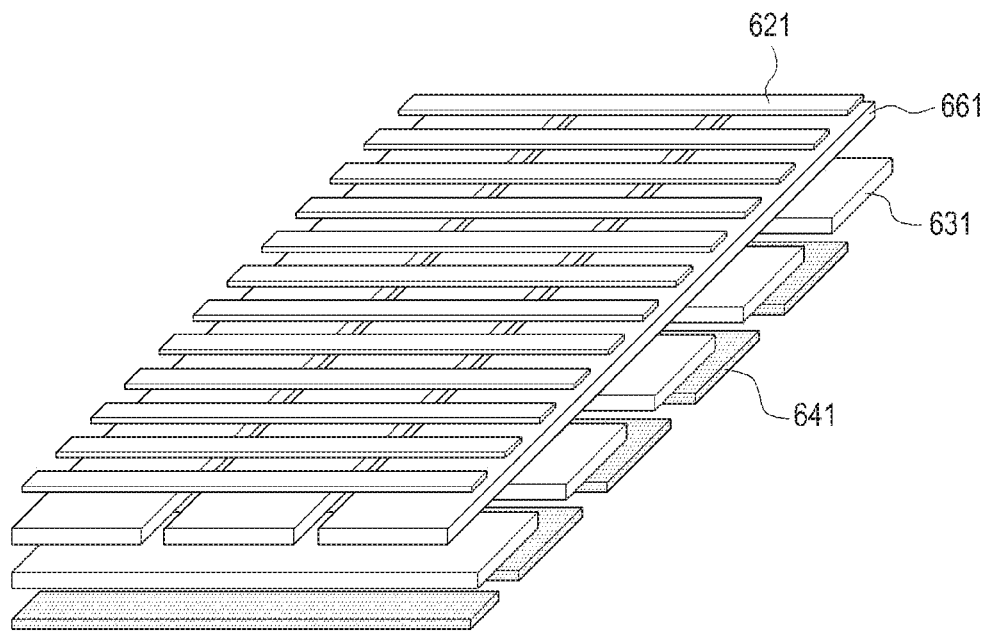
Figure 35:
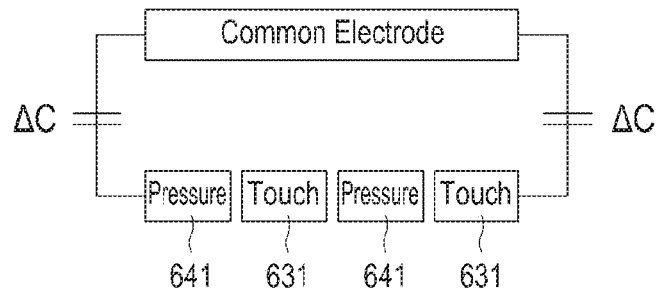
Figure 35:
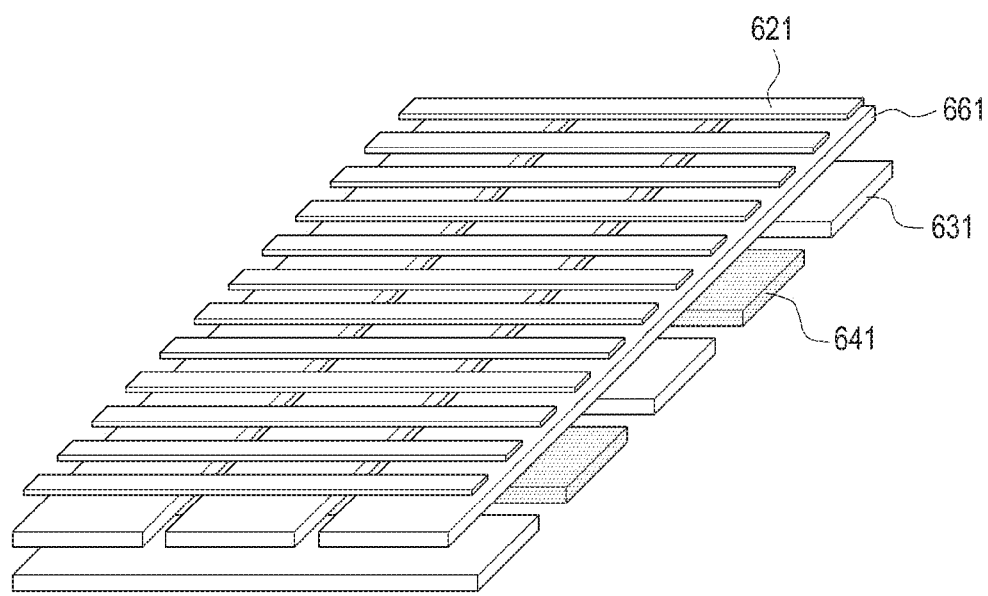

FIGS. 33 to 35 are schematics illustrating electrode patterns according to an embodiment of the present disclosure.

FIGS. 33 to 35 are views each illustrating an electrode pattern of a display device 600 according to an embodiment of the present disclosure, which is based on the embodiment of FIG. 10. The display device 600 may be formed with a fingerprint electrode 621, a common electrode 661, a touch electrode, or a pressure electrode 631. The fingerprint electrode 621, the common electrode 661, the touch electrode, and the pressure electrode 631 may correspond to the fingerprint electrode 321, the common electrode 361, the touch electrode 331, and the pressure electrode 341 of the above-described embodiment of FIG. 10, respectively.

As illustrated in FIG. 33, the display device 600 may have a plurality of flat finger electrodes 621 arranged above flat common electrodes 661. In addition, touch electrodes or pressure electrodes 631, which correspond to the fingerprint electrodes 621, may be disposed below the common electrodes 661. According to an embodiment of the present disclosure, the fingerprint electrodes 621 and the touch electrodes 631 may be stacked and disposed in a manner that minimizes an interference (overlap) therebetween. In addition, the fingerprint electrodes 621 and the pressure electrodes 631 may be stacked and disposed in a manner that minimizes the interference (overlap) therebetween.

According to an embodiment of the present disclosure, the fingerprint electrodes 621 and the touch electrodes 661 may be electrically connected to each other to form a fingerprint sensor. The touch electrodes 621 and the common electrodes 661 may be electrically connected to each other to form a touch sensor. A sensing region of the fingerprint sensor and a sensing region of the touch sensor may be provided on the substrate, including a transmission electrode layer, an insulating layer, and a reception electrode layer. The fingerprint sensor and the touch sensor may detect a fingerprint or a touch sensing signal by sensing a signal at a reception electrode that responds to a driving signal of the transmission electrodes in a mutual capacitance method in each mode. The transmission electrode layer of the sensor may be the fingerprint electrodes 621 or the touch electrodes 631, and the reception electrode layer may be the common electrodes 661. The reception electrode layer may be the common electrodes 661, and the transmission electrode layer may be the fingerprint electrodes 621 or the touch electrodes 631. When detecting a user's fingerprint or a touch position by the common electrodes 661, serving as the reception electrodes, parasitic capacitance may generated by coupling at a region where the fingerprint electrodes 621 and the touch electrodes 631 overlap with each other. The parasitic capacitance is generated in proportion to the area of the region where the fingerprint electrode and the touch electrode interfere with each other. The fingerprint electrodes 621 and the touch electrodes are structurally stacked and disposed such that the interference (overlap) between the fingerprint electrodes 621 and the touch electrodes 631 is minimized so that the influence of parasitic capacitance may be reduced and the fingerprint and touch detection performance may be improved.

According to an embodiment of the present disclosure, the plurality of fingerprint electrodes 621 may be arranged side by side in the first direction in the form of bars, and the plurality of common electrodes 661 may be arranged side by side in the second direction in the form of bars. The first direction and the second direction may be orthogonal to each other. The arrangement of the bar-shaped electrodes orthogonal to each other is illustrated in FIG. 33. However, without being limited thereto, any one of the fingerprint electrodes 621 and the common electrodes 661 may have various shapes such as a bridge shape, and may be orthogonal to each other to have overlapping regions.

According to an embodiment of the present disclosure, the plurality of touch electrodes or pressure electrodes may be arranged side by side in the first direction in the form of bars, and the plurality of common electrodes 661 may be arranged side by side in the second direction in the form of bars. The pattern of the touch electrodes 631 or the pressure electrodes 641 may be a connection of a plurality of lines arranged along a region outside the region where the fingerprint electrodes 621 are arranged in order to minimize the interference (overlap) with the fingerprint electrodes 621.

As illustrated in FIG. 34, the display device 600 may have a plurality of flat finger electrodes 621 arranged above flat common electrodes 661. In addition, the touch electrodes or pressure electrodes 631, which correspond to the fingerprint electrodes 621, may be disposed below the common electrodes 661. According to an embodiment of the present disclosure, the fingerprint electrodes 621, the touch electrodes 631, and the pressure electrodes 641 may be disposed and stacked in a manner that minimizes an interference (overlap) therebetween.

According to an embodiment of the present disclosure, the plurality of fingerprint electrodes 621 may be arranged side by side in the first direction in the form of bars, and the plurality of common electrodes 661 may be arranged side by side in the second direction in the form of bars. In addition, the plurality of touch electrodes 631 and pressure electrodes 641 may be arranged side by side in the first direction in the form of bars. The first direction and the second direction may be orthogonal to each other. Each of the electrodes may be stacked and disposed in a manner that minimizes the interference (overlap) in order to minimize the generation of parasitic capacitance depending on the area of the regions that interfere with each other.

According to an embodiment of the present disclosure, as illustrated in FIG. 35, the pattern of the touch electrodes 631 and the pressure electrodes 641 may form one layer, and may be alternately arranged to be adjacent to each other. The pressure electrodes 641 are arranged at a predetermined distance from the bar-shaped pressure electrodes 641, respectively, and still other pressure electrodes 631 may be disposed at a predetermined distance from the pressure electrodes, respectively. The width of the touch electrodes 631 and/or the pressure electrodes 641 may be greater than the width of the fingerprint electrodes 621. In addition, the pattern of the touch electrodes 631 and/or the pressure electrodes 641 may be disposed along a minimum region where the fingerprint electrodes 621 are disposed in order to minimize the interference (overlap) with the fingerprint electrodes 621.

FIGS. 36 to 39 are block diagrams each illustrating an integration IC connected to electrodes of a display device according to an embodiment of the present disclosure.

Figure 36:
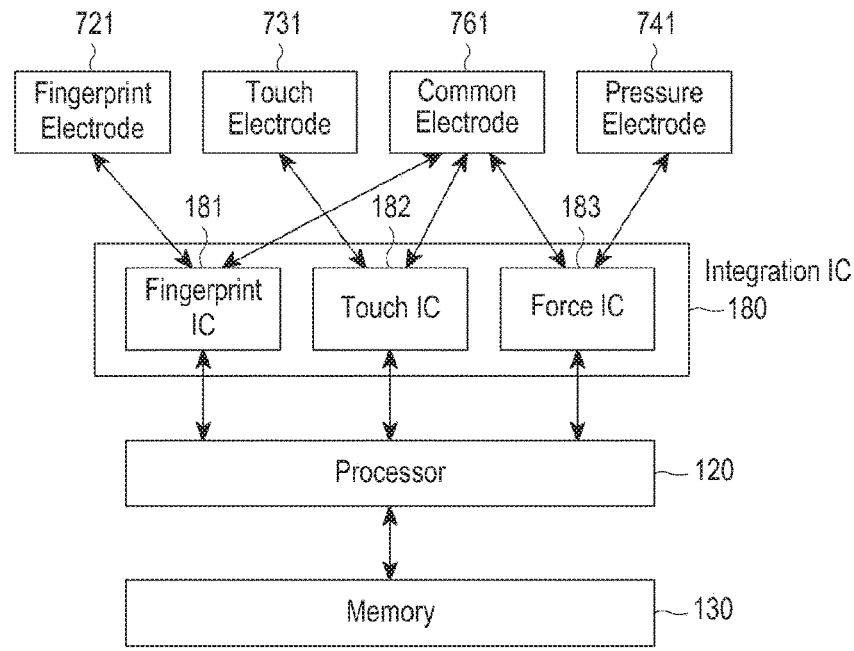
FIGS. 36 to 39 are block diagrams each illustrating an integrated circuit (IC) connected to electrodes of a display device, according to an embodiment of the present disclosure.
Figure 37:
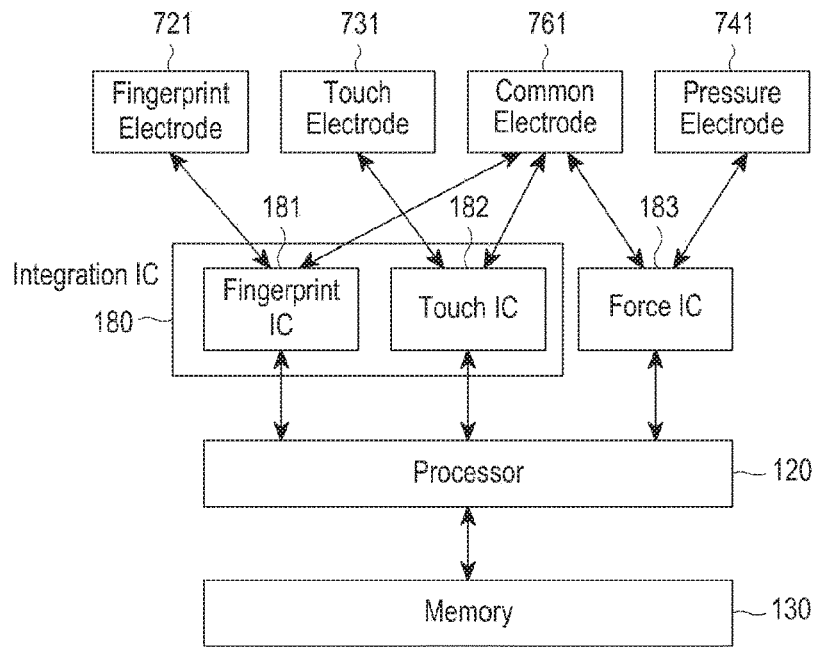
Figure 38:
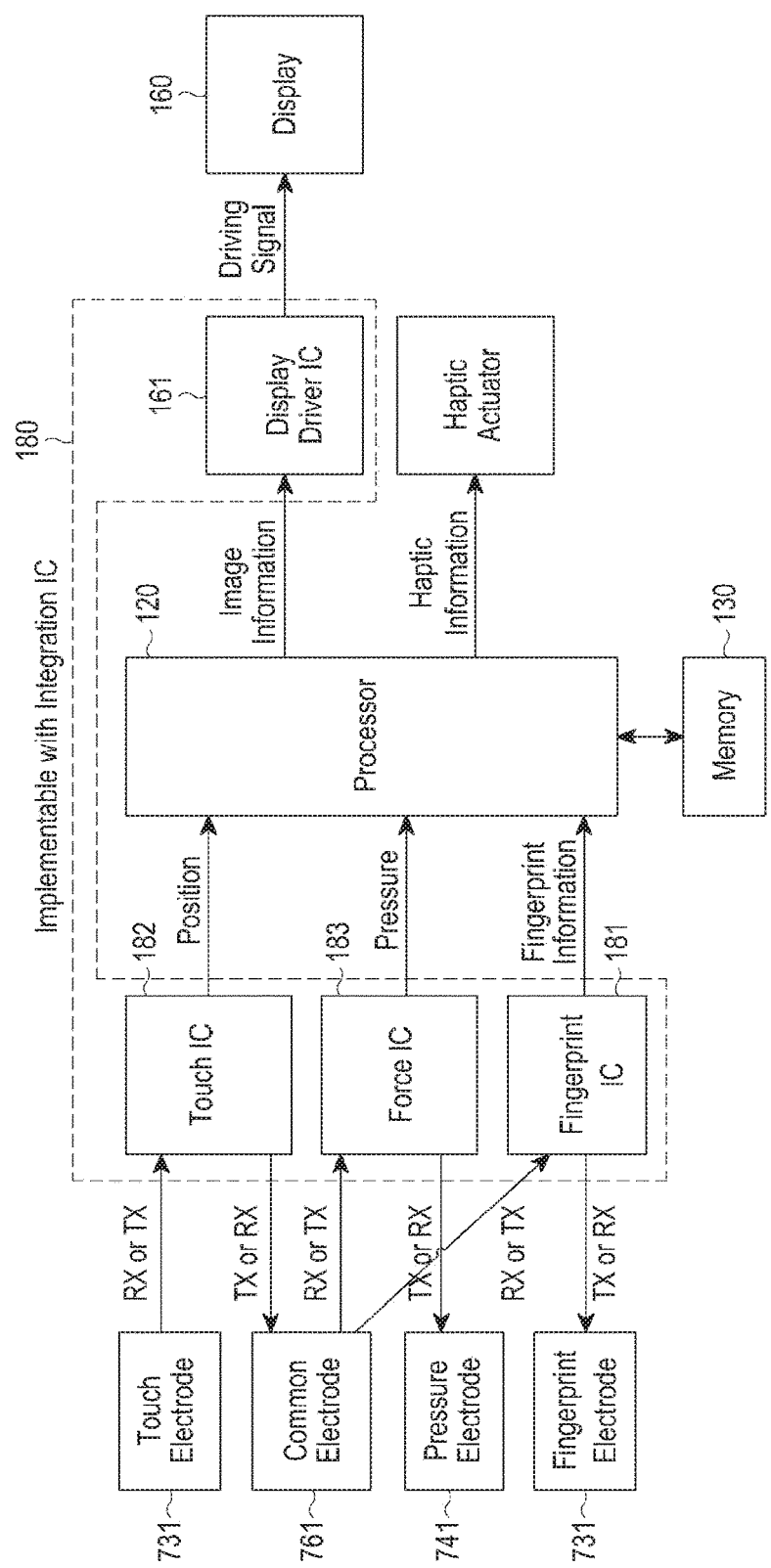

As illustrated in FIGS. 36 to 38, the display device includes a fingerprint electrode 721, a common electrode 761, a touch electrode 731, and/or a pressure electrode 741. The fingerprint electrode 721, the common electrode 761, the touch electrode 731, and the pressure electrode 741 may correspond to the fingerprint electrode 321, the common electrode 361, the touch electrode 331, and the pressure electrode 341 according to the embodiment of FIG. 10, respectively.

According to an embodiment of the present disclosure, the fingerprint sensor may include two electrodes, for example, a fingerprint electrode 721 and a common electrode 761, which are formed on each support member. The fingerprint sensor may be implemented through an electrical connection between the fingerprint electrode 721 disposed on one support member and the common electrode 761 on the other support member. When the fingerprint electrode 721 is activated and operates as a reception electrode, the common electrode 761 may be activated and operate as the transmission electrode.

According to an embodiment of the present disclosure, the common electrode 761 may also be electrically connected to the touch electrode 731 and/or the pressure electrode 741, in addition to the connection with the fingerprint electrode 721. Accordingly, the touch sensor 230 may be realized through the electrical connection between the touch electrode 731 and the common electrode 761, and the pressure sensor may be implemented through the electrical connection between the pressure electrode 741 and the common electrode 761. When the common electrode 761 is activated and operates as a transmission electrode, the touch electrode 731 and/or the pressure electrode 741 may be activated and operate as a reception electrode. In another example, when the common electrode 261 is activated and operates as a reception electrode, the fingerprint electrode 721, the touch electrode 731, and/or the pressure electrode 741 may be activated and operate as a reception electrode.

According to an embodiment of the present disclosure, at least some (e.g., two or more) of a fingerprint sensor, a touch sensor, and a pressure sensor may be incorporated in a single integrated chip (IC) or integration IC 180. The fingerprint electrode 721 and the common electrode 761 of the fingerprint sensor may be connected to a fingerprint IC 181, the touch electrode 731 and the common electrode 761 of the touch sensor may be connected to a touch IC 182, and the pressure electrode 741 and the common electrode 761 of the pressure sensor may be connected to a pressure IC 183 to perform a sensing operation according to a circuit operation.

According to an embodiment of the present disclosure, at least two ICs of the fingerprint IC 181, the touch IC 182, and the pressure IC 183 may operate as an integration IC 180. As illustrated in FIG. 36, the fingerprint IC 181, the touch IC 182, and the pressure IC 183 may be integrated into one integration IC 180 to collectively process whether or not a fingerprint, a touch position, and a pressure of a user's finger are sensed. As illustrated in FIG. 37, the fingerprint IC 181 and the touch IC 182 may be integrated into one integration IC 180 to collectively process whether or not a fingerprint or a touch position of a user's finger is sensed, and the other pressure IC 183 may be directly connected to the processor 120 so as to separately process the pressure sensing of the pressure of the user's finger.

According to an embodiment of the present disclosure, at least two of the fingerprint IC 181, the touch IC 182, the pressure IC 183, and a display driving IC 161 may operate as an integration IC 180. As illustrated in FIG. 38, the fingerprint IC 181, the touch IC 182, the pressure IC 183, and the display driving IC 161 may be configured as one integration IC 180 so that it is possible to collectively process whether or not a fingerprint, a touch position, and a pressure of a user's finger are sensed. The ICs may be coupled to the processor.

The processor 120 may drive an operating system or an application program so as to control a plurality of hardware or software components connected thereto, and may also perform various data processing and arithmetic operations. The processor 120 may be implemented by, for example, a system-on-chip (SoC). The AP 120 may further include a graphic processing unit (GPU) and/or an image signal processor. The AP 120 may load a command or data received from at least one of the other components (e.g., a non-volatile memory) in a volatile memory to process the command and data, and may store resultant data in a non-volatile memory.

The memory 130 may include, for example, an internal memory or an external memory. The internal memory may include at least one of, for example, a volatile memory (e.g., a DRAM, an SRAM, or an SDRAM), a non-volatile memory (e.g., an one time programmable ROM (OTPROM), a PROM, an EPROM, an EEPROM, a mask ROM, a flash ROM, a flash memory, a hard drive, and a solid state drive (SSD). The external memory may include a flash drive (e.g., a compact flash (CF), a secure digital (SD), a micro secure digital (micro-SD), a mini secure digital (mini-SD), an extreme digital (xD), a multi-media card (MMC), or a memory stick), and the like. The external memory may be functionally or physically connected to the electronic device through various interfaces.

Figure 39:
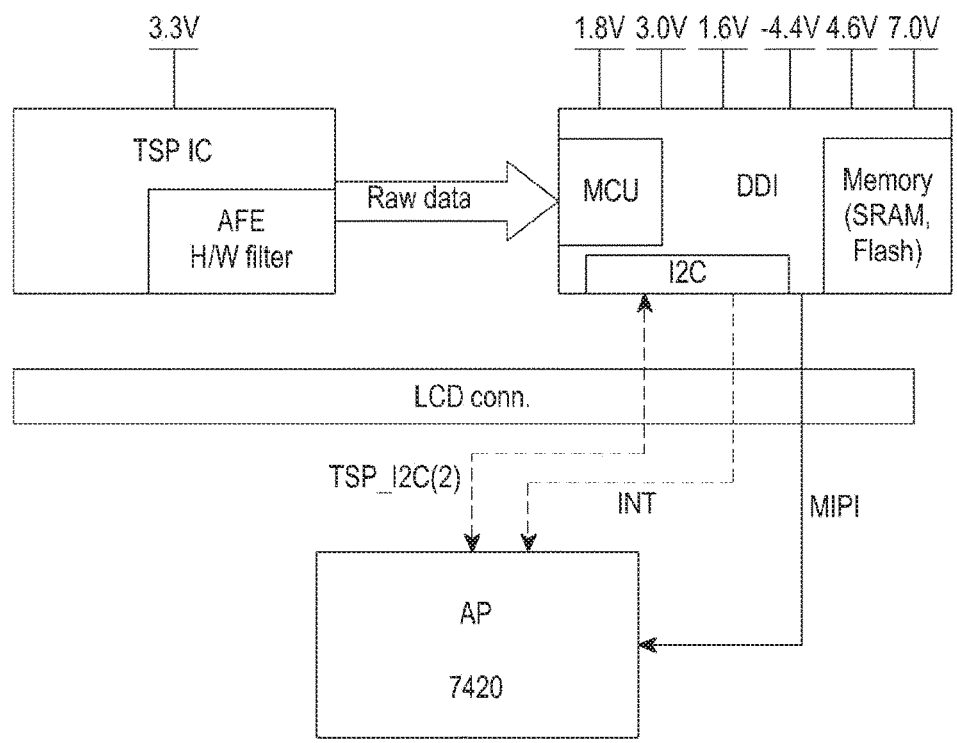

As illustrated in FIG. 39, an IC integration structure may be configured by integrating a touch screen panel (TSP) integration IC and a display driver IC (DDI). The TSP integration IC may be configured by connecting a pressure sensor to a remaining channel of the TSP IC to drive the pressure sensor simultaneously with a touch sensor. Alternatively, a fingerprint sensor may be integrated to be simultaneously driven. The DDI may be integrated with the TSP integration IC to correctively process data. A coordinate and an event according to a touch position according to the DDI integration may be processed through a TSP analog front end (AFE), a DDI, and an AP.

Figure 40:
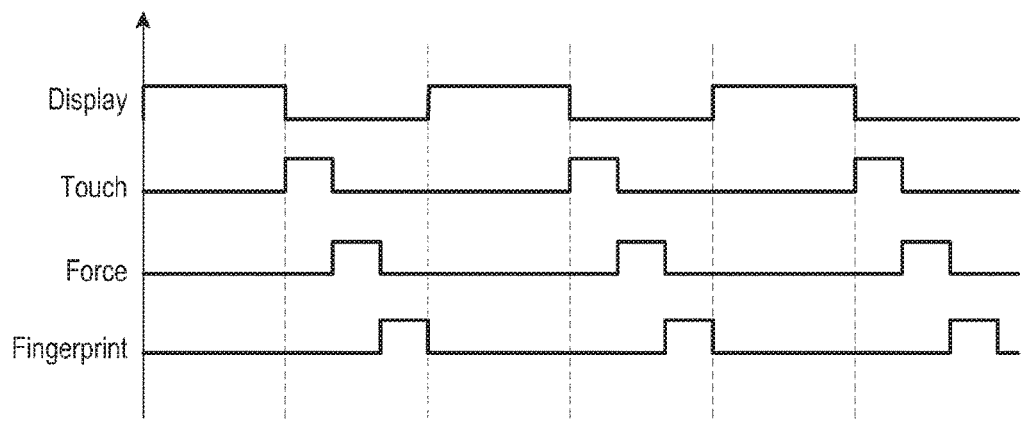
FIGS. 40 to 42 are graphs each illustrating time-division switching of a display device, according to an embodiment of the present disclosure.
Figure 41:
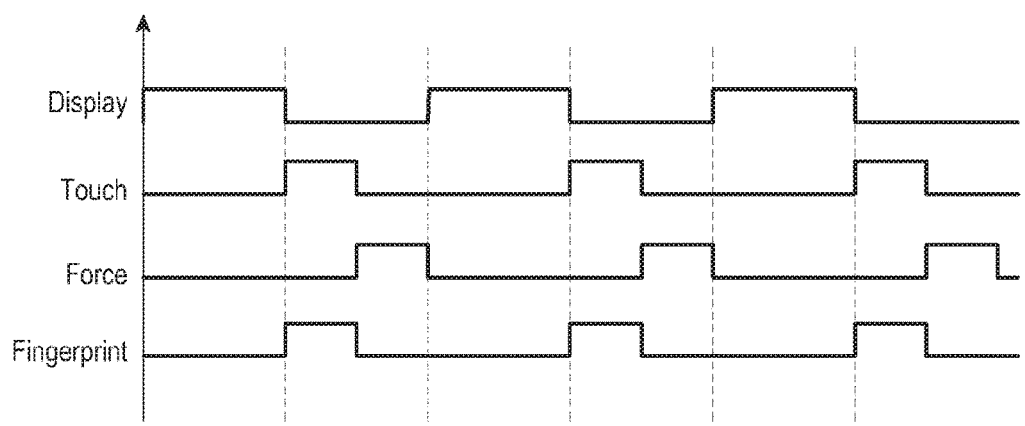
Figure 42:
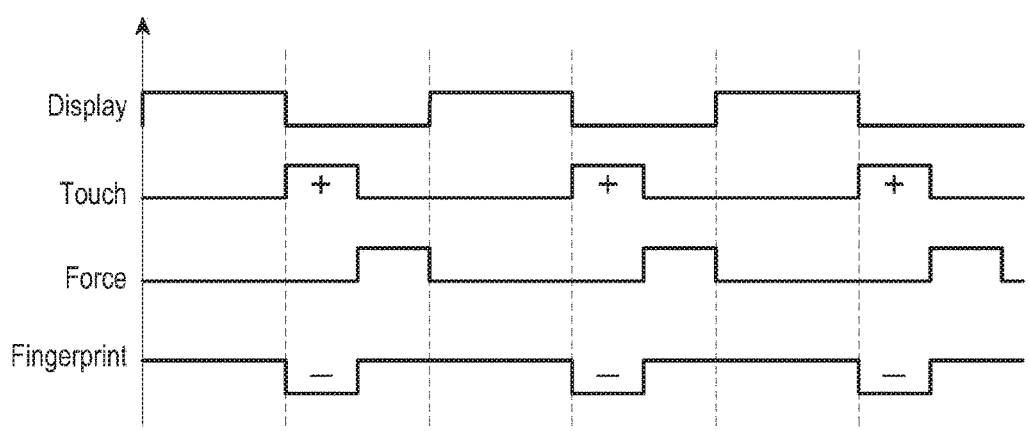

FIGS. 40 to 42 are graphs each illustrating time-division switching of a display device, according to an embodiment of the present disclosure.

FIGS. 40 to 42 exemplify methods in which a display 210 and electrodes are driven in different periods and the electrodes are driven in different periods in order to reduce a signal interference between the display 210 and other adjacent electrodes. The embodiments of FIGS. 29 to 32 may be applied to the time-division switching of each of the fingerprint electrode, the touch electrode, and the pressure electrode.

According to an embodiment of the present disclosure, a display device of an electronic device may be driven repeatedly. The driving region of the display and the driving region between the other electrodes are separated from each other so as not to interfere with each other, and the total driving time of the other electrodes and the driving time of the display may be the same.

As illustrated in FIG. 40, when a drive voltage is applied such that the display is driven in one period region, a screen may be output through the display. In another period, the fingerprint sensor, the touch electrode, and/or the pressure electrode may be driven to detect a fingerprint sensing signal, a touch sensing signal, and/or a pressure sensing signal. The fingerprint electrode, the touch electrode, and/or the pressure electrode may be time divisionally driven in different time periods so that no interference occurs therebetween.

As illustrated in FIG. 41, among the electrodes, signals of two electrodes may be simultaneously driven in the same period. After the display is driven in one time period to output a screen, the fingerprint electrode and the touch electrode may be driven simultaneously in another time period so that a fingerprint sensing signal and a touch sensing signal may be simultaneously detected. A pressure sensing signal may be detected by driving the pressure electrode at a driving time different from that of the fingerprint electrode and the touch electrode in another time period.

As illustrated in FIG. 42, among the electrodes, signals of two electrodes may be inversely driven in the same period. After the display is driven in one period region to output a screen, the fingerprint electrode and the touch electrode may be driven simultaneously in another time period so that a fingerprint sensing signal and a touch sensing signal may be simultaneously detected. When the fingerprint electrode is driven in the (−) direction, the touch electrode may be driven in the (+) direction. A pressure sensing signal may be detected by driving the pressure electrode at a driving time different from that of the fingerprint electrode and the touch electrode in another period.

However, in addition to the driving method as described above, the directions of the touch electrode and the fingerprint electrode may be different from each other, and two of the fingerprint electrode, the touch electrode, and the pressure electrode may be driven in the same period.

As described above, according to an embodiment of the present disclosure, an electronic device includes a housing that includes a first face that faces a first direction, and a second face that faces a second direction, which is opposite to the first direction, the housing including a transparent cover that forms at least a portion of the first face, a display disposed between the first face and the second face of the housing and exposed through the transparent cover, a fingerprint sensor disposed between the transparent cover and the display, a touch sensor disposed between the fingerprint sensor and the display, and a pressure sensor disposed between the display and the second face of the housing.

According to an embodiment of the present disclosure, almost the entire area of the fingerprint sensor overlaps with the display when viewed from a position above the transparent cover.

According to an embodiment of the present disclosure, the fingerprint sensor includes a first support member disposed between the transparent cover and the display and extending parallel to the display, the first support member including a face that faces the first direction, a first electrode disposed on a face of the first support member, which faces the first direction, a second electrode disposed between the transparent cover and the first electrode, and a first insulating layer disposed between the first electrode and the second electrode.

According to an embodiment of the present disclosure, the pressure sensor includes a third electrode disposed between the display and a second face of the housing, a fourth electrode disposed between the third electrode and the second face of the housing, and a second insulating layer disposed between the third electrode and the fourth electrode.

According to an embodiment of the present disclosure, an electronic device includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a first electrode disposed between the transparent cover and the display, a second electrode disposed between the first electrode and the display, a third electrode disposed between the second electrode and the display; a fourth electrode disposed between the third electrode and the display, and at least one control circuit electrically connected to the display, the first electrode, the second electrode, the third electrode, and the fourth electrode.

The at least one control circuit is configured to sense a fingerprint of a user's finger that touches the first face using the first electrode and the second electrode, sense a touch position of the finger using the second electrode and the third electrode, and sense a pressure of the finger on the first face using at least two of the second to fourth electrodes.

According to an embodiment of the present disclosure, the electronic device further includes a first dielectric layer disposed between the first electrode and the second electrode, a second dielectric layer disposed between the second electrode and the third electrode, and a third dielectric layer disposed between the third electrode and the fourth electrode.

According to an embodiment of the present disclosure, the third dielectric layer includes at least a portion whose material is different from that of the first dielectric layer or the second dielectric layer.

According to an embodiment of the present disclosure, the third dielectric layer is thicker than the first dielectric layer or the second dielectric layer.

According to an embodiment of the present disclosure, the at least one control circuit is configured to apply a transmission signal to the second electrode, and receive a reception signal corresponding to the transmission signal through the first electrode, the third electrode, and the fourth electrode.

According to an embodiment of the present disclosure, the at least one control circuit is configured to receive the reception signal through at least one of the first electrode, the third electrode, and the fourth electrode during a first time period, and receive the reception signal through at least another one of the first electrode, the third electrode, and the fourth electrode during a second time period.

According to an embodiment of the present disclosure, the first electrode, the second electrode, the third electrode, or the fourth electrode includes at least one of ITO, IZO, PEDOT, an Ag nanowire, a transparent polymer conductor, and graphene.

According to an embodiment of the present disclosure, an electronic device includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a first electrode disposed between the transparent cover and the display, a second electrode disposed between the first electrode and the display, a third electrode disposed between the second electrode and the display, a fourth electrode disposed on a plane that is coplanar with the third electrode, and at least one control circuit electrically connected to the display, the first electrode, the second electrode, the third electrode, and the fourth electrode. The at least one control circuit is configured to sense a fingerprint of a user's finger that touches the first face using the first electrode and the second electrode, a touch position of the finger using the second electrode and the third electrode, and a pressure of the finger on the first face using the second electrode and the fourth electrode.

According to an embodiment of the present disclosure, almost the entire area of the fingerprint sensor overlaps with the display when viewed from a position above the transparent cover, and the fingerprint sensor is made of a transparent conductive material.

According to an embodiment of the present disclosure, the first electrode is arranged parallel to the third direction and provided in a plural number such that each of the first electrodes transmits or receives a sensing signal, the third electrode or the fourth electrode is arranged parallel to the third direction and is provided in a plural number such that each of the third electrodes or fourth electrodes transmits or receives a sensing signal, arrangement patterns of the plurality of first electrodes, third electrodes, and fourth electrodes are arranged to have an area where the plurality of first electrodes, third electrodes, and fourth electrodes partially overlap with each other, and the plurality of third electrodes and fourth electrodes are alternately disposed.

According to an embodiment of the present disclosure, the electronic device further includes at least one control circuit that is electrically connected to the display device, the first electrode, the second electrode, the third electrode, and the fourth electrode, the second electrode is arranged parallel to a fourth direction that is orthogonal to the third direction and is provided in a plural number such that each of the second electrodes transmits or receives a sensing signal, and the control circuit is configured to apply a transmission signal to the second electrode, and receive a reception signal corresponding to the transmission signal through the first electrode, the third electrode, and the fourth electrode.

According to an embodiment of the present disclosure, the first electrode has an area that is smaller than that of each of the second to fourth electrodes.

According to an embodiment of the present disclosure, an interval between the first electrodes is narrower than the interval between the plurality of third electrodes and fourth electrodes.

According to an embodiment of the present disclosure, an electronic device includes a housing including a first face that faces a first direction and a second face that faces a second direction, which is opposite to the first direction, the housing including a transparent cover that forms at least a portion of the first face, a display disposed between the first face and the second face of the housing and exposed through the transparent cover, a fingerprint electrode disposed between the transparent cover and the display, a touch electrode disposed between the fingerprint electrode and the display, and a pressure electrode disposed between the touch electrode and the display.

One electrode of the fingerprint electrode, the touch electrode, and the pressure electrode is divided into at least two groups. During a first time period, a driving voltage is applied through at least one of the divided groups and a ground voltage is applied to at least another one of the divided groups, and during a second time period, a driving voltage is applied through at least another one of the divided groups to which no driving voltage is applied during the first time period and a ground voltage is applied to at least still another one of the divided groups.

According to an embodiment of the present disclosure, the fingerprint electrode is integrally formed on one face of the transparent cover, and the touch electrode or the pressure electrode is integrally formed on the upper or lower face of the display.

According to an embodiment of the present disclosure, the electronic device further includes, at least one polarizing member above the display through which a screen output from the display is transmitted, and at least one of the fingerprint electrode, the touch electrode, and the pressure electrode are integrally formed above or below the optical member.

While the present disclosure has been shown and described with reference to certain embodiments thereof, it will be apparent to those skilled in the art that the present disclosure is not limited to these embodiments, and various changes in form and details may be made therein without departing from the spirit and scope of the present disclosure as defined by the appended claims and their equivalents.

What is claimed is:

1. An electronic device comprising:
    a housing including a first face that faces a first direction and a second face that faces a second direction, which is opposite to the first direction, the housing including a transparent cover that forms at least a portion of the first face;
    a display disposed between the first face and the second face of the housing and exposed through the transparent cover;
    a fingerprint sensor disposed between the transparent cover and the display;
    a touch sensor disposed between the fingerprint sensor and the display; and
    a pressure sensor disposed between the display and the second face of the housing.

2. The electronic device of claim 1, wherein substantially an entire area of the fingerprint sensor overlaps with the display when viewed from a position above the transparent cover.

3. The electronic device of claim 1, wherein the fingerprint sensor includes:
    a first support member disposed between the transparent cover and the display, extending parallel to the display, and including a face that faces the first direction;
    a first electrode disposed on a face of the first support member, which faces the first direction;
    a second electrode disposed between the transparent cover and the first electrode; and
    a first insulating layer disposed between the first electrode and the second electrode.

4. The electronic device of claim 1, wherein the pressure sensor includes:
    a third electrode disposed between the display and a second face of the housing;
    a fourth electrode disposed between the third electrode and the second face of the housing; and a second insulating layer disposed between the third electrode and the fourth electrode.

5. An electronic device comprising:

a housing including a first face that faces a first direction and a second face that faces a second direction, which is opposite to the first direction, the housing including a transparent cover that forms at least a portion of the first face;

a display disposed between the first face and the second face of the housing and exposed through the transparent cover;

a first electrode disposed between the transparent cover and the display;

a second electrode disposed between the first electrode and the display;

a third electrode disposed between the second electrode and the display;

a fourth electrode disposed between the third electrode and the display; and at least one control circuit electrically connected to the display, the first electrode, the second electrode, the third electrode, and the fourth electrode, wherein the at least one control circuit is configured to:

sense a fingerprint of a user's finger that touches the first face using the first electrode and the second electrode;

sense a touch position of the user's finger using the second electrode and the third electrode; and sense a pressure of the user's finger on the first face using at least two of the second to fourth electrodes.

6. The electronic device of claim 5, further comprising:

a first dielectric layer disposed between the first electrode and the second electrode;

a second dielectric layer disposed between the second electrode and the third electrode; and a third dielectric layer disposed between the third electrode and the fourth electrode.

7. The electronic device of claim 6, wherein the third dielectric layer includes at least a portion of material which is different from that of the first dielectric layer or the second dielectric layer.

8. The electronic device of claim 6, wherein the third dielectric layer is thicker than the first dielectric layer or the second dielectric layer.

9. The electronic device of claim 5, wherein the at least one control circuit is further configured to:

apply a transmission signal to the second electrode; and receive a reception signal corresponding to the transmission signal through the first electrode, the third electrode, and the fourth electrode.

10. The electronic device of claim 9, wherein the at least one control circuit is further configured to:

receive the reception signal through at least one of the first electrode, the third electrode, and the fourth electrode during a first time period; and receive the reception signal through at least another one of the first electrode, the third electrode, and the fourth electrode during a second time period.

11. The electronic device of claim 5, wherein at least one of the first electrode, the second electrode, the third electrode, and the fourth electrode includes at least one of indium-tin-oxide (ITO), indium-zinc-oxide (IZO), poly (3,4-ethylenedioxythiophene) (PEDOT) polystyrene sulfonate, a silver (Ag) nanowire, a transparent polymer conductor, and graphene.

12. An electronic device comprising:

a housing including a first face that faces a first direction and a second face that faces a second direction, which is opposite to the first direction, the housing including a transparent cover that forms at least a portion of the first face;

a display disposed between the first face and the second face of the housing and exposed through the transparent cover;

a first electrode disposed between the transparent cover and the display;

a second electrode disposed between the first electrode and the display;

a third electrode disposed between the second electrode and the display;

a fourth electrode disposed to be coplanar with the third electrode; and at least one control circuit electrically connected to the display, the first electrode, the second electrode, the third electrode, and the fourth electrode, wherein the at least one control circuit is configured to:

sense a fingerprint of a user's finger that touches the first face using the first electrode and the second electrode;

sense a touch position of the user's finger using the second electrode and the third electrode; and sense a pressure of the user's finger on the first face using the second electrode and the fourth electrode.

13. The electronic device of claim 12, wherein substantially an entire area of the fingerprint sensor overlaps with the display when viewed from a position above the transparent cover, and the fingerprint sensor is made of a transparent conductive material.

14. The electronic device of claim 12, wherein the first electrode is arranged parallel to the third direction and is provided in a plural number such that each of the first electrodes transmits or receives a sensing signal, the third electrode or the fourth electrode is arranged parallel to the third direction and is provided in a plural number such that each of the third electrodes or the fourth electrodes transmits or receives a sensing signal, arrangement patterns of the plurality of first electrodes, third electrodes, and fourth electrodes are arranged to have an area where the plurality of third electrodes and fourth electrodes partially overlap with each other, and the plurality of third electrodes and fourth electrodes are alternately disposed.

15. The electronic device of claim 14, further comprising:

at least one control circuit electrically connected to the display, the first electrode, the second electrode, the third electrode, and the fourth electrode, wherein the second electrode is arranged parallel to a fourth direction that is orthogonal to the third direction and is provided in a plural number such that each of the first electrodes transmits or receives a sensing signal, and the at least one control circuit is configured to:

apply a transmission signal to the second electrode; and receive a reception signal corresponding to the transmission signal through the first electrode, the third electrode, and the fourth electrode.

16. The electronic device of claim 15, wherein the first electrode has an area that is smaller than that of each of the second to fourth electrodes.

17. The electronic device of claim 15, wherein an interval between the first electrodes is narrower than an interval between the plurality of third electrodes and fourth electrodes.

* * * * *